(12) United States Patent
Isami et al.

(10) Patent No.: US 10,429,402 B2
(45) Date of Patent: Oct. 1, 2019

(54) WASHING/DRYING APPARATUS, SCREENING APPARATUS, WASHING/DRYING METHOD, AND SCREENING METHOD

(71) Applicant: NIKON CORPORATION, Tokyo (JP)

(72) Inventors: Tadao Isami, Yokohama (JP); Muneki Hamashima, Fukaya (JP); Takehiko Ueda, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 551 days.

(21) Appl. No.: 15/039,766

(22) PCT Filed: Nov. 25, 2014

(86) PCT No.: PCT/JP2014/081059
§ 371 (c)(1),
(2) Date: Nov. 4, 2016

(87) PCT Pub. No.: WO2015/080083
PCT Pub. Date: Jun. 4, 2015

(65) Prior Publication Data
US 2017/0045543 A1    Feb. 16, 2017

(30) Foreign Application Priority Data

Nov. 29, 2013   (JP) .................... 2013-247162

(51) Int. Cl.
*B01L 99/00*    (2010.01)
*B08B 3/04*     (2006.01)
(Continued)

(52) U.S. Cl.
CPC .............. *G01N 35/04* (2013.01); *B01L 99/00* (2013.01); *B08B 3/04* (2013.01); *G01N 33/53* (2013.01);
(Continued)

(58) Field of Classification Search
CPC .............. B01L 99/00; B08B 3/02; B08B 3/04
See application file for complete search history.

(56) References Cited

U.S. PATENT DOCUMENTS

| 5,853,962 A * | 12/1998 | Bowers ................ B08B 7/0092 430/331 |
| 2003/0082587 A1 * | 5/2003 | Seul ..................... B01J 19/0046 435/6.12 |

(Continued)

FOREIGN PATENT DOCUMENTS

| JP | 60-53850 | 3/1985 |
| JP | 7-249605 | 9/1995 |

(Continued)

OTHER PUBLICATIONS

International Search Report dated Feb. 10, 2015 in corresponding International Application No. PCT/JP2014/081059.
(Continued)

*Primary Examiner* — Mikhail Kornakov
*Assistant Examiner* — Natasha N Campbell

(57) ABSTRACT

There is a possibility that an arrangement of a cleaning device and a drying device may result in an inefficient usage of a space for an installation. A cleaning and drying apparatus 30 for a plate including a biochip is provided with: a cleaning device 310 that is configured to clean the plate 60; and a drying device 320 that is configured to dry the plate 60, the drying device 320 is arranged above the cleaning device 310.

19 Claims, 13 Drawing Sheets

(51) Int. Cl.
    *G01N 35/04* (2006.01)
    *G01N 33/53* (2006.01)
    *G01N 35/02* (2006.01)
    *G01N 35/00* (2006.01)
    *G01N 33/543* (2006.01)
    *G01N 35/10* (2006.01)
    *B01L 3/00* (2006.01)

(52) U.S. Cl.
    CPC ....... *G01N 33/54386* (2013.01); *G01N 35/00* (2013.01); *G01N 35/00029* (2013.01); *G01N 35/02* (2013.01); *G01N 35/1002* (2013.01); *B01L 3/5085* (2013.01); *B01L 2300/0819* (2013.01); *B01L 2300/0829* (2013.01); *G01N 2035/00158* (2013.01); *G01N 2035/0437* (2013.01)

(56) References Cited

U.S. PATENT DOCUMENTS

2004/0200509 A1* 10/2004 Felder .................. B08B 3/02
    134/26
2008/0122955 A1 5/2008 Sugita
2008/0223411 A1* 9/2008 Mokuo ............ H01L 21/67028
    134/25.4
2013/0260396 A1 10/2013 Akcakir
2013/0274119 A1 10/2013 Knutson et al.

FOREIGN PATENT DOCUMENTS

| | | |
|---|---|---|
| JP | 8-122223 | 5/1996 |
| JP | 2003-194833 | 7/2003 |
| JP | 2003-297886 | 10/2003 |
| JP | 2004-239778 | 8/2004 |
| JP | 2008-39564 | 2/2008 |
| JP | 2013-533469 | 8/2013 |
| WO | WO 2006/017737 A2 | 2/2006 |

OTHER PUBLICATIONS

European Search Report dated Jul. 7, 2017 in corresponding European Patent Application No. 14866476.6.
Written Opinion dated Feb. 10, 2015 in corresponding International Patent Application No. PCT/JP2014/081059.
Office Action dated Feb. 20, 2018, in corresponding Japanese Patent Application No. 2015-550926, 8 pgs.
Office Action dated May 23, 2017, in corresponding Japanese Patent Application No. 2015-550926, 7 pgs.

* cited by examiner

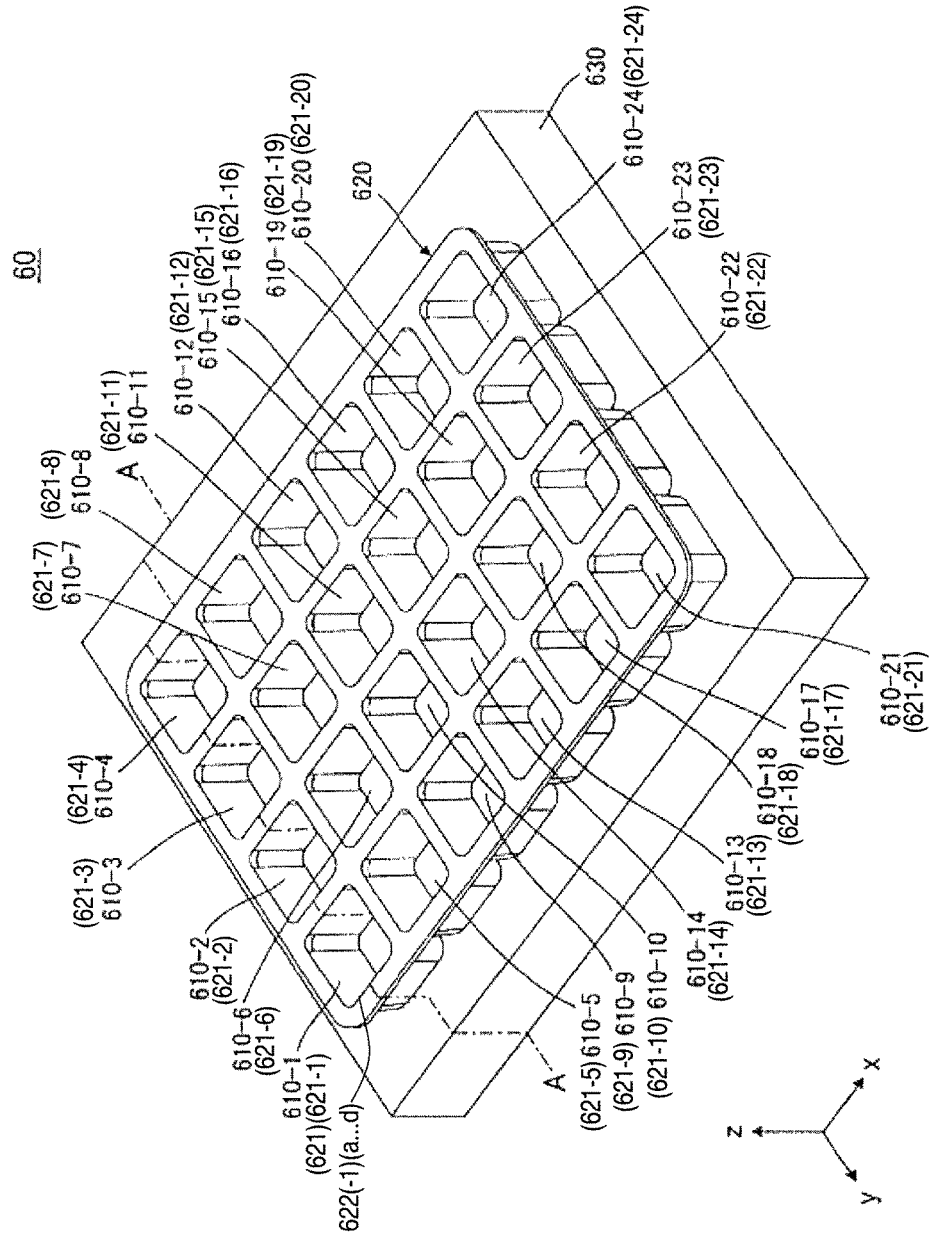
[FIG. 1]

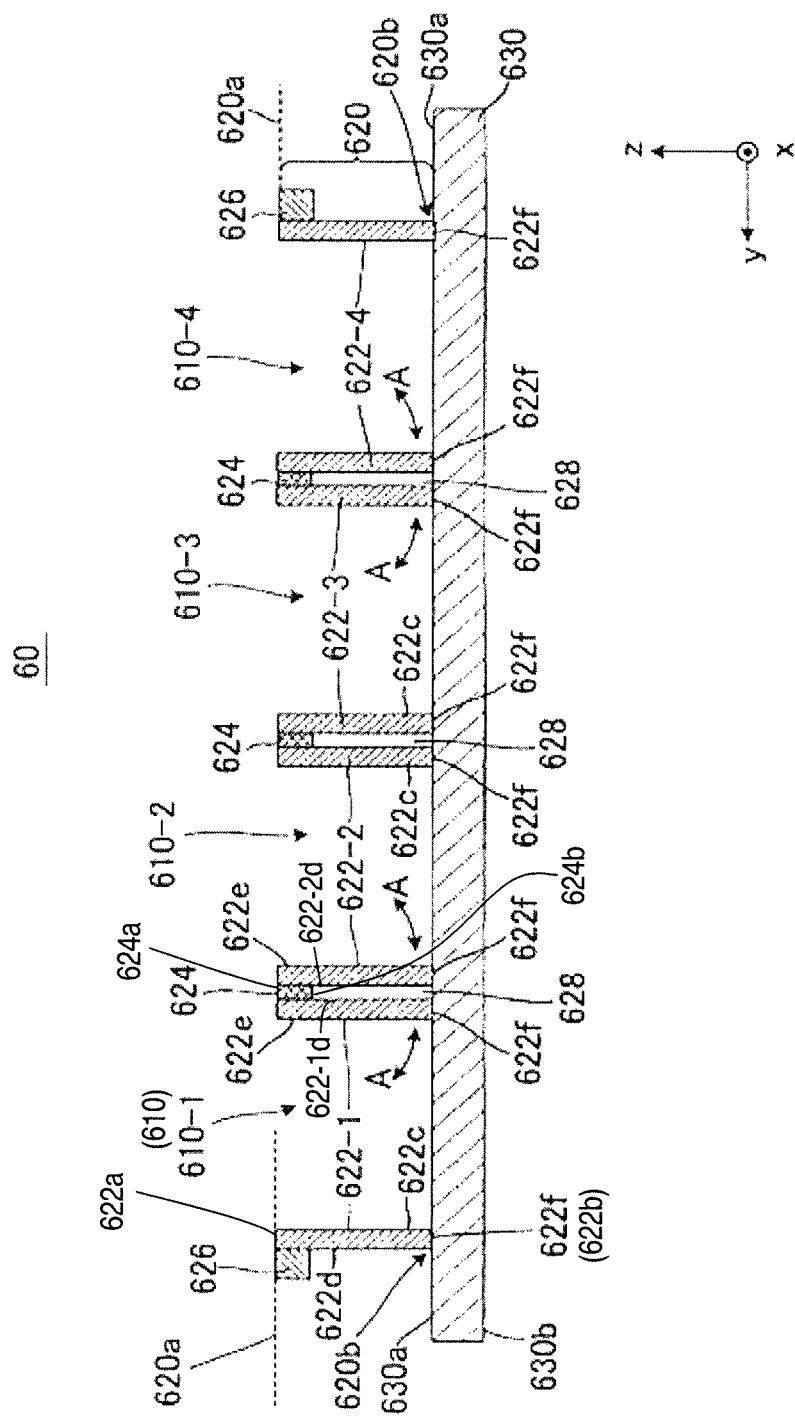

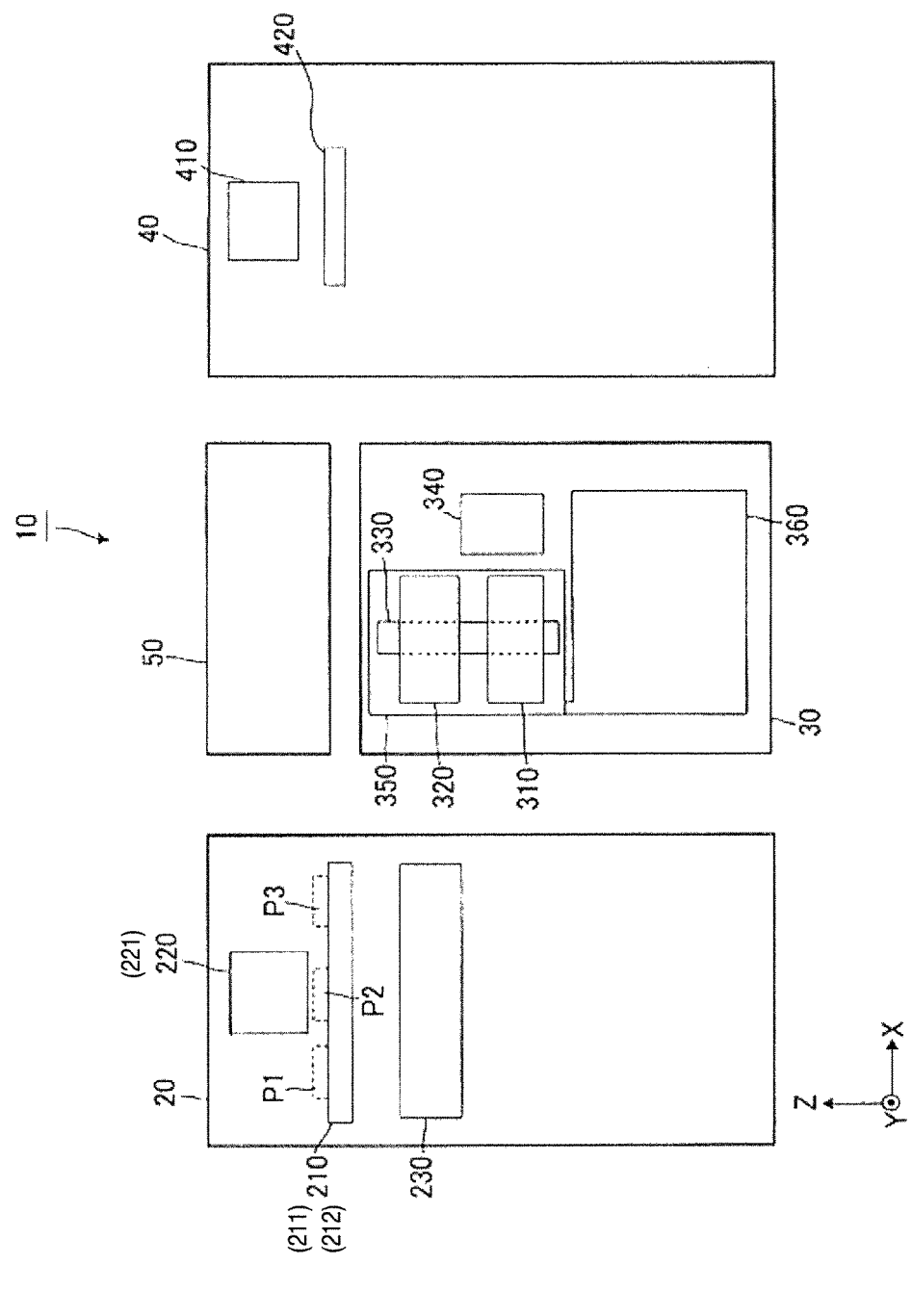

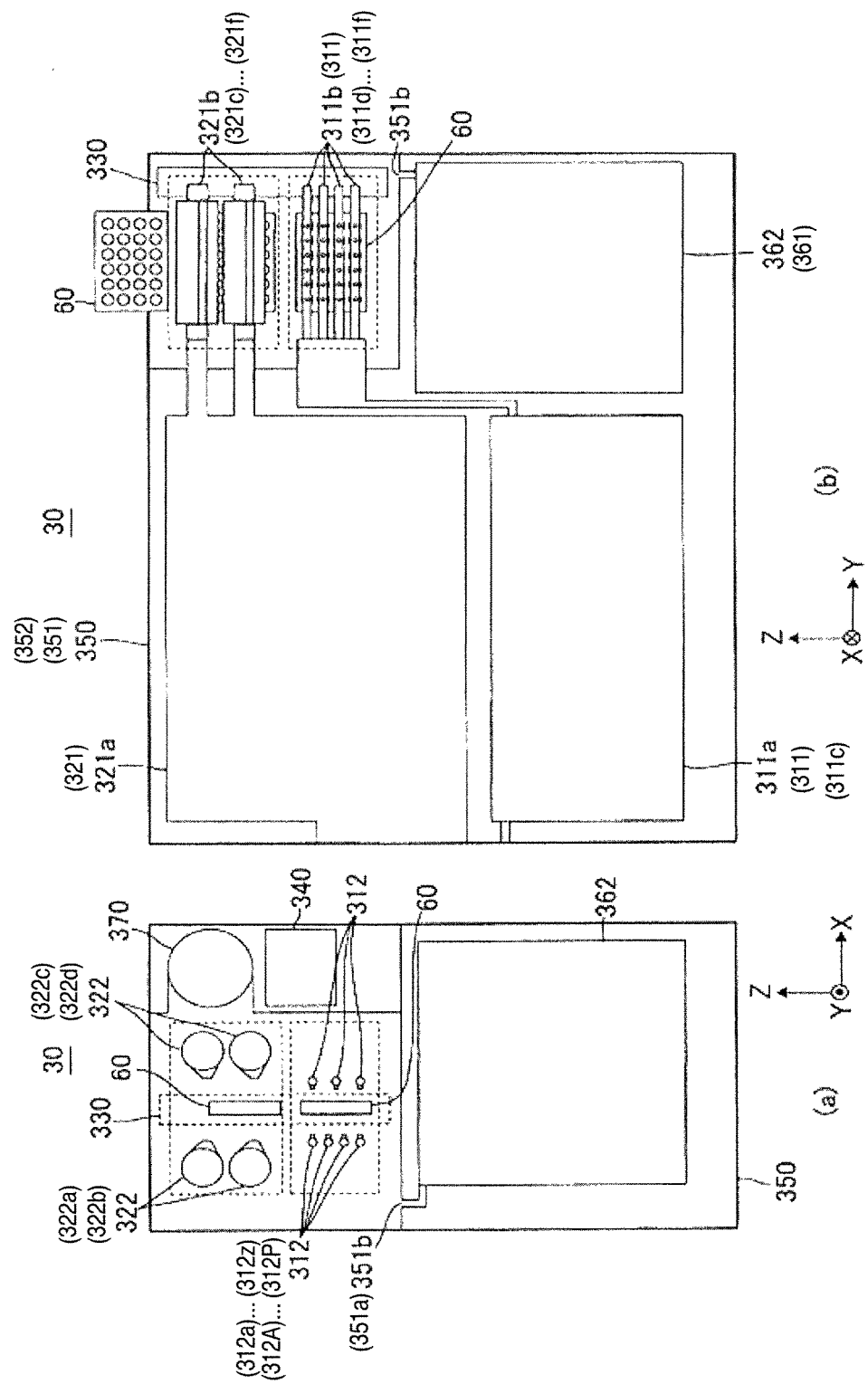

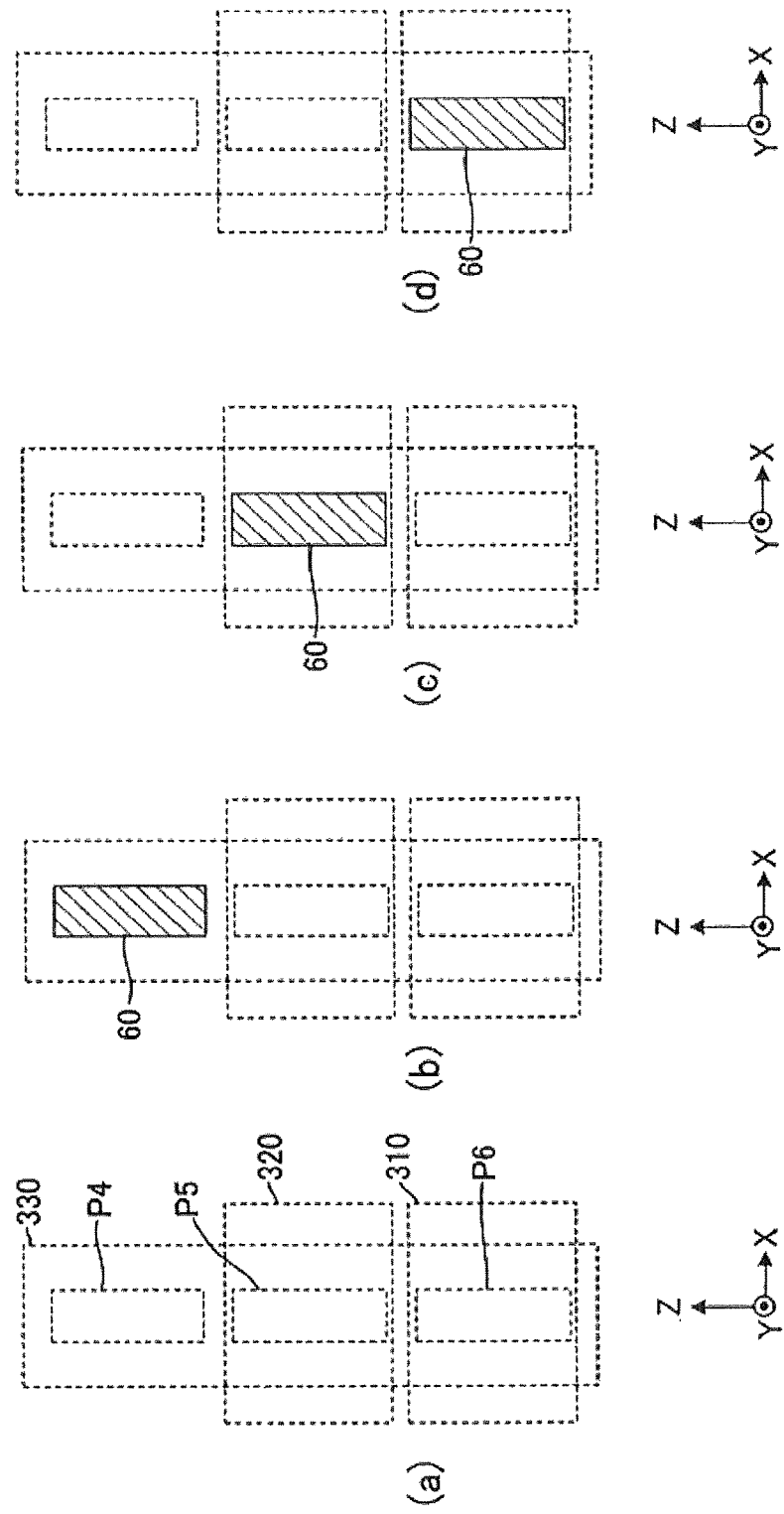
[FIG. 5]

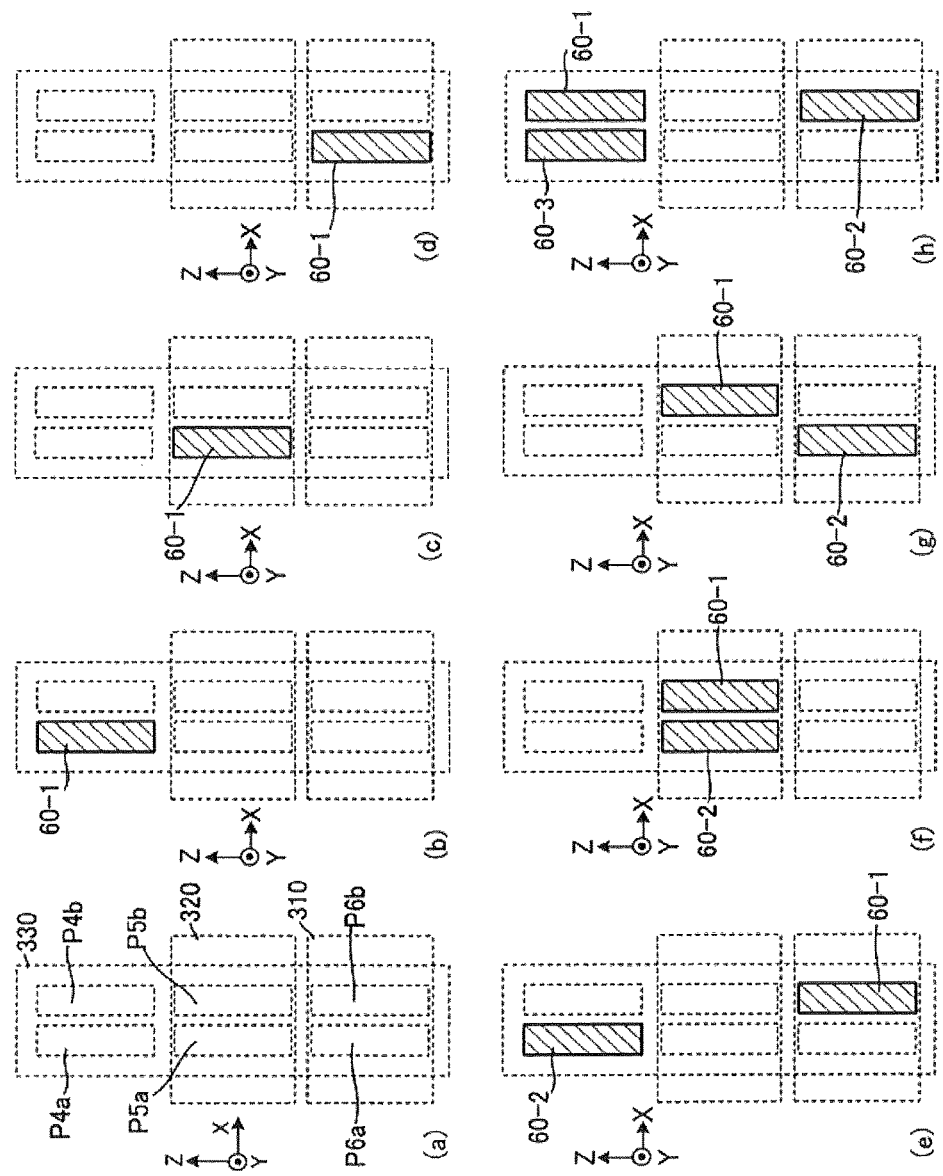
[FIG. 6]

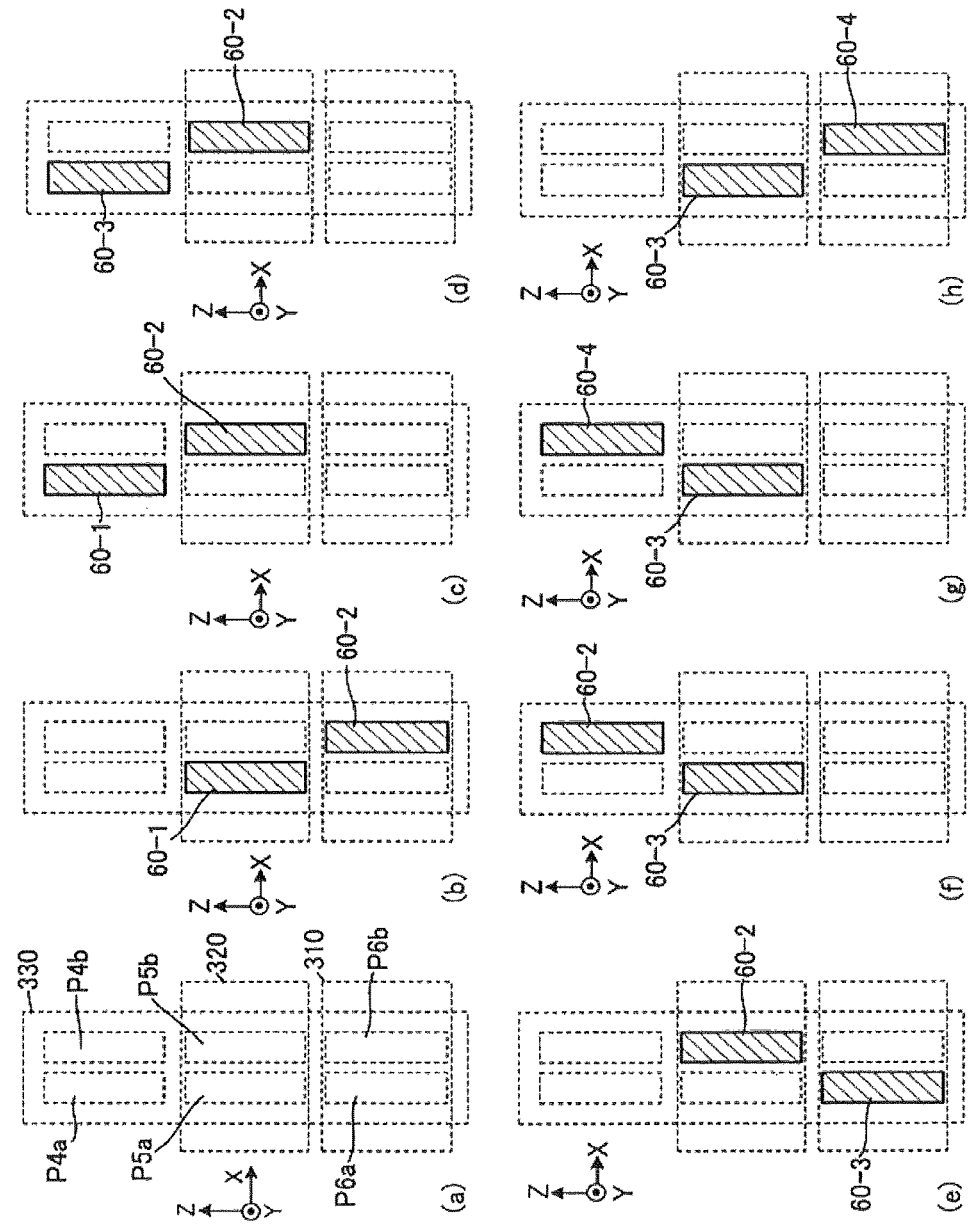
[FIG. 7]

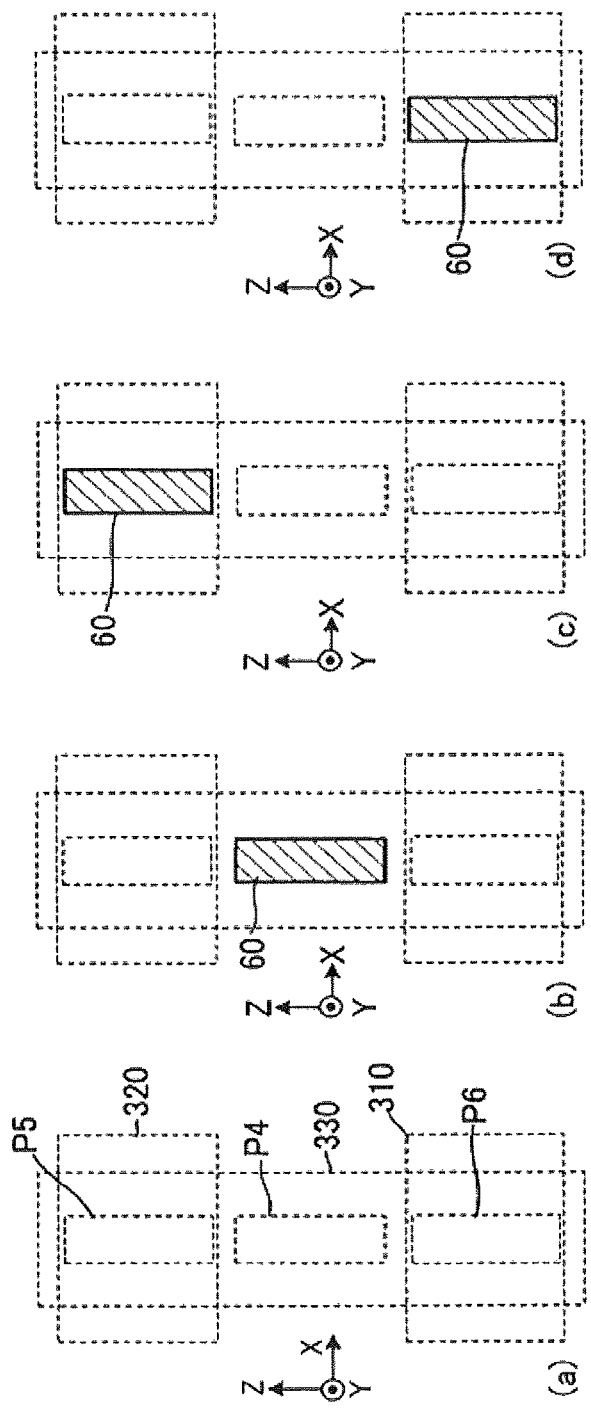
[FIG. 8]

[FIG. 9]
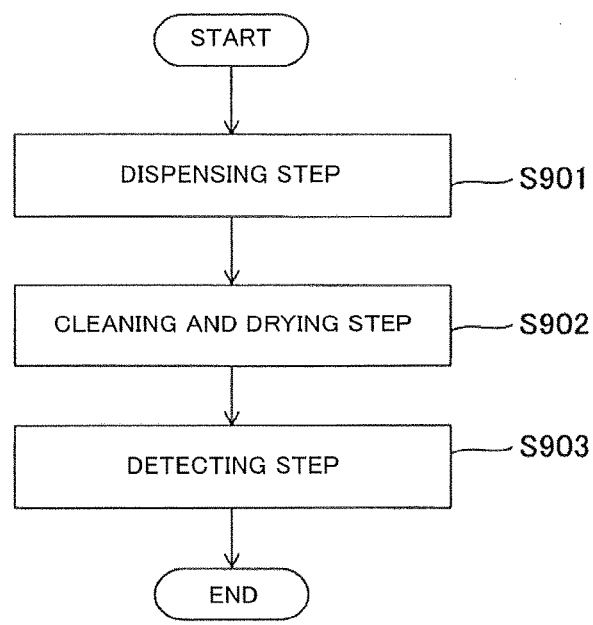

[FIG. 10]
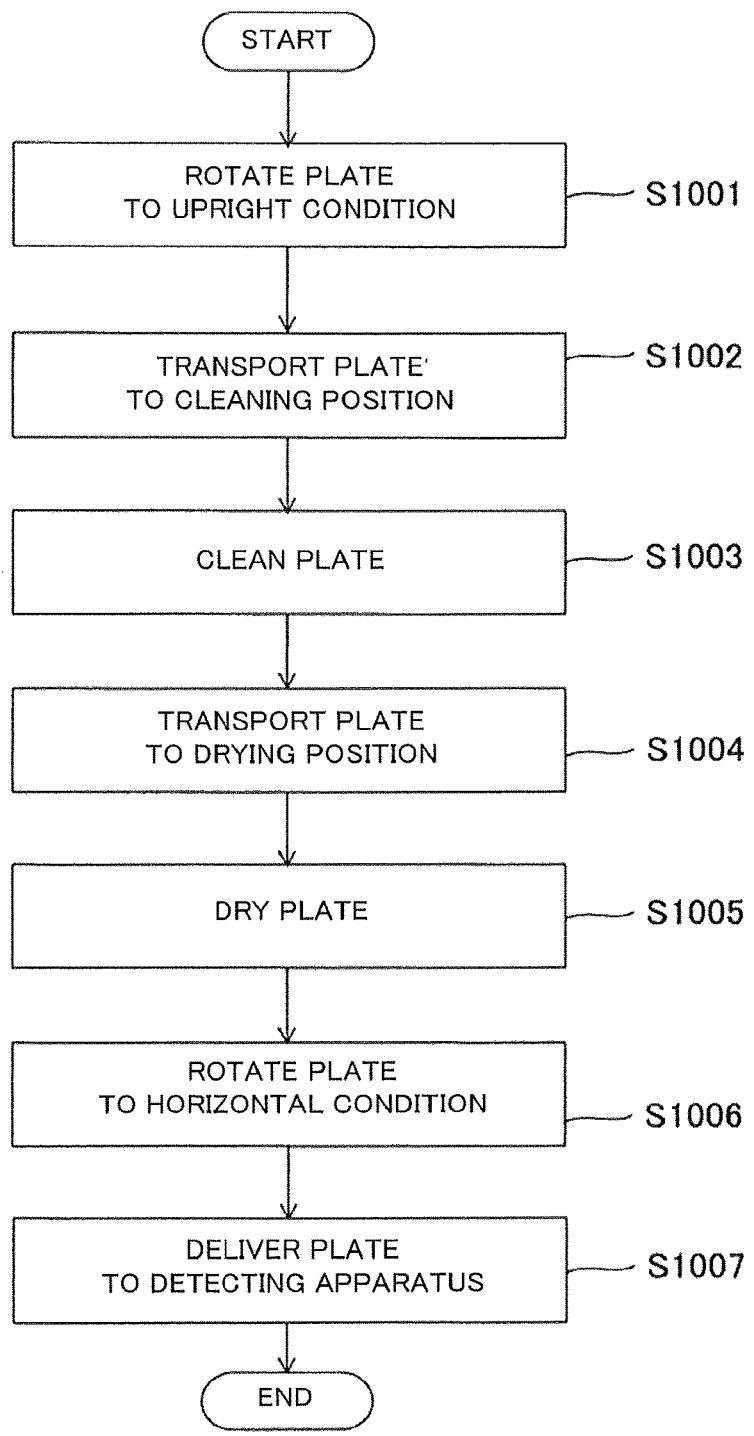

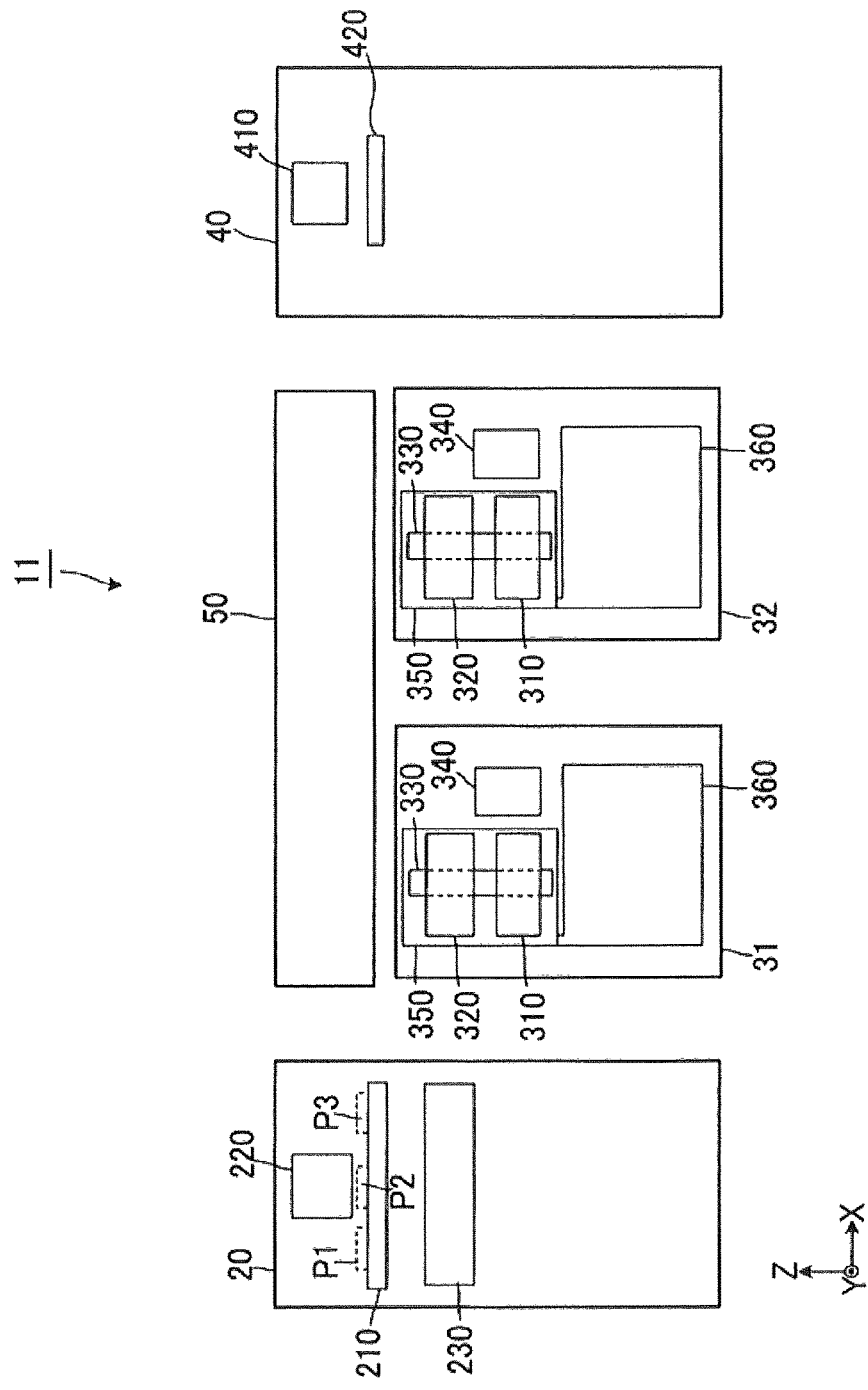
[FIG. 11]

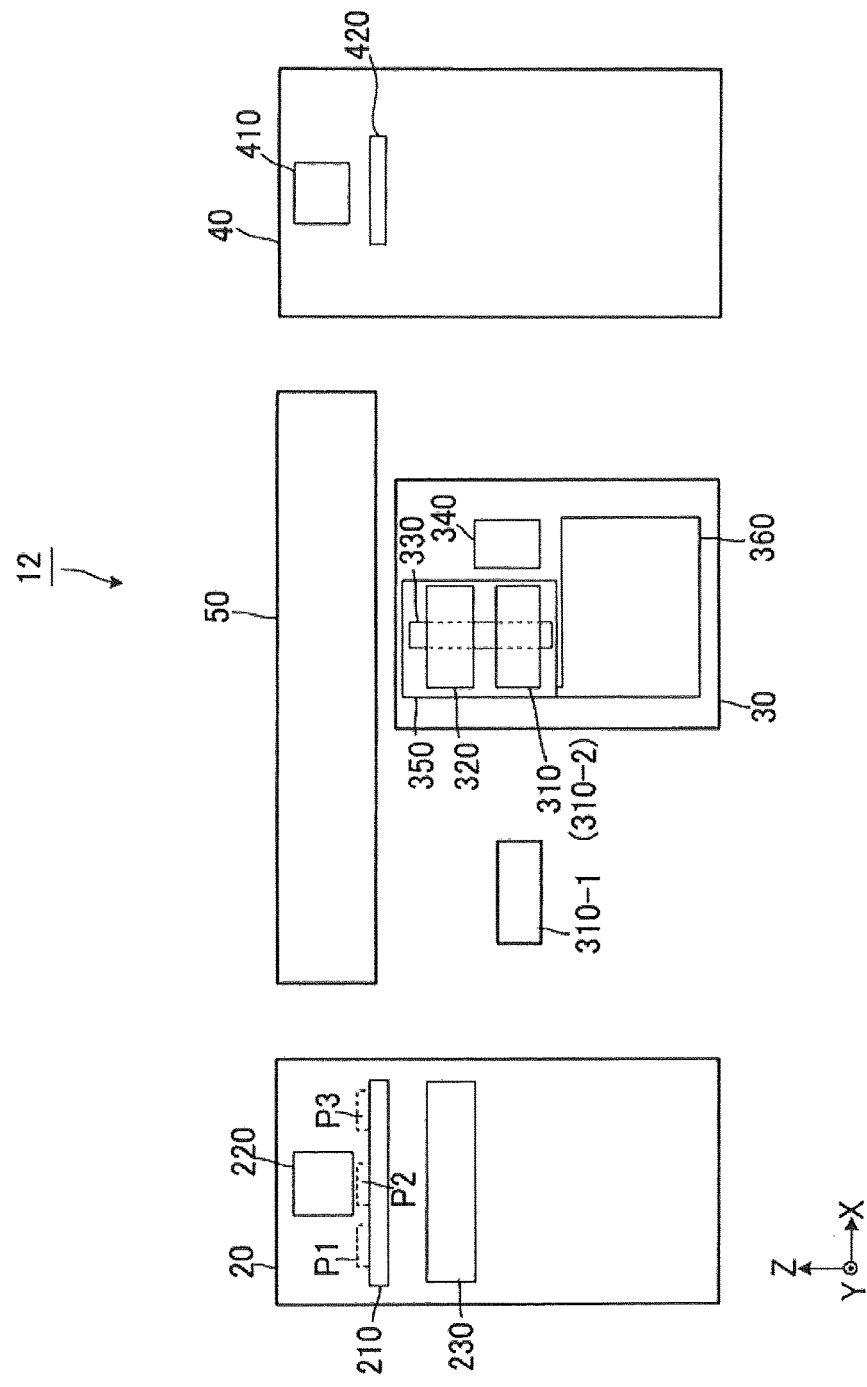

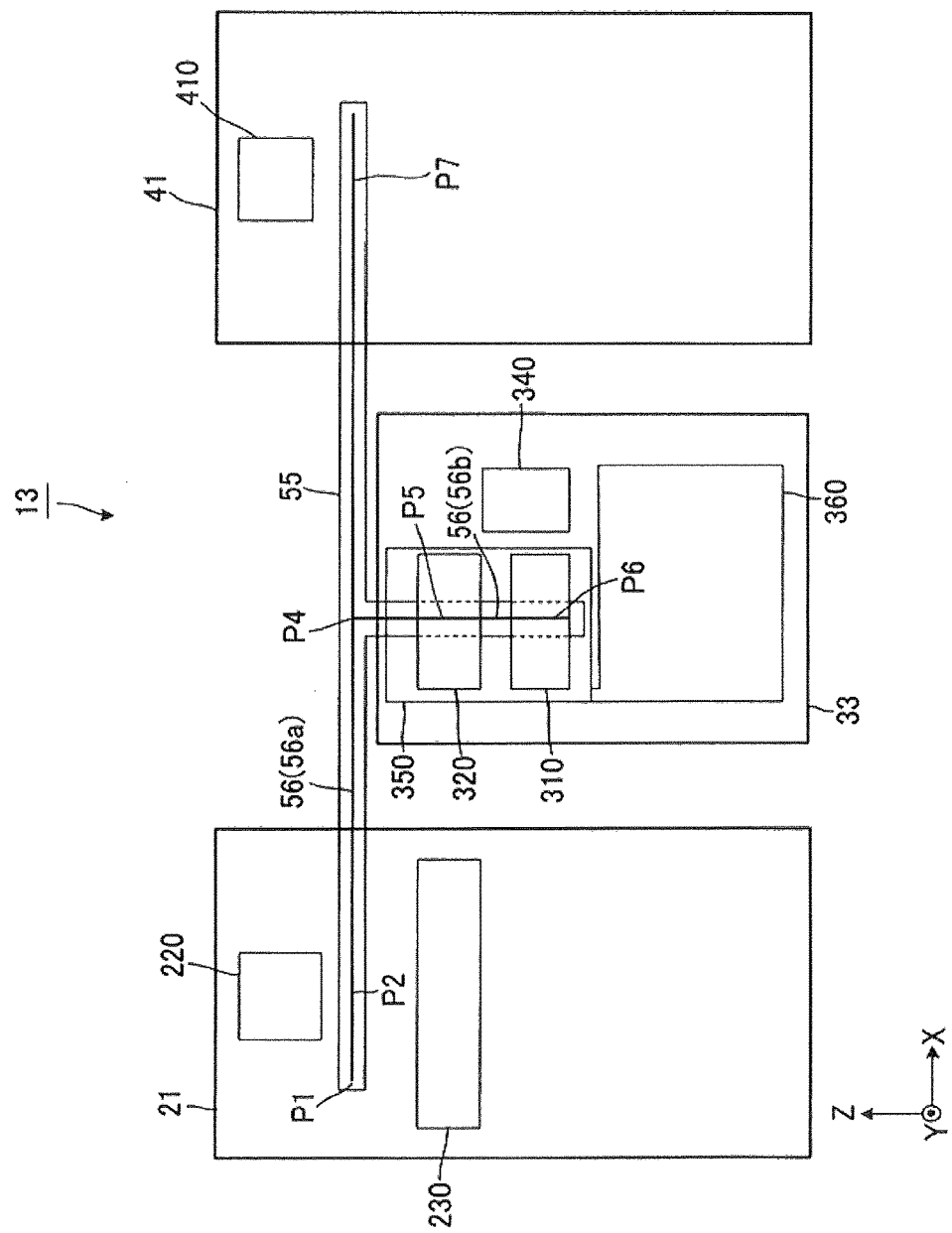
[FIG. 13]

WASHING/DRYING APPARATUS, SCREENING APPARATUS, WASHING/DRYING METHOD, AND SCREENING METHOD

CROSS-REFERENCE TO RELATED APPLICATIONS

This application is a U.S. National Stage Application, which claims the benefit under 35 U.S.C. § 371 of PCT International Patent Application No. PCT/JP2014/081059, filed Nov. 25, 2014, which claims the foreign priority benefit under 35 U.S.C. § 119 of Japanese Patent Application No. 2013-247162, filed Nov. 29, 2013, the contents of which are incorporated herein by reference.

TECHNICAL FIELD

The present invention relates to a cleaning and drying apparatus, a screening apparatus, a cleaning and drying method and a screening method.

BACKGROUND ART

A cleaning apparatus is provided with a supplying part 11 for a used microplate, a cleaning part 12 and a housing part 13 for a cleaned microplate, and the housing part 13 is provided with a microplate holding and transporting mechanism that is substantially same as the supplying part 11 and is furthermore configured to dry the cleaned microplate (for example, see a Patent Literature 1).

CITATION LIST

Patent Literature

Patent Literature 1: Japanese Unexamined Patent Application Publication No. Sho60-53850 (1985-53850)

SUMMARY OF INVENTION

Technical Problem

There is a possibility that an arrangement of a cleaning device and a drying device may result in an inefficient usage of a space for an installation.

Solution to Problem

One aspect of the present invention is a cleaning and drying apparatus for a plate having a biochip, the cleaning and drying apparatus is provided with: a cleaning part that is configured to clean the plate; and a drying part that is configured to dry the plate, the drying part is arranged above the cleaning part.

According to another aspect of the present invention, the cleaning part is configured to clean the plate in an upright condition and the drying part is configured to dry the plate in an upright condition, in the above described one aspect.

Another aspect of the present invention is provided with a transporting part that is configured to upwardly transport the plate cleaned by the cleaning part to the drying part, in the above described one aspect.

According to another aspect of the present invention, the transporting part is configured to downwardly transport the uncleaned plate to the cleaning part while allowing the uncleaned plate to pass through the drying part, in the above described one aspect.

According to another aspect of the present invention, the transporting part is configured to transport the plate in a vertical direction from the cleaning part to the drying part at an upper side, in the above described one aspect.

According to another aspect of the present invention, the drying part is arranged above the cleaning part in a vertical direction, in the above described one aspect.

According to another aspect of the present invention, the cleaning part is configured to clean both surfaces of the plate and the drying part is configured to dry both surfaces of the plate, in the above described one aspect.

Another aspect of the present invention is provided with a circulating mechanism that is configured to filter exhaust air from the drying part to allow the exhaust air to be reused for the drying, in the above described one aspect.

Another aspect of the present invention is provided with a waste solution storing part below the cleaning part, in the above described one aspect.

According to another aspect of the present invention, a cleaning position in the cleaning part is a position that is displaced in a horizontal direction from a drying position in the drying part, in the above described one aspect.

Another aspect of the present invention is provided with a rotational operating part that is configured to rotate the uncleaned plate in a horizontal condition to an upright condition and then to rotate the dried plate in an upright condition to a horizontal condition again, in the above described one aspect.

One aspect of the present invention is a screening apparatus for a biochip, the screening apparatus is provided with: the cleaning and drying apparatus according to any one of the above described aspects; a dispensing apparatus that is configured to dispense, in a plate having the biochip, a specimen containing a target that is able to react specifically to a biomolecule fixed on the biochip; and a detecting apparatus that is configured to detect affinity between the target and the biomolecule.

Another aspect of the present invention is provided with a transporting apparatus that is configured to transport the plate from the dispensing apparatus to the cleaning and drying apparatus in a horizontal direction and to transport the plate from the cleaning and drying apparatus to the detecting apparatus in a horizontal direction, in the above described one aspect.

According to another aspect of the present invention, the transporting apparatus is configured to transport the plate in a horizontal condition from the dispensing apparatus to the cleaning and drying apparatus in a horizontal direction and to transport the plate in a horizontal condition from the cleaning and drying apparatus to the detecting apparatus in a horizontal direction, in the above described one aspect.

One aspect of the present invention is a cleaning and drying method for a plate having a biochip, the cleaning and drying method is provided with: a first transporting step for transporting the plate to a cleaning position; a cleaning step for cleaning the plate at the cleaning position; a second transporting step for transporting the cleaned plate to a drying position that is located above the cleaning position; and a drying step for drying the plate at the drying position.

According to another aspect of the present invention, the first transporting step is a step for transporting the plate in a upright condition to the cleaning position, the cleaning step is a step for cleaning the plate in a upright condition, the second transporting step is a step for transporting the plate in a upright condition to the drying position, the drying step is a step for drying the plate in a upright condition, in the above described one aspect.

According to another aspect of the present invention, the first transporting step includes a downward transporting step for downwardly transport the plate to the cleaning position while allowing the plate to pass through the drying position, in the above described one aspect, in the above described one aspect.

According to another aspect of the present invention, both surfaces of the plate are cleaned at the cleaning step and both surfaces of the plate are dried at the drying step, in the above described one aspect.

Another aspect of the present invention is provided with a step for rotating the uncleaned plate in a horizontal condition to an upright condition; and a step for rotating the dried plate in an upright condition to a horizontal condition again, in the above described one aspect.

One aspect of the present invention is a screening method using a plate having a biochip, the screening method is provided with: a dispensing step for dispensing, in a plate having a biochip, a specimen containing a target that is able to react specifically to a biomolecule fixed on the biochip, in a dispensing apparatus; at least one of the steps for performing the cleaning and drying method according to any one of claim 15 to claim 19 in a cleaning and drying apparatus; and a detecting step for detecting affinity between the target and the biomolecule in a detecting apparatus.

Another aspect of the present invention is provided with: a step for transporting the dispensed plate from the dispensing apparatus to the cleaning and drying apparatus in a horizontal direction; and a step for transporting the cleaned and dried plate from the cleaning and drying apparatus to the detecting apparatus in a horizontal direction, in the above described one aspect.

According to another aspect of the present invention, the dispensed plate in a horizontal condition is transported from the dispensing apparatus to the cleaning and drying apparatus in a horizontal direction, and the cleaned and dried plate in a horizontal condition is transported from the cleaning and drying apparatus to the detecting apparatus in a horizontal direction, in the above described one aspect.

BRIEF DESCRIPTION OF DRAWINGS

FIG. 1 is a perspective view of a plate that is used by a screening apparatus.

FIG. 2 is a cross sectional view of the plate that is used by the screening apparatus.

FIG. 3 is a drawing conceptually illustrating a structure of the screening apparatus.

FIG. 4 is a drawing conceptually illustrating a structure of a cleaning and drying apparatus.

FIG. 5 is a drawing for describing a control for a cleaning device, a drying device and a transporting device by a controlling device.

FIG. 6 is a drawing for describing a first modified example of the control for the cleaning device, the drying device and the transporting device by the controlling device.

FIG. 7 is a drawing for describing a second modified example of the control for the cleaning device, the drying device and the transporting device by the controlling device.

FIG. 8 is a drawing for describing a third modified example of the control for the cleaning device, the drying device and the transporting device by the controlling device.

FIG. 9 is a flowchart illustrating a screening method by the screening apparatus.

FIG. 10 is a flowchart illustrating a cleaning and drying step in the cleaning and drying apparatus.

FIG. 11 is a drawing conceptually illustrating a structure of the screening apparatus.

FIG. 12 is a drawing conceptually illustrating a structure of the screening apparatus.

FIG. 13 is a drawing conceptually illustrating a structure of the screening apparatus.

DESCRIPTION OF EMBODIMENTS

Hereinafter, with reference to drawings, an embodiment of the present invention will be described in detail.

FIG. 1 is a perspective view of a plate 60 that is used by a screening apparatus 10. The plate 60 is provided with a partitioned member 620 and a board 630. For the convenience of description, in FIG. 1 and below described FIG. 2, a direction that is perpendicular to a second surface 630b of the board 630 that constitutes the plate 60 is a z axis direction, a direction along a long side of the board 630 that constitutes the plate 60 is a x axis direction, and a direction along a short side of the board 630 that constitutes the plate 60 is a y axis direction. The x axis, the y axis and the z axis are orthogonal to one another and thus define intersecting coordinates.

The partitioned member 620 has a first surface 620a and a second surface 620b. The first surface 620a of the partitioned member 620 is a surface that is parallel to a xy plane. The second surface 620b of the partitioned member 620 is a surface that is parallel to the xy plane. The first surface 620a of the partitioned member 620 is formed at a different position in the z axis direction than the second surface 620b of the partitioned member 620. The first surface 620a of the partitioned member 620 is parallel to the second surface 620b of the partitioned member 620.

A partition 621 is a through hole that penetrates from the first surface 620a to the second surface 620b. The partition 621 is a space that substantially has a shape of a quadrangular prism. However, the shape of the partition 621 is not limited to this shape and thus may be a shape of a cylinder, for example.

The partitioned member 620 is provided with barrier walls 622, a linking part 624, and a reinforcing part 626.

The barrier wall 622 is a member that forms the partition 621. The partitioned member 620 has the partitions 621 that are formed by the barrier walls 622.

The partitioned member 620 has, as the barrier walls 622, a first barrier wall 622-1, a second barrier wall 622-2, a third barrier wall 622-3, a fourth barrier wall 622-4, a fifth barrier wall 622-5, a sixth barrier wall 622-6, a seventh barrier wall 622-7, an eighth barrier wall 622-8, a ninth barrier wall 622-9, a tenth barrier wall 622-10, an eleventh barrier wall 622-11, a twelfth barrier wall 622-12, a thirteenth barrier wall 622-13, a fourteenth barrier wall 622-14, a fifteenth barrier wall 622-15, a sixteenth barrier wall 622-16, a seventeenth barrier wall 622-17, an eighteenth barrier wall 622-18, a nineteenth barrier wall 622-19, a twentieth barrier wall 622-20, a twenty first barrier wall 622-21, a twenty second barrier wall 622-22, a twenty third barrier wall 622-23 and a twenty fourth barrier wall 622-24.

Thus, the partitioned member 620 has, as the partitions 621, a total of 24 partitions, i.e., a partition 621-1 that is formed by the first barrier wall 622-1, a partition 621-2 that is formed by the second barrier wall 622-2, a partition 621-3 that is formed by the third barrier wall 622-3, a partition 622-4 that is formed by the fourth barrier wall 622-4, a partition 621-5 that is formed by the fifth barrier wall 622-5, a partition 621-6 formed by the sixth barrier wall 622-6, partition 621-7 that is formed by the seventh barrier wall 622-7, a partition 621-8 that is formed by the eighth barrier wall 622-8, a partition 621-9 that is formed by the ninth barrier wall 622-9, a partition 621-10 that is formed by the tenth barrier wall 622-10, a partition 621-11 that is formed by the eleventh barrier wall 622-11, a partition 621-12 that is formed by the twelfth barrier wall 622-12, a partition 621-13 that is formed by the thirteenth barrier wall 622-13, a partition 621-14 that is formed by the fourteenth barrier wall 622-14, a partition 621-15 that is formed by the fifteenth barrier wall 622-15, a partition 621-16 that is formed by the sixteenth barrier wall 622-16, a partition 621-17 that is formed by the seventeenth barrier wall 622-17, a partition 621-18 that is formed by the eighteenth barrier wall 622-18, a partition 621-19 that is formed by the nineteenth barrier wall 622-19, a partition 621-20 that is formed by the twentieth barrier wall 622-20, a partition 621-21 that is formed by the twenty first barrier wall 622-21, a partition 621-22 that is formed by the twenty second barrier wall 622-22, a partition 621-23 that is formed by the twenty third barrier wall 622-23 and a partition 621-24 that is formed by the twenty fourth barrier wall 622-24.

The partitions 621 are arranged in the partitioned member 620 in a lattice pattern. As an example, a plurality of partitions 621 are arranged along a direction of a long side of the partitioned member 620 and a plurality of partitions 621 are arranged along a direction of a short side of the partitioned member 620. That is, the partitions 621 are arranged in a lattice pattern along the x axis and the y axis. FIG. 1 illustrates a partitioned member 620 in which a total of 24 partitions are formed with six columns thereof along the direction of the long side of the partitioned member 620 and four rows thereof along the direction of the short side of the partitioned member 620. Note that while FIG. 1 illustrates an example of the partitioned member 620 having 24 barrier walls, that is, a partitioned member having 24 partitions, the number of the barrier walls (the number of the partitions) of the partitioned member 620 is not limited to this. Note that while FIG. 1 illustrates an example of the partitioned member 620 in which the barrier walls are formed in the lattice pattern, the arrangement of the barrier walls (an arrangement of the partitions) in the partitioned member 620 is not limited to this.

The barrier wall 622 has a first surface 622a, a second surface 622b, a third surface 622c and a fourth surface 622d.

The first surface 622a of the barrier wall 622 is a surface that is parallel to the xy plane. The first surface 622a of the barrier wall 622 is included in the first surface 620a of the partitioned member 620. That is, the first surface 622a of the barrier wall 622 is formed at the same position in the z axis direction as the first surface 620a of the partitioned member 620. When the plate 60 is formed by joining the partitioned member 620 with the board 630, the first surface 622a of the barrier wall 622 is a surface that is substantially parallel to the second surface 630b of the board 630.

The second surface 622b of the barrier wall 622 is a surface that is parallel to the xy plane. The second surface 622b of the barrier wall 622 is formed at a different position in the z axis direction than the first surface 622a of the barrier wall 622. The second surface 622b of the barrier wall 622 is parallel to the first surface 622a of the barrier wall 622. When the plate 60 is formed by joining the partitioned member 620 with the board 630, the first surface 622a of the barrier wall 622 is positioned at more z axis plus side than the second surface 622b of the barrier wall 622 is. The second surface 622b of the barrier wall 622 is the surface that is joined with the board 630 by welding. A welded part 622f, which will be described later, includes the second surface 622b of the barrier wall 622.

The third surface 622c of the barrier wall 622 is a surface that is formed along an outer edge of the first surface 622a of the barrier wall 622 and an outer edge of the second surface 622b of the barrier wall 622. The third surface 622c of the barrier wall 622 includes a surface that is parallel to a yz plane and a surface that is parallel to a zx plane. The third surface 622c of the barrier wall 622 is an inner wall surface of the barrier wall 622. The third surface 622c of the barrier wall 622 is a surface that defines the partition 621.

The fourth surface 622d of the barrier wall 622 is a surface that is formed along the outer edge of the first surface 622a of the barrier wall 622 and the outer edge of the second surface 622b of the barrier wall 622. The fourth surface 622d of the barrier wall 622 includes a surface that is parallel to the yz plane and a surface that is parallel to the zx plane. The fourth surface 622d of the barrier wall 622 is a surface that is on the opposite side from the third surface 622c of the barrier wall 622. The fourth surface 622d of the barrier wall 622 is an outer wall surface of the barrier wall 622.

The linking part 624 is a member that links the barrier walls 622. For example, the linking part 624 is a member that links the barrier walls including the first barrier wall 622-1 to the twenty fourth barrier wall 622-24.

Each of the first barrier wall 622-1 to the twenty fourth barrier wall 622-24 is linked to another barrier wall by the linking part 624. As an example, each of the first barrier wall 622-1 to the twenty fourth barrier wall 622-24 is linked to a neighboring barrier wall by the linking part 624.

As an example, the first barrier wall 622-1 is linked to the second barrier wall 622-2 by the linking part 624. The first barrier wall 622-1 is linked to the fifth barrier wall 622-5 by the linking part 624. Therefore, the first barrier wall 622-1 is linked to two barrier walls—the second barrier wall 622-2 and the fifth barrier wall 622-5—by the linking part 624.

As another example, the second barrier wall 622-2 is linked to the first barrier wall 622-1 by the linking part 624. The second barrier wall 622-2 is linked to the third barrier wall 622-3 by the linking part 624. The second barrier wall 622-2 is linked to the sixth barrier wall 622-6 by the linking part 624. Therefore, the second barrier wall 622-2 is linked to three barrier walls—the first barrier wall 622-1, the third barrier wall 622-3 and the sixth barrier wall 622-6—by the linking part 624.

As another example, the sixth barrier wall 622-6 is linked to the second barrier wall 622-2 by the linking part 624. The sixth barrier wall 622-6 is linked to the fifth barrier wall 622-5 by the linking part 624. The sixth barrier wall 622-6 is linked to the seventh barrier wall 622-7 by the linking part 624. The sixth barrier wall 622-6 is linked to the tenth barrier wall 622-10 by the linking part 624. Therefore, the sixth barrier wall 622-6 is linked to four barrier walls—the second barrier wall 622-2, the fifth barrier wall 622-5, the seventh barrier wall 622-7 and the tenth barrier wall 622-10—by the linking part 624.

As an example, each of the first barrier wall 622-1 to the twenty fourth barrier wall 622-24 is linked not only to the neighboring barrier wall but also to a barrier wall other than the neighboring barrier wall by the linking part 624. As an example, the first barrier wall 622-1 is linked to all the barrier walls from the second barrier wall 622-2 to the twenty fourth barrier wall 622-24 by the linking part 624. In this way, the partitioned member 620 is integrated by the linking of the plurality of barrier walls by the linking part 624, and thus the partitions 621 are formed.

The linking part 624 includes a first surface 624a and a second surface 624b.

The first surface 624a of the linking part 624 is a surface that is parallel to the xy plane. The first surface 624a of the linking part 624 is included in the first surface 620a of the partitioned member 620. That is, the first surface 624a of the linking part 624 is formed at the same position in the z axis direction as the first surface 620a of the partitioned member 620. When the plate 60 is formed by joining the partitioned member 620 with the board 630, the first surface 624a of the linking part 624 is a surface that is substantially parallel to the second surface 630b of the board 630.

The second surface 624b of the linking part 624 is a surface that is parallel to the xy plane. The second surface 624b of the linking part 624 is formed at a different position in the z axis direction than the first surface 624a of the linking part 624. The second surface 624b of the linking part 624 is parallel to the first surface 624a of the linking part 624. The second surface 624b of the linking part 624 is formed at a different position in the z axis direction than the second surface 622b of the barrier wall 622. As one example, the second surface 624b of the linking part 624 is formed between the first surface 622a of the barrier wall 622 and the second surface 622b of the barrier wall 622 in the z axis direction.

The partitions 621 are formed by the barrier walls 622 in the partitioned member 620 in a condition where a gap 628 is formed between the barrier wall 622 and another barrier wall.

An example using the first barrier wall 622-1 will be described.

A fourth surface 622-1d of the first barrier wall 622-1 is separated from a fourth surface 622-2d of the second barrier wall 622-2. The fourth surface 622-1d of the first barrier wall 622-1 and the fourth surface 622-2d of the second barrier wall 622-2 are separated only by an amount corresponding to the interposing linking part 624. That is, the gap 628 includes a space that is formed by the fourth surface 622-1d of the first barrier wall 622-1, the fourth surface 622-2d of the second barrier wall 622-2 and the second surface 624b of the linking part 624.

The fourth surface 622-1d of the first barrier wall 622-1 is separated from a fourth surface 622-5d of the fifth barrier wall 622-5. The fourth surface 622-1d of the first barrier wall 622-1 and the fourth surface 622-5d of the fifth barrier wall 622-5 are separated only by an amount corresponding to the interposing linking part 624. That is, the gap 628 includes a space that is formed by the fourth surface 622-1d of the first barrier wall 622-1, the fourth surface 622-5d of the fifth barrier wall 622-5 and the second surface 624b of the linking part 624.

The fourth surface 622-1d of the first barrier wall 622-1 is separated from a fourth surface 622-6d of the sixth barrier wall 622-6. The fourth surface 622-1d of the first barrier wall 622-1 and the fourth surface 622-6d of the sixth barrier wall 622-6 are separated only by an amount corresponding to the interposing linking part 624. That is, the gap 628 includes a space that is formed by the fourth surface 622-1d of the first barrier wall 622-1, the fourth surface 622-6d of the sixth barrier wall 622-6 and the second surface 624b of the linking part 624.

The first barrier wall 622-1 forms the partition 621-1 in a condition where the gap 628 is formed between the first barrier wall 622-1 and each of the second barrier wall 622-2, the fifth barrier wall 622-5 and the sixth barrier wall 622-6 that are linked to the first barrier wall 622-1 by the linking part 624.

An example using the second barrier wall 622-2 will be described.

The fourth surface 622-2d of the second barrier wall 622-2 is separated from the fourth surface 622-1d of the first barrier wall 622-1. The fourth surface 622-2d of the second barrier wall 622-2 and the fourth surface 622-1d of the first barrier wall 622-1 are separated only by an amount corresponding to the interposing linking part 624. That is, the gap 628 includes a space that is formed by the fourth surface 622-2d of the second barrier wall 622-2, the fourth surface 622-1d of the first barrier wall 622-1 and the second surface 624b of the linking part 624.

The fourth surface 622-2d of the second barrier wall 622-2 is separated from a fourth surface 622-3d of the third barrier wall 622-3. The fourth surface 622-2d of the second barrier wall 622-2 and the fourth surface 622-3d of the third barrier wall 622-3 are separated only by an amount corresponding to the interposing linking part 624. That is, the gap 628 includes a space that is formed by the fourth surface 622-2d of the second barrier wall 622-2, the fourth surface 622-3d of the third barrier wall 622-3 and the second surface 624b of the linking part 624.

The fourth surface 622-2d of the second barrier wall 622-2 is separated from the fourth surface 622-5d of the fifth barrier wall 622-5. The fourth surface 622-2d of the second barrier wall 622-2 and the fourth surface 622-5d of the fifth barrier wall 622-5 are separated only by an amount corresponding to the interposing linking part 624. That is, the gap 628 includes a space that is formed by the fourth surface 622-2d of the second barrier wall 622-2, the fourth surface 622-5d of the fifth barrier wall 622-5 and the second surface 624b of the linking part 624.

The fourth surface 622-2d of the second barrier wall 622-2 is separated from the fourth surface 622-6d of the sixth barrier wall 622-6. The fourth surface 622-2d of the second barrier wall 622-2 and the fourth surface 622-6d of the sixth barrier wall 622-6 are separated only by an amount corresponding to the interposing linking part 624. That is, the gap 628 includes a space that is formed by the fourth surface 622-2d of the second barrier wall 622-2, the fourth surface 622-6d of the sixth barrier wall 622-6 and the second surface 624b of the linking part 624.

The fourth surface 622-2d of the second barrier wall 622-2 is separated from a fourth surface 622-7d of the seventh barrier wall 622-7. The fourth surface 622-2d of the second barrier wall 622-2 and the fourth surface 622-7d of the seventh barrier wall 622-7 are separated only by an amount corresponding to the interposing linking part 624. That is, the gap 628 includes a space that is formed by the fourth surface 622-2d of the second barrier wall 622-2, the fourth surface 622-7d of the seventh barrier wall 622-7 and the second surface 624b of the linking part 624.

The second barrier wall 622-2 forms the partition 621-2 in a condition where the gap 628 is formed between the second barrier wall 622-2 and each of the first barrier wall 622-1, the third barrier wall 622-3, the fifth barrier wall 622-5, the sixth barrier wall 622-6 and the seventh barrier wall 622-7 that are linked to the second barrier wall 622-2 by the linking part 624.

An example using the sixth barrier wall 622-6 will be described.

The fourth surface 622-6d of the sixth barrier wall 622-6 is separated from the fourth surface 622-1d of the first barrier wall 622-1. The fourth surface 622-6d of the sixth barrier wall 622-6 and the fourth surface 622-1*d* of the first barrier wall 622-1 are separated only by an amount corresponding to the interposing linking part 624. That is, the gap 628 includes a space that is formed by the fourth surface 622-6*d* of the sixth barrier wall 622-6, the fourth surface 622-1*d* of the first barrier wall 622-1 and the second surface 624*b* of the linking part 624.

The fourth surface 622-6*d* of the sixth barrier wall 622-6 is separated from the fourth surface 622-2*d* of the second barrier wall 622-2. The fourth surface 622-6*d* of the sixth barrier wall 622-6 and the fourth surface 622-2*d* of the second barrier wall 622-2 are separated only by an amount corresponding to the interposing linking part 624. That is, the gap 628 includes a space that is formed by the fourth surface 622-6*d* of the sixth barrier wall 622-6, the fourth surface 622-2*d* of the second barrier wall 622-2 and the second surface 624*b* of the linking part 624.

The fourth surface 622-6*d* of the sixth barrier wall 622-6 is separated from the fourth surface 622-3*d* of the third barrier wall 622-3. The fourth surface 622-6*d* of the sixth barrier wall 622-6 and the fourth surface 622-3*d* of the third barrier wall 622-3 are separated only by an amount corresponding to the interposing linking part 624. That is, the gap 628 includes a space that is formed by the fourth surface 622-6*d* of the sixth barrier wall 622-6, the fourth surface 622-3*d* of the third barrier wall 622-3 and the second surface 624*b* of the linking part 624.

The fourth surface 622-6*d* of the sixth barrier wall 622-6 is separated from the fourth surface 622-5*d* of the fifth barrier wall 622-5. The fourth surface 622-6*d* of the sixth barrier wall 622-6 and the fourth surface 622-5*d* of the fifth barrier wall 622-5 are separated only by an amount corresponding to the interposing linking part 624. That is, the gap 628 includes a space that is formed by the fourth surface 622-6*d* of the sixth barrier wall 622-6, the fourth surface 622-5*d* of the fifth barrier wall 622-5 and the second surface 624*b* of the linking part 624.

The fourth surface 622-6*d* of the sixth barrier wall 622-6 is separated from the fourth surface 622-7*d* of the seventh barrier wall 622-7. The fourth surface 622-6*d* of the sixth barrier wall 622-6 and the fourth surface 622-7*d* of the seventh barrier wall 622-7 are separated only by an amount corresponding to the interposing linking part 624. That is, the gap 628 includes a space that is formed by the fourth surface 622-6*d* of the sixth barrier wall 622-6, the fourth surface 622-7*d* of the seventh barrier wall 622-7 and the second surface 624*b* of the linking part 624.

The fourth surface 622-6*d* of the sixth barrier wall 622-6 is separated from a fourth surface 622-9*d* of the ninth barrier wall 622-9. The fourth surface 622-6*d* of the sixth barrier wall 622-6 and the fourth surface 622-9*d* of the ninth barrier wall 622-9 are separated only by an amount corresponding to the interposing linking part 624. That is, the gap 628 includes a space that is formed by the fourth surface 622-6*d* of the sixth barrier wall 622-6, the fourth surface 622-9*d* of the ninth barrier wall 622-9 and the second surface 624*b* of the linking part 624.

The fourth surface 622-6*d* of the sixth barrier wall 622-6 is separated from a fourth surface 622-10*d* of the tenth barrier wall 622-10. The fourth surface 622-6*d* of the sixth barrier wall 622-6 and the fourth surface 622-10*d* of the tenth barrier wall 622-10 are separated only by an amount corresponding to the interposing linking part 624. That is, the gap 628 includes a space that is formed by the fourth surface 622-6*d* of the sixth barrier wall 622-6, the fourth surface 622-10*d* of the tenth barrier wall 622-10 and the second surface 624*b* of the linking part 624.

The fourth surface 622-6*d* of the sixth barrier wall 622-6 is separated from a fourth surface 622-11*d* of the eleventh barrier wall 622-11. The fourth surface 622-6*d* of the sixth barrier wall 622-6 and the fourth surface 622-11*d* of the eleventh barrier wall 622-11 are separated only by an amount corresponding to the interposing linking part 624. That is, the gap 628 includes a space that is formed by the fourth surface 622-6*d* of the sixth barrier wall 622-6, the fourth surface 622-11*d* of the eleventh barrier wall 622-11 and the second surface 624*b* of the linking part 624.

The sixth barrier wall 622-6 forms the partition 621-6 in a condition where a gap 628 is formed between the sixth barrier wall 622-6 and each of the first barrier wall 622-1, second barrier wall 622-2, the third barrier wall 622-3, the fifth barrier wall 622-5, the seventh barrier wall 622-7, the ninth barrier wall 622-9, the tenth barrier wall 622-10, and the eleventh barrier wall 622-11.

In this way, the gap 628 is a space that is formed between a barrier wall and another barrier wall. The gap 628 is a space that is surrounded by the barrier wall(s) 622 and the linking part 624.

The reinforcing part 626 is a member that reinforces a mechanical strength of the partitioned member 620. The reinforcing part 626 is a member that forms an outer edge of the partitioned member 620. The reinforcing part 626 is connected to the barrier wall, of the barrier walls 622 that constitute the partitioned member 620, that is positioned on the outermost circumference. The reinforcing part 626 extends along the barrier wall at the outermost circumference. As an example, the reinforcing part 626 extends along the entire circumference of the partitioned member 620. In FIG. 1, the reinforcing part 626 is connected to the first barrier wall 622-1, the second barrier wall 622-2, the third barrier wall 622-3, the fourth barrier wall 622-4, the fifth barrier wall 622-5, the eighth barrier wall 622-8, the ninth barrier wall 622-9, the twelfth barrier wall 622-12, the thirteenth barrier wall 622-13, the sixteen barrier wall 622-16, the seventeenth barrier wall 622-17, the twentieth barrier wall 622-20, the twenty first barrier wall 622-21, the twenty second barrier wall 622-22, the twenty third barrier wall 622-23 and the twenty fourth barrier wall 622-24. Note that the reinforcing part 626 may be arranged, for example, along one long or short side of the partitioned member 620, which has a rectangular geometry, rather than the entire circumference of the partitioned member 620. In this way, the mechanical strength of the outer edge portion of the partitioned member 620 is reinforced by the reinforcing part 626.

The reinforcing part 626 is also a linking member that links the first barrier wall 622-1, the second barrier wall 622-2, the third barrier wall 622-3, the fourth barrier wall 622-4, the fifth barrier wall 622-5, the eighth barrier wall 622-8, the ninth barrier wall 622-9, the twelfth barrier wall 622-12, the thirteenth barrier wall 622-13, the sixteen barrier wall 622-16, the seventeenth barrier wall 622-17, the twentieth barrier wall 622-20, the twenty first barrier wall 622-21, the twenty second barrier wall 622-22, the twenty third barrier wall 622-23 and the twenty fourth barrier wall 622-24. The reinforcing part 626 serves as a linking part that links the barrier walls 622.

The reinforcing part 626 is also a grasping member in the partitioned member 620. The reinforcing part 626 serves as a grasping part when the partitioned member 620 is grasped.

Note that the partitioned member 620 may be configured not to have the reinforcing part 626.

The partitioned member 620 is made from a resin, for example. As an example, the partitioned member 620 is made of a thermally reversible resin. The partitioned member 620 is a member having translucency, for example. As an example, the partitioned member 620 is a transparent member. Examples of resins used as the partitioned member 620 include acrylic resins such as poly methyl methacrylate resin and the like, polycarbonate (PC), cycloolefin copolymers (COC), polystyrene (PS) and the like The board 630 is a plate-like member. The board 630 has a first surface 630*a* and the second surface 630*b*. The first surface 630*a* of the board 630 is a surface that is parallel to the xy plane. In order to ensure a desired flatness, the first surface 630*a* of the board 630 is polished to an accuracy of several microns, for example.

The second surface 630*b* of the board 630 is a surface that is parallel to the xy plane. The second surface 630*b* of the board 630 is formed at a different position in the z axis direction than the first surface 630*a* of the board 630. The second surface 630*b* of the board 630 is parallel to the first surface 630*a* of the board 630. When the board 630 is joined with the partitioned member 620, the first surface 630*a* of the board 630 is positioned at more z plus side than the second surface 630*b* of the board 630. In order to ensure a desired flatness, the second surface 630*b* of the board 630 is polished to an accuracy of several microns, for example. When the plate 60 is formed by joining the partitioned member 620 with the board 630, the second surface 630*b* of the board 630 is a surface that is substantially parallel to the first surface 620*a* of the partitioned member 620.

The board 630 is made of a resin, for example. As an example, the board 630 is made of a thermally reversible resin. The board 630 is member having translucency, for example. As an example, the board 630 is a transparent member. Examples of resins used as the board 630 include acrylic resins such as poly methyl methacrylate resins and the like, polycarbonate (PC), cycloolefin copolymers (COC), and polystyrene (PS).

The board 630 is joined with the partitioned member 620. As an example, the first surface 630*a* of the board 630 is joined with the second surface 620*b* of the partitioned member 620. As an example, the first surface 630*a* of the board 630 is joined with the second surface 620*b* of the partitioned member 620 so as to entirely cover the second surface 620*b* of the partitioned member 620. The second surface 620*b* of the partitioned member 620 and the first surface 630*a* of the board 630 are joined in a condition where the partitions 621 that are formed in the partitioned member 620 is closed from the second surface 620*b* side of the partitioned member 620 by the first surface 630*a* of the board 630.

A welded joint is one example of a method for joining the partitioned member 620 and the board 630. In this case, the partitioned member 620 and the board 630 are made of thermally reversible resin. The partitioned member 620 and the board 630 are joined together by heating a joining location of the partitioned member 620 and a joining location of the board 630 to a melting temperature and then applying pressure. When the partitioned member 620 and the board 630 are joined by welding, the elution of undesirable chemical compounds can be suppressed more, compared to the case where the partitioned member 620 and the board 630 are joined using an adhesive. When the partitioned member 620 and the board 630 are joined by the welding, the stability of the joint can be improved more, compared to the case where the partitioned member 620 and the board 630 are joined by an adhesive. The partitioned member 620 is welded to the board 630 at the entire second surface 620*b* of the partitioned member 620. That is, the second surface 620*b* of the partitioned member 620 is welded to the first surface 630*a* of the board 630 at the entire second surfaces 622*b* of the barrier walls 622 that constitute wells 610. Welding at the entire second surfaces 622*b* of the barrier walls 622 forms, in the plate 60, a sealing structure that prevents a leakage of a liquid sample stored in the wells 610.

For example, an ultrasonic welding can be used for the welded joint of the partitioned member 620 and the board 630. Note that a laser welding, a vibration welding and the like may also be used for the welded joint of the partitioned member 620 and the board 630.

When the partitioned member 620 and the board 630 are joined by the welding, it is preferable that the melting temperature of the material used for the partitioned member 620 be same as the melting temperature of the material used for the board 630. Therefore, it is preferable that the material used for the partitioned member 620 be same as the material used for the board 630.

As an example, poly methyl methacrylate resin may be used as both of the material for the partitioned member 620 and the material for the board 630.

As another example, poly carbonate (PC) may be used as both of the material for the partitioned member 620 and the material for the board 630.

As another example, cycloolefin copolymer (COC) may be used as both of the material for the partitioned member 620 and the material for the board 630.

As another example, polystyrene (PS) may be used as both of the material for the partitioned member 620 and the material for the board 630.

When the partitioned member 620 and the board 630 are joined by the welding, it is preferable that the melting temperature of the material used for the partitioned member 620 be close to the melting temperature of the material used for the board 630.

As an example, poly methyl methacrylate resin may be used as the material for the partitioned member 620 and polycarbonate (PC) may be used as the material for the board 630.

As another example, polycarbonate (PC) may be used as the material for the partitioned member 620 and poly methyl methacrylate resin may be used as the material for the board 630.

The plate 60 has the wells 610 that are formed by the barrier walls 622 of the partitioned member 620 and the first surface 630*a* of the board 630. The first surface 630*a* of the board 630 forms bottoms of the wells 610. The well 610 is allowed to store a liquid sample and the like, for example.

The plate 60 includes, as the wells 610, a first well 610-1, a second well 610-2, a third well 610-3, a fourth well 610-4, a fifth well 610-5, a sixth well 610-6, a seventh well 610-7, an eighth well 610-8, a ninth well 610-9, a tenth well 610-10, an eleventh well 610-11, a twelfth well 610-12, a thirteenth well 610-13, a fourteenth well 610-14, a fifteenth well 610-15, a sixteenth well 610-16, a seventeenth well 610-17, an eighteenth well 610-18, a nineteenth well 610-19, a twentieth well 610-20, a twenty first well 610-21, a twenty second well 610-22, a twenty third well 610-23 and a twenty fourth well 610-24.

The first well 610-1 is formed by the first barrier wall 622-1 and the board 630. As an example, the first well 610-1 is formed by a third surface 622-1*c* of the first barrier wall 622-1 and the first surface 630*a* of the board 630.

The second well 610-2 is formed by the second barrier wall 622-2 and the board 630. As an example, the second well 610-2 is formed by a third surface 622-2c of the second barrier wall 622-2 and the first surface 630a of the board 630.

The third well 610-3 is formed by the third barrier wall 622-3 and the board 630. As an example, the third well 610-3 is formed by a third surface 622-3c of the third barrier wall 622-3 and the first surface 630a of the board 630.

The fourth well 610-4 is formed by the fourth barrier wall 622-4 and the board 630. As an example, the fourth well 610-4 is formed by a third surface 622-4c of the fourth barrier wall 622-4 and the first surface 630a of the board 630.

The fifth well 610-5 is formed by the fifth barrier wall 622-5 and the board 630. As an example, the fifth well 610-5 is formed by a third surface 622-5c of the fifth barrier wall 622-5 and the first surface 630a of the board 630.

The sixth well 610-6 is formed by the sixth barrier wall 622-6 and the board 630. As an example, the sixth well 610-6 is formed by a third surface 622-6c of the sixth barrier wall 622-6 and the first surface 630a of the board 630.

The seventh well 610-7 is formed by the seventh barrier wall 622-7 and the board 630. As an example, the seventh well 610-7 is formed by a third surface 622-7c of the seventh barrier wall 622-7 and the first surface 630a of the board 630.

The eighth well 610-8 is formed by the eighth barrier wall 622-8 and the board 630. As an example, the eighth well 610-8 is formed by a third surface 622-8c of the eights barrier wall 622-8 and the first surface 630a of the board 630.

The ninth well 610-9 is formed by the ninth barrier wall 622-9 and the board 630. As an example, the ninth well 610-9 is formed by a third surface 622-9c of the ninth barrier wall 622-9 and the first surface 630a of the board 630.

The tenth well 610-10 is formed by the tenth barrier wall 622-10 and the board 630. As an example, the tenth well 610-10 is formed by a third surface 622-10c of the tenth barrier wall 622-10 and the first surface 630a of the board 630.

The eleventh well 610-11 is formed by the eleventh barrier wall 622-11 and the board 630. As an example, the eleventh well 610-11 is formed by a third surface 622-11c of the eleventh barrier wall 622-11 and the first surface 630a of the board 630.

The twelfth well 610-12 is formed by the twelfth barrier wall 622-12 and the board 630. As an example, the twelfth well 610-12 is formed by a third surface 622-12c of the twelfth barrier wall 622-12 and the first surface 630a of the board 630.

The thirteenth well 610-13 is formed by the thirteenth barrier wall 622-13 and the board 630. As an example, the thirteenth well 610-13 is formed by a third surface 622-13c of the thirteenth barrier wall 622-13 and the first surface 630a of the board 630.

The fourteenth well 610-14 is formed by the fourteenth barrier wall 622-14 and the board 630. As an example, the fourteenth well 610-14 is formed by a third surface 622-14c of the fourteenth barrier wall 622-14 and the first surface 630a of the board 630.

The fifteenth well 610-15 is formed by the fifteenth barrier wall 622-15 and the board 630. As an example, the fifteenth well 610-15 is formed by a third surface 622-15c of the fifteenth barrier wall 622-15 and the first surface 630a of the board 630.

The sixteenth well 610-16 is formed by the sixteenth barrier wall 622-16 and the board 630. As an example, the sixteenth well 610-16 is formed by a third surface 622-16c of the sixteenth barrier wall 622-16 and the first surface 630a of the board 630.

The seventeenth well 610-17 is formed by the seventeenth barrier wall 622-17 and the board 630. As an example, the seventeenth well 610-17 is formed by a third surface 622-17c of the seventeenth barrier wall 622-17 and the first surface 630a of the board 630.

The eighteenth well 610-18 is formed by the eighteenth barrier wall 622-18 and the board 630. As an example, the eighteenth well 610-18 is formed by a third surface 622-18c of the eighteenth barrier wall 622-18 and the first surface 630a of the board 630.

The nineteenth well 610-19 is formed by the nineteenth barrier wall 622-19 and the board 630. As an example, the nineteenth well 610-19 is formed by a third surface 622-19c of the nineteenth barrier wall 622-19 and the first surface 630a of the board 630.

The twentieth well 610-20 is formed by the twentieth barrier wall 622-20 and the board 630. As an example, the twentieth well 610-20 is formed by a third surface 622-20c of the twentieth barrier wall 622-20 and the first surface 630a of the board 630.

The twenty first well 610-21 is formed by the twenty first barrier wall 622-21 and the board 630. As an example, the twenty first well 610-21 is formed by a third surface 622-21c of the twenty first barrier wall 622-21 and the first surface 630a of the board 630.

The twenty second well 610-22 is formed by the twenty second barrier wall 622-22 and the board 630. As an example, the twenty second well 610-22 is formed by a third surface 622-22c of the twenty second barrier wall 622-22 and the first surface 630a of the board 630.

The twenty third well 610-23 is formed by the twenty third barrier wall 622-23 and the board 630. As an example, the twenty third well 610-23 is formed by a third surface 622-23c of the twenty third barrier wall 622-23 and the first surface 630a of the board 630.

The twenty fourth well 610-24 is formed by the fourth first barrier wall 622-24 and the board 630. As an example, the twenty fourth well 610-24 is formed by a third surface 622-24c of the twenty fourth barrier wall 622-24 and the first surface 630a of the board 630.

FIG. 2 is a cross sectional view of the plate 60. FIG. 2 illustrates a cross section of the plate 60 that is cut along a cut line A-A in FIG. 1. The plate 60 has the wells 610 that are formed by the barrier walls 622 of the partitioned member 620 and the board 630. FIG. 2 illustrates four wells—the first well 610-1 that is formed by the first barrier wall 622-1 of the partitioned member 620 and the first surface 630a of the board 630, the second well 610-2 that is formed by the second barrier wall 622-2 of the partitioned member 620 and the first surface 630a of the board 630, the third well 610-3 that is formed by the third barrier wall 622-3 of the partitioned member 620 and the first surface 630a of the board 630, and the fourth well 610-4 that is formed by the fourth barrier wall 622-4 of the partitioned member 620 and the first surface 630a of the board 630. The barrier walls 622 are linked by the linking part 624. In FIG. 2, the linking part 624 is arranged between the first barrier wall 622-1 and the second barrier wall 622-2, between the second barrier wall 622-2 and the third barrier wall 622-3, and between the third barrier wall 622-3 and the fourth barrier wall 622-4. As an example, the barrier walls 622 are linked by the linking part 624 at an upper end 622e on the z plus direction side of the barrier wall 622, that is, at the first surface 620a side of the partitioned member 620. The barrier walls 622 are separated below (at a z minus direction side of) the linking part 624. The partitioned member 620 has the gap 628 below (at the z minus direction side of) the linking part 624. In the partitioned member 620, the gap 628 is a space that is surrounded by the barrier walls 622 and the linking part 624. In the plate 60, the gap 628 is a space that is surrounded by the barrier walls 622, the linking part 624, and the board 630.

The degree of freedom for a relative position of the well 610 on the second surface 620b side of the partitioned member 620 when the gap 628 is present is higher than that when the gap 628 is not present. That is, as illustrated in FIG. 2, the partitioned member 620 has a degree of freedom to displace two adjacent wells (for example, the first well 610-1 and the second well 610-2) away from or closer to one another in directions of arrows A with the linking part 624 arranged between the adjacent barrier walls (for example, the first barrier wall 622-1 and the second barrier wall 622-2) as a fulcrum.

Rigidity of the partitioned member 620 at which the gap 628 is formed is lower than that of the partitioned member 620 at which the gap 628 is not formed. Therefore, even if the partitioned member 620 is pressed against the board 630 when the partitioned member 620 and the board 630 are joined, the pressing force from the partitioned member 620 does not easily transfer to the board 630 because the partitioned member 620 itself deforms. As a result, occurrence of deformation (for example, deflection or distortion) of the board 630 can be suppressed. Thus, a condition where the board 630 does not deform can be maintained even after the partitioned member 620 and the board 630 are joined. By this, it is possible to perform optical measurement of a sample in the wells 610 with good accuracy by using the plate 60.

The rigidity of the partitioned member 620 changes depending on a depth (a distance in the z direction) and a width (a distance in the y direction) of the gap 628. For example, because the linking part 624 is formed thinner as the gap 628 becomes deeper, the rigidity of the partitioned member 620 decreases. Because the barrier walls 622 are separated more as the width of the gap 628 gets wider, the rigidity of the partitioned member 620 decreases.

In this way, the plate is configured using a partitioned member that forms a partition in a condition where a gap is formed between a barrier wall and another barrier wall, and thus deterioration of surface accuracy of the plate can be suppressed. When the optical measurement is performed on the sample on the plate, it is possible to perform the optical measurement with good accuracy.

FIG. 3 is a drawing conceptually illustrating a structure of a screening apparatus 10 in one embodiment of the present invention. Note that an X axis, a Y axis and a Z axis are defined for the convenience of description. The X axis, the Y axis and the Z axis defines intersecting coordinates. Each of the X axis direction and the Y axis direction is a horizontal direction. The Z axis direction is a vertical direction. The screening apparatus 10 is provided with a dispensing apparatus 20, a cleaning and drying apparatus 30, a detecting apparatus 40 and a transporting apparatus 50. The dispensing apparatus 20, the cleaning and drying apparatus 30 and the detecting apparatus 40 are arranged in the X axis direction in an order of the dispensing apparatus 20, the cleaning and drying apparatus 30 and the detecting apparatus 40.

The dispensing apparatus 20 is an apparatus for performing the dispensing to the plate 60. The dispensing apparatus 20 is provided with a transporting device 210, a dispensing device 220 and a controlling device 230.

The transporting device 210 is provided with a plate supporting part 211 and a driving part 212. The plate supporting part 211 is a member for supporting the plate 60. The plate supporting part 211 is a placement stage on which the plate 60 is placed, for example.

The driving part 212 moves the plate supporting part 211. As an example, the driving part 212 moves the plate supporting part 211 between a placement position P1 and a delivery position P3. As an example, the driving part 212 moves the plate supporting part 211 in the X axis between the placement position P1 and the delivery position P3 via a dispensing position P2. The transporting device 210 is a transport line for transporting the plate 60.

The dispensing device 220 is provided with the dispensing part 221. The dispensing part 221 is configured to have nozzles, for example. The dispensing device 220 dispenses a specimen from the dispensing part 221. A plurality of nozzles whose number is same as the number of the wells formed in the plate 60 are arranged in the dispensing part 221 in an arrangement manner that is same as an arrangement manner for the wells formed in the plate 60. When the plate 60 in which 24 wells are formed in a six-by-four matrix manner is used, the dispensing part 221 is configured to have 24 nozzles that are arranged in a six-by-four matrix manner. By this, the dispensing device 220 is allowed to perform the dispensing to all wells in one plate 60 together.

Note that a structure of a dispensing device is not limited to this structure. When a dispensing device having nozzles that are arranged in a liner manner is used, a method of performing the dispensing to the wells in one row together and then performing the dispensing to next row in order may be used. When a dispensing device having only one nozzle is used, a method of performing the dispensing to one well one by one in order may be used.

The controlling device 230 controls an operation of each of the transporting device 210 and the dispensing device 220.

The plate 60 is arranged on the placement position P1. As an example, the plate 60 is placed on the plate supporting part 211 that is placed at the placement position P1 by a not-illustrated robot, for example. By this, the plate 60 is supported by the plate supporting part 211 at the placement position P1. The plate 60 is supported by the plate supporting part 211 in a condition where openings of the wells face upwardly (the Z axis plus direction). The plate 60 in which the openings of the wells face upwardly (the Z axis plus direction) may be referred to as the plate 60 in a horizontal condition in some cases. In the horizontal condition, the x axis (see FIG. 1 and FIG. 2) of the plate 60 coincides with the Y axis illustrated in FIG. 3, the y axis (see FIG. 1 and FIG. 2) of the plate 60 coincides with the X axis illustrated in FIG. 3, and the z axis (see FIG. 1 and FIG. 2) of the plate 60 coincides with the Z axis illustrated in FIG. 3. The plate 60 may be also referred to as the plate 60 in the horizontal condition, when a first surface of a below described biochip is parallel to an XY plane illustrated in FIG. 3.

After the plate 60 is supported by the plate supporting part 211 at the placement position P1, the controlling device 230 controls the driving part 212 to move the plate 60 from the placement position P1 to the dispensing position P2 and then to stop the plate 60 at the dispensing position P2. The driving part 212 moves the plate supporting part 211 to move the plate 60 from the placement position P1 to the dispensing position P2 and then to stop the plate 60 at the dispensing position P2. As an example, the driving part 212 moves the plate supporting part 211 to move the plate 60 from the placement position P1 to the dispensing position P2 in the X axis direction while keeping the plate 60 in the horizontal condition and then to stop the plate 60 at the dispensing position P2 while keeping the plate 60 in the horizontal condition. By this, the plate 60 is located at the dispensing position P2 in the horizontal condition.

After the plate 60 that is supported by the plate supporting part 211 stops at the dispensing position P2, the controlling device 230 controls the dispensing device 220 to perform the dispensing to the plate 60. The dispensing device 220 dispenses the specimen from the dispensing part 221. By this, the specimen is dispensed to the wells in the plate 60.

After the specimen is dispensed to the wells, the controlling device 230 controls the driving part 212 to move the plate 60 from the dispensing position P2 to the delivery position P3 and then to stop the plate 60 at the delivery position P3. The driving part 212 moves the plate supporting part 211 to move the plate 60 from the dispensing position P2 to the delivery position P3 and then to stop the plate 60 at the delivery position P3. As an example, the driving part 212 moves the plate supporting part to move the plate 60 from the dispensing position P2 to the delivery position P3 in the X axis direction while keeping the plate 60 in the horizontal condition and then to stop the plate 60 at the delivery position P3 while keeping the plate 60 in the horizontal condition. By this, the plate 60 is located at the delivery position P3 in the horizontal condition.

In this way, the plate 60 moves in the X axis direction from the placement position P1 to the delivery position P3 via the dispensing position P2 while the plate 60 is supported in the horizontal condition by the plate supporting part 211.

The plate 60 that has been supported by the plate supporting part 211 at the delivery position P3 is transported to the cleaning and drying apparatus 30 by the transporting apparatus 50. The plate supporting part 211 delivers the supported plate 60 to the transporting apparatus 50 at the delivery position P3.

The controlling device 230 may control the driving part 212 to swing the plate supporting part 211 after the specimen is dispensed to the plate 60 by the dispensing device 220 and before the plate 60 is delivered to the transporting apparatus 50. The driving part 212 swings the plate supporting part 211 after the specimen is dispensed to the plate 60 by the dispensing device 220 and before the plate 60 is delivered to the transporting apparatus 50. As an example, the driving part 212 swings the plate supporting part 211 around the dispensing position P2. The biochip is supported at a bottom of each well in the plate 60. The biochip is provided with a base material and biomolecules. The base material is a plate member, for example. The biomolecule (a probe) is able to react specifically to a target molecule (a target, hereinafter, it is referred to as a "target") that may be included in the specimen. The biomolecules are fixed to a surface (a first surface) of the base material. The biochip may be referred to as a microarray in some cases. The biochip is supported by the plate 60 (the bottom of the well) via a surface (a second surface) that is opposite to the surface (the first surface) to which the biomolecules are fixed. As an example, the biochip and the plate 60 (the bottom of the well) are fixed by bonding them with an adhesive material, a double-stick tape or the like. The swinging of the plate 60 by the driving part 212 results in an acceleration of the reaction between the biomolecules fixed to the biochip and the target in the specimen.

When the dispensing apparatus 20 is provided with a heating device that applies heat to the plate 60 supported by the plate supporting part 211, the controlling device 230 may control the heating device to heat the plate supporting part 211 after the specimen is dispensed to the plate 60 by the dispensing device 220 and before the plate 60 is delivered to the transporting apparatus 50. The heating device heats the plate 60 to a temperature at which the biomolecules fixed to the biochip and the target in the specimen react to each other smoothly.

The cleaning and drying apparatus 30 is an apparatus for performing a cleaning process and a drying process on the dispensed plate 60 for a subsequent detecting process by the detecting apparatus 40. The cleaning and drying apparatus 30 is provided with a cleaning device 310, a drying device 320, a transporting device 330, a controlling device 340, a housing device 350, and a waste solution collecting device 360. A structure of the cleaning and drying apparatus 30 will be described later in detail.

The detecting apparatus 40 is an apparatus for detecting affinity between the biomolecules and the target using the plate on which the cleaning process and the drying process has been performed. The detecting apparatus 40 is provided with an imaging device 410 and a placing device 420.

The imaging device 410 includes a light source, an optical system and an imaging element. The light source illuminates the biochip on the plate 60. The optical system forms an image of the light from the biochip on the imaging element. The imaging device generates electrical charge depending on the light by which the optical system forms the image to generate image data of the biochip. The placing device 420 is a device on which the plate 60 is placed. The placing device 420 is a stage (a placement stage), for example.

The plate 60 is transported from the cleaning and drying apparatus 30 to the detecting apparatus 40 by the transporting apparatus 50. As an example, the plate 60 is placed on the placing device 420 of the detecting apparatus 40 by the transporting apparatus 50. The plate 60 is placed on the placing device 420 in the horizontal condition. The imaging device 410 images the plate 60 that has been placed on the placing device 420 in the horizontal condition to generate the image data of the biochip.

The detecting apparatus 40 may detect the affinity between the biomolecules and the target by imaging fluorescence generated from the biomolecules on the biochip with the imaging device 410, for example. The biomolecules on the biochip generates the fluorescence only at positions at which the target in the specimen has reacted specifically to the biomolecule, when the light from the light source is irradiated. Thus, a fluorescence image based on the image data that is obtained by imaging the biochip is an image in which positions corresponding to the biomolecules that react the target are brighten by the fluorescence. It is possible to detect which biomolecules on the biochip the target in the specimen has an affinity for by image analyzing the fluorescence image (positions and the brightness of the fluorescence). For example, the detecting apparatus 40 detects the fluorescence that is obtained from the biochip, as the detection of the affinity.

FIG. 4 is a drawing conceptually illustrating the structure of the cleaning and drying apparatus 30. The cleaning and drying apparatus 30 is provided with the cleaning device 310, the drying device 320, the transporting device 330, the controlling device 340, the housing device 350 and the waste solution collecting device 360.

The cleaning device 310 is a device for cleaning the plate 60. The cleaning device 310 performs the cleaning process on the plate 60.

The cleaning device 310 is provided with a cleaning solution supplying part 311 and cleaning solution nozzles 312. The cleaning solution nozzles 312 include a first cleaning solution nozzle 312a, a second cleaning solution nozzle 312b, a third cleaning solution nozzle 312c, a fourth cleaning solution nozzle 312d, a fifth cleaning solution nozzle 312e, a sixth cleaning solution nozzle 312f, a seventh cleaning solution nozzle 312g, an eighth cleaning solution nozzle 312h, a ninth cleaning solution nozzle 312i, a tenth cleaning solution nozzle 312j, a eleventh cleaning solution nozzle 312k, a twelfth cleaning solution nozzle 312l, a thirteenth cleaning solution nozzle 312m, a fourteenth cleaning solution nozzle 312n, a fifteenth cleaning solution nozzle 312o, a sixteenth cleaning solution nozzle 312p, a seventeenth cleaning solution nozzle 312q, a eighteenth cleaning solution nozzle 312r, a nineteenth cleaning solution nozzle 312s, a twentieth cleaning solution nozzle 312t, a twenty first cleaning solution nozzle 312u, a twenty second cleaning solution nozzle 312v, a twenty third cleaning solution nozzle 312w, a twenty fourth cleaning solution nozzle 312x, a twenty fifth cleaning solution nozzle 312y, a twenty sixth cleaning solution nozzle 312z, a twenty seventh cleaning solution nozzle 312A, a twenty eighth cleaning solution nozzle 312B, a twenty ninth cleaning solution nozzle 312C, a thirtieth cleaning solution nozzle 312D, a thirty first cleaning solution nozzle 312E, a thirty second cleaning solution nozzle 312F, a thirty third cleaning solution nozzle 312G, a thirty fourth cleaning solution nozzle 312H, a thirty fifth cleaning solution nozzle 312I, a thirty sixth cleaning solution nozzle 312J, a thirty seventh cleaning solution nozzle 312K, a thirty eighth cleaning solution nozzle 312L, a thirty ninth cleaning solution nozzle 312M, a fortieth cleaning solution nozzle 312N, a forty first cleaning solution nozzle 312O and a forty second cleaning solution nozzle 312P.

The cleaning solution supplying part 311 has a body 311a and cleaning solution supplying pipes 311b.

The body 311a includes a container 311c for storing cleaning solution.

The cleaning solution supplying pipes 311b include a first cleaning solution supplying pipe 311d, a second cleaning solution supplying pipe 311e, a third cleaning solution supplying pipe 311f, a fourth cleaning solution supplying pipe 311g, a fifth cleaning solution supplying pipe 311h, a sixth cleaning solution supplying pipe 311i and a seventh cleaning solution supplying pipe 311j.

The first cleaning solution supplying pipe 311d is connected to the container 311c. The first cleaning solution supplying pipe 311d is a pipe for supplying the cleaning solution stored in the container 311c to each of the first cleaning solution nozzle 312a, the second cleaning solution nozzle 312b, the third cleaning solution nozzle 312c, the fourth cleaning solution nozzle 312d, the fifth cleaning solution nozzle 312e and the sixth cleaning solution nozzle 312f. The first cleaning solution supplying pipe 311d is configured to extend toward a Y axis plus direction from the body 311a.

The second cleaning solution supplying pipe 311e is connected to the container 311c. The second cleaning solution supplying pipe 311e is a pipe for supplying the cleaning solution stored in the container 311c to each of the seventh cleaning solution nozzle 312g, the eighth cleaning solution nozzle 312h, the ninth cleaning solution nozzle 312i, the tenth cleaning solution nozzle 312j, the eleventh cleaning solution nozzle 312k and the twelfth cleaning solution nozzle 312l. The second cleaning solution supplying pipe 311e is configured to extend toward the Y axis plus direction from the body 311a.

The third cleaning solution supplying pipe 311f is connected to the container 311c. The third cleaning solution supplying pipe 311f is a pipe for supplying the cleaning solution stored in the container 311c to each of the thirteenth cleaning solution nozzle 312m, the fourteenth cleaning solution nozzle 312n, the fifteenth cleaning solution nozzle 312o, the sixteenth cleaning solution nozzle 312p, the seventeenth cleaning solution nozzle 312q and the eighteenth cleaning solution nozzle 312r. The third cleaning solution supplying pipe 311f is configured to extend toward the Y axis plus direction from the body 311a.

The fourth cleaning solution supplying pipe 311g is connected to the container 311c. The fourth cleaning solution supplying pipe 311g is a pipe for supplying the cleaning solution stored in the container 311c to each of the nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x. The fourth cleaning solution supplying pipe 311g is configured to extend toward the Y axis plus direction from the body 311a.

The fifth cleaning solution supplying pipe 311h is connected to the container 311c. The fifth cleaning solution supplying pipe 311h is a pipe for supplying the cleaning solution stored in the container 311c to each of the twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D. The fifth cleaning solution supplying pipe 311h is configured to extend toward the Y axis plus direction from the body 311a.

The sixth cleaning solution supplying pipe 311i is connected to the container 311c. The sixth cleaning solution supplying pipe 311i is a pipe for supplying the cleaning solution stored in the container 311c to each of the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J. The sixth cleaning solution supplying pipe 311i is configured to extend toward the Y axis plus direction from the body 311a.

The seventh cleaning solution supplying pipe 311j is connected to the container 311c. The seventh cleaning solution supplying pipe 311j is a pipe for supplying the cleaning solution stored in the container 311c to each of the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P. The seventh cleaning solution supplying pipe 311j is configured to extend toward the Y axis plus direction from the body 311a.

The first cleaning solution supplying pipe 311d, the second cleaning solution supplying pipe 311e, the third cleaning solution supplying pipe 311f and the fourth cleaning solution supplying pipe 311g are arranged along the vertical direction. The first cleaning solution supplying pipe 311d, the second cleaning solution supplying pipe 311e, the third cleaning solution supplying pipe 311*f* and the fourth cleaning solution supplying pipe 311*g* are arranged along the Z axis direction.

The fifth cleaning solution supplying pipe 311*h*, the sixth cleaning solution supplying pipe 311*i* and the seventh cleaning solution supplying pipe 311*j* are arranged along the vertical direction. The fifth cleaning solution supplying pipe 311*h*, the sixth cleaning solution supplying pipe 311*i* and the seventh cleaning solution supplying pipe 311*j* are arranged along the Z axis direction.

Each of the first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e*, the sixth cleaning solution nozzle 312*f*, the seventh cleaning solution nozzle 312*g*, then eighth cleaning solution nozzle 312*h*, the ninth cleaning solution nozzle 312*i*, the tenth cleaning solution nozzle 312*j*, the eleventh cleaning solution nozzle 312*k*, the twelfth cleaning solution nozzle 312*l*, the thirteenth cleaning solution nozzle 312*m*, the fourteenth cleaning solution nozzle 312*n*, the fifteenth cleaning solution nozzle 312*o*, the sixteenth cleaning solution nozzle 312*p*, the seventeenth cleaning solution nozzle 312*q*, the eighteenth cleaning solution nozzle 312*r*, the nineteenth cleaning solution nozzle 312*s*, the twentieth cleaning solution nozzle 312*t*, the twenty first cleaning solution nozzle 312*u*, the twenty second cleaning solution nozzle 312*v*, the twenty third cleaning solution nozzle 312*w*, the twenty fourth cleaning solution nozzle 312*x*, the twenty fifth cleaning solution nozzle 312*y*, the twenty sixth cleaning solution nozzle 312*z*, the twenty seventh cleaning solution nozzle 312A, the twenty eighth cleaning solution nozzle 312B, the twenty ninth cleaning solution nozzle 312C, the thirtieth cleaning solution nozzle 312D, the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I, the thirty sixth cleaning solution nozzle 312J, the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P is a member for discharging the cleaning solution stored in the container 311*c*.

Each of the first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e* and the sixth cleaning solution nozzle 312*f* is connected to the first cleaning solution supplying pipe 311*d*. Each of the first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e* and the sixth cleaning solution nozzle 312*f* is arranged at more X axis minus direction side in the X axis direction than the twenty fifth cleaning solution nozzle 312*y* to the forty second cleaning solution nozzle 312P. The first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e* and the sixth cleaning solution nozzle 312*f* are arranged along the Y axis direction at the first cleaning solution supplying pipe 311*d*. Each of the first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e* and the sixth cleaning solution nozzle 312*f* is fixed to the first cleaning solution supplying pipe 311*d* in a condition where each nozzle faces toward the X axis plus direction, for example. By this, each of the first cleaning solution nozzle 312*a*, the second cleaning solution nozzle 312*b*, the third cleaning solution nozzle 312*c*, the fourth cleaning solution nozzle 312*d*, the fifth cleaning solution nozzle 312*e* and the sixth cleaning solution nozzle 312*f* is allowed to discharge the cleaning solution stored in the container 311*c* toward the X axis plus direction.

Each of the seventh cleaning solution nozzle 312*g*, the eighth cleaning solution nozzle 312*h*, the ninth cleaning solution nozzle 312*i*, the tenth cleaning solution nozzle 312*j*, the eleventh cleaning solution nozzle 312*k* and the twelfth cleaning solution nozzle 312*l* is connected to the second cleaning solution supplying pipe 311*e*. Each of the seventh cleaning solution nozzle 312*g*, then eighth cleaning solution nozzle 312*h*, the ninth cleaning solution nozzle 312*i*, the tenth cleaning solution nozzle 312*j*, the eleventh cleaning solution nozzle 312*k* and the twelfth cleaning solution nozzle 312*l* is arranged at more X axis minus direction side in the X axis direction than the twenty fifth cleaning solution nozzle 312*y* to the forty second cleaning solution nozzle 312P. The seventh cleaning solution nozzle 312*g*, the eighth cleaning solution nozzle 312*h*, the ninth cleaning solution nozzle 312*i*, the tenth cleaning solution nozzle 312*j*, the eleventh cleaning solution nozzle 312*k* and the twelfth cleaning solution nozzle 312*l* are arranged along the Y axis direction at the second cleaning solution supplying pipe 311*e*. Each of the seventh cleaning solution nozzle 312*g*, the eighth cleaning solution nozzle 312*h*, the ninth cleaning solution nozzle 312*i*, the tenth cleaning solution nozzle 312*j*, the eleventh cleaning solution nozzle 312*k* and the twelfth cleaning solution nozzle 312*l* is fixed to the second cleaning solution supplying pipe 311*e* in a condition where each nozzle faces toward the X axis plus direction, for example. By this, each of the seventh cleaning solution nozzle 312*g*, the eighth cleaning solution nozzle 312*h*, the ninth cleaning solution nozzle 312*i*, the tenth cleaning solution nozzle 312*j*, the eleventh cleaning solution nozzle 312*k* and the twelfth cleaning solution nozzle 312*l* is allowed to discharge the cleaning solution stored in the container 311*c* toward the X axis plus direction.

Each of the thirteenth cleaning solution nozzle 312*m*, the fourteenth cleaning solution nozzle 312*n*, the fifteenth cleaning solution nozzle 312*o*, the sixteenth cleaning solution nozzle 312*p*, the seventeenth cleaning solution nozzle 312*q* and the eighteenth cleaning solution nozzle 312*r* is connected to the third cleaning solution supplying pipe 311*f*. Each of the thirteenth cleaning solution nozzle 312*m*, the fourteenth cleaning solution nozzle 312*n*, the fifteenth cleaning solution nozzle 312*o*, the sixteenth cleaning solution nozzle 312*p*, the seventeenth cleaning solution nozzle 312*q* and the eighteenth cleaning solution nozzle 312*r* is arranged at more X axis minus direction side in the X axis direction than the twenty fifth cleaning solution nozzle 312*y* to the forty second cleaning solution nozzle 312P. The thirteenth cleaning solution nozzle 312*m*, the fourteenth cleaning solution nozzle 312*n*, the fifteenth cleaning solution nozzle 312*o*, the sixteenth cleaning solution nozzle 312*p*, the seventeenth cleaning solution nozzle 312*q* and the eighteenth cleaning solution nozzle 312*r* are arranged along the Y axis direction at the third cleaning solution supplying pipe 311*f*. Each of the thirteenth cleaning solution nozzle 312*m*, the fourteenth cleaning solution nozzle 312*n*, the fifteenth cleaning solution nozzle 312*o*, the sixteenth cleaning solution nozzle 312*p*, the seventeenth cleaning solution nozzle 312*q* and the eighteenth cleaning solution nozzle 312r is fixed to the third cleaning solution supplying pipe 311f in a condition where each nozzle faces toward the X axis plus direction, for example. By this, each of the thirteenth cleaning solution nozzle 312m, the fourteenth cleaning solution nozzle 312n, the fifteenth cleaning solution nozzle 312o, the sixteenth cleaning solution nozzle 312p, the seventeenth cleaning solution nozzle 312q and the eighteenth cleaning solution nozzle 312r is allowed to discharge the cleaning solution stored in the container 311c toward the X axis plus direction.

Each of the nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x is connected to the fourth cleaning solution supplying pipe 311g. Each of the nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x is arranged at more X axis minus direction side in the X axis direction than the twenty fifth cleaning solution nozzle 312y to the forty second cleaning solution nozzle 312P. The nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x are arranged along the Y axis direction at the fourth cleaning solution supplying pipe 311g. Each of the nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x is fixed to the fourth cleaning solution supplying pipe 311g in a condition where each nozzle faces toward the X axis plus direction, for example. By this, each of the nineteenth cleaning solution nozzle 312s, the twentieth cleaning solution nozzle 312t, the twenty first cleaning solution nozzle 312u, the twenty second cleaning solution nozzle 312v, the twenty third cleaning solution nozzle 312w and the twenty fourth cleaning solution nozzle 312x is allowed to discharge the cleaning solution stored in the container 311c toward the X axis plus direction.

Each of the twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D is connected to the fifth cleaning solution supplying pipe 311h. Each of the twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D is arranged at more X axis plus direction side in the X axis direction than the first cleaning solution nozzle 312a to the twenty fourth cleaning solution nozzle 312x. The twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D are arranged along the Y axis direction at the fifth cleaning solution supplying pipe 311h.

Each of the twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D is fixed to the fifth cleaning solution supplying pipe 311h in a condition where each nozzle faces toward the X axis minus direction, for example. By this, each of the twenty fifth cleaning solution nozzle 312y, the twenty sixth cleaning solution nozzle 312z, the twenty seventh cleaning solution nozzle 312A, the twenty eighth cleaning solution nozzle 312B, the twenty ninth cleaning solution nozzle 312C and the thirtieth cleaning solution nozzle 312D is allowed to discharge the cleaning solution stored in the container 311c toward the X axis minus direction.

Each of the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J is connected to the sixth cleaning solution supplying pipe 311i. Each of the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J is arranged at more X axis plus direction side in the X axis direction than the first cleaning solution nozzle 312a to the twenty fourth cleaning solution nozzle 312x. The thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J are arranged along the Y axis direction at the sixth cleaning solution supplying pipe 311i. Each of the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J is fixed to the sixth cleaning solution supplying pipe 311i in a condition where each nozzle faces toward the X axis minus direction, for example. By this, each of the thirty first cleaning solution nozzle 312E, the thirty second cleaning solution nozzle 312F, the thirty third cleaning solution nozzle 312G, the thirty fourth cleaning solution nozzle 312H, the thirty fifth cleaning solution nozzle 312I and the thirty sixth cleaning solution nozzle 312J is allowed to discharge the cleaning solution stored in the container 311c toward the X axis minus direction.

Each of the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P is connected to the seventh cleaning solution supplying pipe 311j. Each of the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P is arranged at more X axis plus direction side in the X axis direction than the first cleaning solution nozzle 312a to the twenty fourth cleaning solution nozzle 312x. The thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P are arranged along the Y axis direction at the seventh cleaning solution supplying pipe 311*j*. Each of the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P is fixed to the seventh cleaning solution supplying pipe 311*j* in a condition where each nozzle faces toward the X axis minus direction, for example. By this, each of the thirty seventh cleaning solution nozzle 312K, the thirty eighth cleaning solution nozzle 312L, the thirty ninth cleaning solution nozzle 312M, the fortieth cleaning solution nozzle 312N, the forty first cleaning solution nozzle 312O and the forty second cleaning solution nozzle 312P is allowed to discharge the cleaning solution stored in the container 311*c* toward the X axis minus direction.

In the cleaning device 310, a space between the first cleaning solution nozzle 312*a* to the twenty fourth cleaning solution nozzle 312*x* that are arranged at the X axis minus side and the twenty fifth cleaning solution nozzle 312*y* to the forty second cleaning solution nozzle 312P that are arranged at the X axis plus side is a cleaning position P6. The plate 60 is cleaned at the cleaning position P6. For example, the plate 60 is supported in an upright condition and cleaned at the cleaning position P6. The upright condition is a condition where the second surface 630*b* of the board 630 that constitutes the plate 60 is perpendicular to the XY plane. In the upright condition, the x axis of the plate 60 coincides with the Y axis illustrated in FIG. 3, the y axis of the plate 60 coincides with the Z axis illustrated in FIG. 3, and the z axis of the plate 60 coincides with the X axis illustrated in FIG. 3. The plate 60 is supported at the cleaning position P6 in a condition where the openings of the wells face toward the X axis minus direction. Alternatively, the plate 60 is supported at the cleaning position P6 in a condition where the openings of the wells face toward the X axis plus direction. The plate 60 may be referred to as the plate in the upright condition, when the first surface of the biochip is parallel to a YZ plane illustrated in FIG. 3. The cleaning solution nozzles 312 discharge the cleaning solution to the plate 60 that has been supported at the cleaning position P6 from both sides of the plate 60. As an example, the first cleaning solution nozzle 312*a* to the twenty fourth cleaning solution nozzle 312*x* discharge the cleaning solution from the X axis minus side of the plate 60 to the X axis plus direction, and the twenty fifth cleaning solution nozzle 312*y* to the forty second cleaning solution nozzle 312P discharge the cleaning solution from the X axis plus side of the plate 60 to the X axis minus direction. By this, both surfaces of the plate 60 at the X axis minus side and the X axis plus side, i.e., the entire plate including a portion at the X axis minus side and a portion at the X axis plus side can be cleaned effectively.

Note that the cleaning solution nozzles 312 may be configured to include only the first cleaning solution nozzle 312*a* to the twenty fourth cleaning solution nozzle 312*x* at the X axis minus side and not to include the twenty fifth cleaning solution nozzle 312*y* to the forty second cleaning solution nozzle 312P at the X axis plus side.

It is preferable that a purified water such as deionized water (DIW) be used as the cleaning solution, for example. When the cleaning solution is used after being heated to a temperature that does not change properties of the biomolecule on the biochip due to the heat, for example a temperature of 30 Celsius degree, a cleaning performance can be improved and the cleaning solution is easily vaporized at the subsequent drying process and thus a time for the drying process can be reduced. In this case, the cleaning solution supplying part 311 is configured to deionize usual tap water to generate the purified water and then to supply this as warm water to the cleaning solution nozzles 312 via the cleaning solution supplying pipes 311*b* after heating this to about 30 Celsius degree.

The cleaning solution nozzles 312 may be configured not only to directly discharge from the cleaning solution nozzles 312 the warm water supplied by the cleaning water supplying part 311 in this way but also to nebulize the warm water with inactive gas such as nitrogen and then inject it from the cleaning solution nozzles 312. By this, an amount of used water can be reduced. The reason why the inactive gas is used is for preventing oxidization of the biomolecule on the biochip.

The drying device 320 is a device for drying the plate 60. The drying device 320 performs the drying process on the plate 60.

The drying device 320 is provided with a blower part 321 and blower outlets 322. The blower outlets 322 includes a first blower outlet 322*a*, a second blower outlet 322*b*, a third blower outlet 322*c* and a fourth blower outlet 322*d*.

The bower part 321 has a body 321*a* and blower pipes 321*b*.

The body 321*a* supplies wind from the blower outlets 322 via the blower pipes 321*b*. The body 321*a* supplies inactive gas from the blower outlets 322, for example. One example of the inactive gas is nitrogen. Using the inactive gas results in the prevention of the oxidization of the biomolecule on the biochip. The body 321*a* may be configured to supply warm wind from the blower outlets 322. For example, the body 321*a* supplies the inactive gas whose temperature is adjusted to 30 to 40 Celsius degree from the blower outlets 322.

The blower pipes 321*b* include a first blower pipe 321*c*, a second blower pipe 321*d*, a third blower pipe 321*e* and a fourth blower pipe 321*f*.

The first blower outlet 321*c* is connected to the body 321*a*. The first blower outlet 321*c* is a pipe for supplying the wind from the body 321*a* to the first blower outlet 322*a*. The first blower pipe 321*c* is configured to extend from the body 321*a* toward the Y axis plus direction.

The second blower outlet 321*d* is connected to the body 321*a*. The second blower outlet 321*d* is a pipe for supplying the wind from the body 321*a* to the second blower outlet 322*b*. The second blower pipe 321*d* is configured to extend from the body 321*a* toward the Y axis plus direction.

The third blower outlet 321*e* is connected to the body 321*a*. The third blower outlet 321*e* is a pipe for supplying the wind from the body 321*a* to the third blower outlet 322*c*. The third blower pipe 321*e* is configured to extend from the body 321*a* toward the Y axis plus direction.

The fourth blower outlet 321*f* is connected to the body 321*a*. The fourth blower outlet 321*f* is a pipe for supplying the wind from the body 321*a* to the fourth blower outlet 322*d*. The fourth blower pipe 321*f* is configured to extend from the body 321*a* toward the Y axis plus direction.

The first blower outlet 322*a* is an opening along the Y axis direction. A length of the opening along the Y axis direction is longer than a length of a short side of the plate 60, for example. The first blower outlet 322*a* is connected to the first blower pipe 321*c*. The first blower outlet 322*a* is arranged at more X axis minus direction in the X axis direction than the third blower outlet 322c and the fourth blower outlet 322d. The first blower outlet 322a is connected to the first blower pipe 321c in a condition where the first blower outlet 322a faces toward the X axis plus direction, for example. By this, the first blower outlet 322a is allowed to blow the wind toward the X axis plus direction.

The second blower outlet 322b is an opening along the Y axis direction. A length of the opening along the Y axis direction is longer than the length of the short side of the plate 60, for example. The second blower outlet 322b is connected to the second blower pipe 321d. The second blower outlet 322b is arranged at more X axis minus direction in the X axis direction than the third blower outlet 322c and the fourth blower outlet 322d. The second blower outlet 322b is connected to the second blower pipe 321d in a condition where the second blower outlet 322b faces toward the X axis plus direction, for example. By this, the second blower outlet 322b is allowed to blow the wind toward the X axis plus direction.

The third blower outlet 322c is an opening along the Y axis direction. A length of the opening along the Y axis direction is longer than the length of the short side of the plate 60, for example. The third blower outlet 322c is connected to the third blower pipe 321e. The third blower outlet 322c is arranged at more X axis plus direction in the X axis direction than the first blower outlet 322a and the second blower outlet 322b. The third blower outlet 322c is connected to the third blower pipe 321e in a condition where the third blower outlet 322c faces toward the X axis minus direction, for example. By this, the third blower outlet 322c is allowed to blow the wind toward the X axis minus direction.

The fourth blower outlet 322d is an opening along the Y axis direction. A length of the opening along the Y axis direction is longer than the length of the short side of the plate 60, for example. The fourth blower outlet 322d is connected to the fourth blower pipe 321f. The fourth blower outlet 322d is arranged at more X axis plus direction in the X axis direction than the first blower outlet 322a and the second blower outlet 322b. The fourth blower outlet 322d is connected to the fourth blower pipe 321f in a condition where the fourth blower outlet 322d faces toward the X axis minus direction, for example. By this, the fourth blower outlet 322d is allowed to blow the wind toward the X axis minus direction.

In the drying device 320, a space between the first blower outlet 322a to the second bower outlet 322b that are arranged at the X axis minus side and the third blower outlet 322c to the fourth bower outlet 322d that are arranged at the X axis plus side is a drying position P5. The plate 60 is dried at the drying position P5. For example, the plate 60 is supported in the upright condition and dried at the drying position P5. For example, the plate 60 is supported at the drying position P5 in a condition where the openings of the wells face toward the X axis minus direction. The blower outlets 322 supply the wind to the plate 60 that has been supported at the drying position P5 from both sides of the plate 60. As an example, the first blower outlet 322a to the second bower outlet 322b supply the wind from the X axis minus side of the plate 60 to the X axis plus direction, and the third blower outlet 322c to the fourth blower outlet 322d supply the wind from the X axis plus side of the plate 60 to the X axis minus direction. By this, both surfaces of the plate 60 at the X axis minus side and the X axis plus side, i.e., the entire plate including a portion at the X axis minus side and a portion at the X axis plus side can be dried effectively.

Note that the blower outlets 322 may be configured to include only the first blower outlet 322a to the second blower outlet 322b at the X axis minus side and not to include the third blower outlet 322c to the fourth blower outlet 322d at the X axis plus side.

The transporting device 330 is provided with a plate supporting part 331 and a driving part 332. The plate supporting part 331 is a member for supporting the plate 60. The driving part 332 moves the plate supporting part 331. As an example, the driving part 332 moves the plate supporting part 331 among a delivery position P4, the drying position P5 and the cleaning position P6. In this way, the transporting device 330 is a transport line for transporting the plate 60.

The controlling device 340 controls an operation of each of the cleaning device 310, the drying device 320 and the transporting device 330. The control by the controlling device 340 will be described later in detail with reference to FIG. 5 to FIG. 8.

The housing device 350 houses the cleaning device 310, the drying device 320 and the transporting device 330. The housing device 350 is provided with a case 351 and a door 352.

The case 351 forms a space in which the cleaning device 310, the drying device 320 and the transporting device 330 are housed. The case 351 is a chassis whose shape is box-like, for example. The cleaning device 310, the drying device 320 and the transporting device 330 are housed in the inner space that is formed by the case 351. The case 351 includes an opening 351a and a drain outlet 351b.

The opening 351a is a gate through which the plate 60 is inserted from an outside of the case 351 to an inside of the case 351 and the plate 60 is extracted from the inside of the case 351 to the outside of the case 351. The transporting apparatus 50 uses the opening 351a in delivering the plate 60 that has been received from the dispensing apparatus 20 to the plate supporting part 331 of the transporting device 330 and receiving the plate 60 that has been supported by the plate supporting part 331 of the transporting device 330.

The drain outlet 351b is an opening through which the waste solution in the case 351 is discharged to the outside of the case 351. The cleaning solution that has been used to clean the plate 60 in the cleaning device 310 is the waste solution. This waste solution is discharged to the outside of the case 351 through the drain outlet 351b.

The door 352 can be in an opening condition where the opening 351a is opened and in a closing condition where the opening 351a is closed. When the transporting apparatus 50 delivers the plate 60 that has been received from the dispensing apparatus 20 to the plate supporting part 331 of the transporting device 330 and the transporting apparatus 50 receives the plate 60 that has been supported by the plate supporting part 331 of the transporting device 330, the door 352 is in the opening condition. When the cleaning device 310 cleans the plate 60 and the drying device 320 dries the plate 60, the door 352 is in the closing condition. By this, the inactive gas can be circulated and reused effectively, and thus an amount of the used inactive gas can be reduced. Moreover, the discharge of the inactive gas from the inner space of the case 351 to an outer space of the case 351 can be prevented.

Note that an emission processing unit 370 for discharging (exhausting) the inactive gas that is blew from the blower outlets 322 may be arranged near the drying device 320 in the housing device 350. For example, the emission processing unit 370 is configured to be provided with a filter for filtering and removing dust and undesired material included in the discharged gas and to return (circulate) the discharged gas that has passed through the filter, i.e., the clean inactive gas, to the blower part 321.

The waste solution collecting device 360 is provided with a drain pipe 361 and a waste solution storing part 362.

The drain pipe 361 connects the drain outlet 351*b* and the waste solution storing part 362. As an example, the drain pipe 362 is a pipe for supplying the waste solution that is discharged from the inside of the case 351 to the waste solution storing part 362 via the drain outlet 351*b*.

The waste solution storing part 362 is a case for storing the waste solution that is supplied by the drain pipe 361. The waste solution storing part 362 is a tank, for example. The waste solution storing part 362 is configured to be exchangeable to the cleaning and drying apparatus 30.

The cleaning device 310 is arranged below the drying device 320. The cleaning device 310 is arranged at more Z axis minus side in the Z axis direction than the drying device 320.

The cleaning solution nozzles 312 are arranged below the blower outlets 322. The cleaning solution nozzles 312 are arranged is arranged at more Z axis minus side in the Z axis direction than the blower outlets 322.

The cleaning solution supplying part 311 is arranged below the blower part 321. The cleaning solution supplying part 311 are arranged is arranged at more Z axis minus side in the Z axis direction than the blower part 321.

The cleaning device 310 is arranged at a height level lower than a height level at which the transporting device 210 of the dispensing apparatus 20 is arranged, for example. The cleaning device 310 is arranged at more Z axis minus side in the Z axis direction than the height level at which the transporting device 210 of the dispensing apparatus 20 is arranged, for example.

The cleaning device 310 is arranged at a height level lower than a height level at which the placing device 420 of the detecting apparatus 40 is arranged, for example. The cleaning device 310 is arranged at more Z axis minus side in the Z axis direction than the height level at which the placing device 420 of the detecting apparatus 40 is arranged, for example.

The drying device 320 is arranged above the cleaning device 310. The drying device 320 is arranged at more Z axis plus side in the Z axis direction than the cleaning device 310.

The bower outlets 322 are arranged above the cleaning solution nozzles 312. The bower outlets 322 are arranged at more Z axis plus side in the Z axis direction than the cleaning solution nozzles 312.

The blower part 321 is arranged above the cleaning solution supplying part 311. The blower part 321 is arranged at more Z axis plus side in the Z axis direction than the cleaning solution supplying part 311.

The drying device 320 is arranged at a height level lower than the height level at which the transporting device 210 of the dispensing apparatus 20 is arranged, for example. The drying device 320 is arranged at more Z axis minus side in the Z axis direction than the height level at which the transporting device 210 of the dispensing apparatus 20 is arranged, for example.

The drying device 320 is arranged at a height level lower than the height level at which the placing device 420 of the detecting apparatus 40 is arranged, for example. The drying device 320 is arranged at more Z axis minus side in the Z axis direction than the height level at which the placing device 420 of the detecting apparatus 40 is arranged, for example.

The plate 60 that has been transported to the delivery position P3 in the dispensing apparatus 20 after being dispensed is grasped by a robot arm (not illustrated) of the transporting apparatus 50 and then is delivered to the cleaning and drying apparatus 30. At this time, the robot arm (a rotational operating part) of the transporting apparatus 50 grasps the plate 60 that is placed on the plate supporting part 211 of the dispensing apparatus in the horizontal condition, then rotates the grasped plate 60 by 90 degree to the upright condition and then sets the plates 60 in the upright condition to the plate supporting part 331 of the transporting device 330 in the cleaning and drying apparatus 30 at the delivery position P4. For example, the plate 60 is rotated by 90 degree to a clockwise direction or a counterclockwise direction around the Y axis to be from the horizontal condition to the upright condition.

The cleaning and drying apparatus 30 transports the plate 60 in the upright condition that has been set to the plate supporting part 311 of the transporting device 330 downwardly in the vertical direction (toward the Z axis minus direction) to the cleaning position P6 in the cleaning device 310, then cleans the plate 60 in the cleaning device 310, then transports the plate 60 upwardly in the vertical direction (toward the Z axis plus direction) to the drying position P5 in the drying device 320, and then dries the plate 60 in the drying device 320. While the plate 60 passes through the drying device 320 when it is transported downwardly, the drying device 320 does not operate. The plate 60 is cleaned and dried in order as described above while being held in the upright condition, and then transported to the delivery position P4 in the cleaning and drying apparatus 30 by the transporting device 330.

FIG. 5 is a drawing for describing the control for the cleaning device 310, the drying device 320 and the transporting device 330 by the controlling device 340.

FIG. 5(*a*) is a drawing conceptually illustrating a positional relationship among the cleaning device 310, the drying device 320, the transporting device 330, the delivery position P4, the drying position P5 and the cleaning position P6. In FIG. 5(*a*), the cleaning device 310 is arranged below (at the Z axis minus side of) the drying device 320. The cleaning device 310 includes therein the cleaning position P6. As described above, the cleaning position P6 is the space between the first cleaning solution nozzle 312*a* to the twenty fourth cleaning solution nozzle 312*x* and the twenty fifth cleaning solution nozzle 312*y* to the forty second cleaning solution nozzle 312P. The cleaning position P6 is a position at which the plate 60 is cleaned in the cleaning device 310. The drying device 320 includes therein the drying position P5. As described above, the drying position P5 is the space between the first blower outlet 322*a* to the second bower outlet 322*b* and the third blower outlet 322*c* to the fourth bower outlet 322*d*. The drying position P5 is a position at which the plate 60 is dried in the drying device 320. Therefore, the cleaning position P6 is arranged below (at the Z axis minus side of) the drying position P5. The delivery position P4 is a position at which the delivering and the receiving of the plate 60 are performed between the transporting apparatus 50 and the transporting device 330 of the cleaning and drying apparatus 30. The delivery position P4 is arranged above (at the Z axis plus side of) the drying position P5. In this way, the delivery position P4, the drying position P5 and the cleaning position P6 are arranged in an order of the delivery position P4, the drying position P5 and the cleaning position P6 from an upper side to a lower side. The delivery position P4, the drying position P5 and the cleaning position P6 are arranged in a line along the Z axis.

The transporting device 330 is arranged so as to transport the plate 60 to each of the delivery position P4, the drying position P5 and the cleaning position P6. As described above, the transporting device 330 transports the plate 60 among the delivery position P4, the drying position P5 and the cleaning position P6.

FIG. 5(*b*) conceptually illustrates a condition where the plate 60 is at the delivery position P4. The plate 60 is at the delivery position P4, when the plate 60 is delivered from the transporting apparatus 50 to the transporting device 330 of the cleaning and drying apparatus 30 after being dispensed and when the plate 60 is delivered from the transporting device 330 of the cleaning and drying apparatus 30 to the transporting apparatus 50 after being cleaned and dried. The plate 60 is supported in the upright condition at the delivery position P4, for example.

FIG. 5(*c*) conceptually illustrates a condition where the plate 60 is at the drying position P5. The drying position P5 is a position via which the plate 60 is transported between the delivery position P4 and the cleaning position P6 by the transporting device 330. The plate 60 is at the drying position P5, when the plate 60 is dried in the drying device 320. The plate 60 is supported in the upright condition at the drying position P5, for example.

FIG. 5(*d*) conceptually illustrates a condition where the plate 60 is at the cleaning position P6. The cleaning position P6 is a position to which the plate 60 is transported from the delivery position P4 via the drying position P5 by the transporting device 330. The plate 60 is at the cleaning position P6, when the plate 60 is cleaned in the cleaning device 310. The plate 60 is supported in the upright condition at the cleaning position P6, for example.

The controlling device 340 starts the control for the cleaning process and the drying process after the dispensed plate 60 is delivered from the transporting apparatus 50 to the transporting device 330 of the cleaning and drying apparatus 30 to be at the delivery position P4 in FIG. 5(*b*).

Firstly, the controlling device 340 controls the transporting device 330 to transport the plate 60 downwardly. As an example, the controlling device 340 controls the transporting device 330 to transport the plate 60 that is at the delivery position P4 from the delivery position P4 to the cleaning position P6 via the drying position P5. As an example, the controlling device 340 controls the controlling device 340 to transport the plate 60 that is at the delivery position P4 from the delivery position P4 to the cleaning position P6 without stopping the plate 60 at the drying position P5. Moreover, the controlling device 340 controls the drying device 320 so that the drying device 320 does not perform a drying operation when the plate 60 passes through the drying position P5. The transporting device 330 transports the plate 60 from the delivery position P4 to the cleaning position P6 via the drying position P5 in response to the control by the controlling device 340. The drying device 320 keeps the drying operation in a suspended condition during a period when the plate 60 is transported by the transporting device 330 from the delivery position P4 to the cleaning position P6 via the drying position P5 in response to the control by the controlling device 340. By this, the plate 60 is transported by the transporting device 330 from the delivery position P4 to the cleaning position P6 via the drying position P5. The plate 60 is transported by the transporting device 330 from the delivery position P4 to the cleaning position P6 via the drying position P5 while being supported in the upright condition, for example. The drying device 320 does not perform the drying process on the plate 60 when the plate 60 passes through the drying device 320. The drying device 320 does not perform the drying process on the plate 60 when the plate 60 passes through the drying position P5. In this way, the position of the plate 60 is changed from a condition where the plate 60 is at the delivery position P4 as illustrated in FIG. 5(*b*) to a condition where the plate 60 is at the cleaning position P6 as illustrated in FIG. 5(*d*) via a condition where the plate 60 is at the drying position P5 as illustrated in FIG. 5(*c*).

Next, the controlling device 340 controls the cleaning device 310 to clean the plate 60. Moreover, the controlling device 340 controls the transporting device 330 to keep the plate 60 to stop at the cleaning position P6 during a cleaning operation by the cleaning device 310. In response to the control by the controlling device 340, the transporting device 330 keeps the plate 60 to be at the cleaning position P6 and the cleaning device 310 cleans the plate 60. By this, the plate 60 is cleaned at the cleaning position P6 by the cleaning device 310. The plate 60 is cleaned at the cleaning position P6 by the cleaning device 310 while being supported in the upright condition, for example. At this timing, the position of the plate 60 keeps being in the condition where the plate 60 is at the cleaning position P6 as illustrated in FIG. 5(*d*).

Next, after the cleaning of the plate 60 is finished, the controlling device 340 controls the transporting device 330 to transport the plate 60 upwardly. As an example, the controlling device 340 controls the transporting device 330 to transport the plate 60 that is at the cleaning position P6 from the cleaning position P6 to the drying position P5. The transporting device 330 transports the plate 60 from the cleaning position P6 to the drying position P5 in response to the control by the controlling device 340. By this, the plate 60 is transported by the transporting device 330 from the cleaning position P6 to the drying position P5. The plate 60 is transported from the cleaning position P6 to the drying position P5 while being supported in the upright condition, for example. In this way, the position of the plate 60 is changed from the condition where the plate 60 is at the cleaning position P6 as illustrated in FIG. 5(*d*) to the condition where the plate 60 is at the drying position P5 as illustrated in FIG. 5(*c*).

Next, the controlling device 340 controls the drying device 320 to dry the plate 60. Moreover, the controlling device 340 controls the transporting device 330 to keep the plate 60 to stop at the drying position P5 during the drying operation by the cleaning device 310. In response to the control by the controlling device 340, the transporting device 330 keeps the plate 60 to be at the drying position P5 and the drying device 320 dries the plate 60. By this, the plate 60 is dried at the drying position P5 by the drying device 320. The plate 60 is dried at the drying position P5 by the drying device 320 while being supported in the upright condition, for example. At this timing, the position of the plate 60 keeps being in the condition where the plate 60 is at the drying position P5 as illustrated in FIG. 5(*c*).

Next, after the drying of the plate 60 is finished, the controlling device 340 controls the transporting device 330 to transport the plate 60 upwardly. As an example, the controlling device 340 controls the transporting device 330 to transport the plate 60 that is at the drying position P5 from the drying position P5 to the delivery position P4. The transporting device 330 transports the plate 60 from the drying position P5 to the delivery position P4 in response to the control by the controlling device 340. By this, the plate 60 is transported by the transporting device 330 from the drying position P5 to the delivery position P4. The plate 60 is transported from the drying position P5 to the delivery position P4 while being supported in the upright condition, for example. In this way, the position of the plate 60 is changed from the condition where the plate 60 is at the drying position P5 as illustrated in FIG. 5(c) to the condition where the plate 60 is at the delivery position P4 as illustrated in FIG. 5(b).

The plate 60 on which the cleaning process and the drying process has been performed and which has returned to the delivery position P4 is received by the transporting apparatus 50 and then transported to the detecting apparatus 40.

FIG. 6 is a drawing for describing a first modified example of the control for the cleaning device 310, the drying device 320 and the transporting device 330 by a controlling device 340.

FIG. 6(a) is a drawing conceptually illustrating a positional relationship among the cleaning device 310, the drying device 320, the transporting device 330, the delivery position P4, the drying position P5 and the cleaning position P6.

The cleaning device 310 is arranged below (at the Z axis minus side of) the drying device 320. The cleaning device 310 includes therein the cleaning position P6. As described above, the cleaning position P6 is the space between the first cleaning solution nozzle 312a to the twenty fourth cleaning solution nozzle 312x and the twenty fifth cleaning solution nozzle 312y to the forty second cleaning solution nozzle 312P. The cleaning position P6 includes a first cleaning position P6a and a second cleaning position P6b. The first cleaning position P6a is a space at the X axis minus side in the cleaning position P6. The second cleaning position P6b is a space at the X axis plus side in the cleaning position P6. The first cleaning position P6a is a position at which the plate 60 is cleaned in the cleaning device 310.

The drying device 320 includes therein the drying position P5. As described above, the drying position P5 is the space between the first blower outlet 322a to the second bower outlet 322b and the third blower outlet 322c to the fourth bower outlet 322d. The drying position P5 includes a first drying position P5a and a second drying position P5b. The first drying position P5a is a space at the X axis minus side in the drying position P5. The second drying position P5b is a space at the X axis plus side in the drying position P5. The first drying position P5a is a position through which the plate 60 passes when the plate 60 is transported from the delivery position P4 to the cleaning position P6. The second drying position P5b is a position at which the plate 60 is dried in the drying device 320.

The delivery position P4 is a position at which the delivering and the receiving of the plate 60 are performed between the transporting apparatus 50 and the transporting device 330 of the cleaning and drying apparatus 30. The delivery position includes a first delivery position P4a and a second delivery position P4b. The first delivery position P4a is a space at the X axis minus side in the delivery position P4. The second delivery position P4b is a space at the X axis plus side in the delivery position P4. The first delivery position P4a is a position at which the transporting apparatus 50 delivers the dispensed plate 60 to the transporting device 330 of the cleaning and drying apparatus 30. The second delivery position P4b is a position to which the plate 60 is transported for the transporting device 50 to receive the cleaned and dried plate 60.

The cleaning position P6 is arranged below (at the Z axis minus side of) the drying position P5. The delivery position P4 is arranged above (at the Z axis plus side of) the drying position P5. The delivery position P4, the drying position P5 and the cleaning position P6 are arranged in an order of the delivery position P4, the drying position P5 and the cleaning position P6 from an upper side to a lower side. The delivery position P4, the drying position P5 and the cleaning position P6 are arranged in a line along the Z axis. The first delivery position P4a, the first drying position P5a and the second cleaning position P6a are arranged in a line along the Z axis. The second delivery position P4b, the second drying position P5b and the second cleaning position P6b are arranged in a line along the Z axis.

The transporting device 330 is arranged so as to transport the plate 60 to each of the delivery position P4, the drying position P5 and the cleaning position P6. As described above, the transporting device 330 transports the plate 60 among the delivery position P4, the drying position P5 and the cleaning position P6. As an example, the transporting device 330 transports the plate 60 from the first delivery position P4 to the first drying position P5a, then to the first cleaning position P6a, then to the second cleaning position P6b, then to the second drying position P5b and finally to the second delivery position P4b. The transporting device 330 is provided with two plate supporting parts 331. The driving part 332 of the transporting device 330 is configured to move two plate supporting parts 331 separately. The transporting device 330 is able to transport two plates 60 in parallel by using two plate supporting parts 331.

An example using a first plate 60-1, a second plate 60-2 and a third plate 60-3 will be described.

The first plate 60-1 is a plate on which the cleaning process by the cleaning device 310 is performed first, among the first plate 60-1, the second plate 60-2 and the third plate 60-3. The first plate 60-1 is a plate on which the drying process by the drying device 320 is performed first, among the first plate 60-1, the second plate 60-2 and the third plate 60-3. The first plate 60-1 is a plate on which the cleaning process by the cleaning device 310 and the drying process by the drying device 320 are performed first, among the first plate 60-1, the second plate 60-2 and the third plate 60-3. The first plate 60-1 is a plate on which the cleaning process by the cleaning device 310 and the drying process by the drying device 320 are performed at the earliest timing.

The second plate 60-2 is a plate on which the cleaning process by the cleaning device 310 is performed after the cleaning process on the first plate 60-1. The second plate 60-2 is a plate on which the drying process by the drying device 320 is performed after the drying process on the first plate 60-1. The second plate 60-2 is a plate on which the cleaning process by the cleaning device 310 and the drying process by the drying device 320 are performed after the cleaning process and the drying process on the first plate 60-1.

The third plate 60-3 is a plate on which the cleaning process by the cleaning device 310 is performed after the cleaning process on the second plate 60-2. The third plate 60-3 is a plate on which the drying process by the drying device 320 is performed after the drying process on the second plate 60-2. The third plate 60-3 is a plate on which the cleaning process by the cleaning device 310 and the drying process by the drying device 320 are performed after the cleaning process and the drying process on the second plate 60-2.

FIG. 6(b) illustrates a condition where the first plate 60-1 is at the first delivery position P4a. The first plate 60-1 is at the first delivery position P4a, when the first plate 60-1 is delivered from the transporting apparatus 50 to the transporting device 330 of the cleaning and drying apparatus 30 after being dispensed. The first plate 60-1 is supported in the upright condition at the first delivery position P4*a*, for example.

FIG. 6(*c*) illustrates a condition where the first plate 60-1 is at the first drying position P5*a*. The first plate 60-1 is at the first drying position P5*a* in the middle of the transportation of the first plate 60-1 from the first delivery position P4*a* to the first cleaning position P6*a* by the transporting device 330. The first plate 60-1 is supported in the upright condition at the first drying position P5*a*, for example.

FIG. 6(*d*) illustrates a condition where the first plate 60-1 is at the first cleaning position P6*a*. The first plate 60-1 is at the first cleaning position P6*a*, when the first plate 60-1 is cleaned in the cleaning device 310. The first plate 60-1 is supported in the upright condition at the first cleaning position P6*a*, for example.

FIG. 6(*e*) illustrates a condition where the first plate 60-1 is at the second cleaning position P6*b* and the second plate 60-2 is at the first delivery position P4*a*. The first plate 60-1 is transported from the first cleaning position P6*a* by the transporting device 330 after being cleaned and then is at the second cleaning position P6*b*. The first plate 60-1 is supported in the upright condition at the second cleaning position P6*b*, for example. The second plate 60-2 is at the first delivery position P4*a*, when the second plate 60-2 is delivered from the transporting apparatus 50 to the transporting device 330 of the cleaning and drying apparatus 30 after being dispensed. The second plate 60-2 is supported in the upright condition at the first delivery position P4*a*, for example.

FIG. 6(*f*) illustrates a condition where the first plate 60-1 is at the second drying position P5*b* and the second plate 60-2 is at the first drying position P5*a*. The second plate 60-2 is at the first drying position P5*a* in the middle of the transportation of the second plate 60-2 from the first delivery position P4*a* to the first cleaning position P6*a* by the transporting device 330. When the second plate 60-2 is at the first drying position P5*a*, the first plate 60-1 is at the second drying position P5*b*. The first plate 60-1 is supported in the upright condition at the second drying position P5*b*, for example. The second plate 60-2 is supported in the upright condition at the first drying position P5*a*, for example.

FIG. 6(*g*) illustrates a condition where the first plate 60-1 is at the second drying position P5*b* and the second plate 60-2 is at the first cleaning position P6*a*. The first plate 60-1 is at the second drying position P5*b*, when the first plate 60-1 is dried in the drying device 320. The first plate 60-1 is supported in the upright condition at the second drying position P5*b*, for example. The second plate 60-2 is at the first cleaning position P6*a*, when the second plate 60-2 is cleaned in the cleaning device 310. The second plate 60-2 is supported in the upright condition at the first cleaning position P6*a*, for example.

FIG. 6(*h*) illustrates a condition where the first plate 60-1 is at the second delivery position P4*b*, the second plate 60-2 is at the second cleaning position P6*b* and the third plate 60-3 is at the first delivery position P4. The first plate 60-1 is at the second delivery position P4*b*, when the first plate 60-1 is delivered from the transporting device 330 of the cleaning and drying apparatus 30 to the transporting apparatus 50 after being cleaned and dried. The plate 60 is supported in the upright condition at the second delivery position P4*b*, for example. The second plate 60-2 is transported from the first cleaning position P6*a* by the transporting device 330 after being cleaned and then is at the second cleaning position P6*b*. The second plate 60-2 is supported in the upright condition at the second cleaning position P6*b*, for example. The third plate 60-3 is at the first delivery position P4*a*, when the third plate 60-3 is delivered from the transporting apparatus 50 to the transporting device 330 of the cleaning and drying apparatus 30 after being dispensed. The third plate 60-3 is supported in the upright condition at the first delivery position P4*a*, for example.

The controlling device 340 starts the control for the cleaning process and the drying process after the dispensed first plate 60-1 is delivered from the transporting apparatus 50 to the transporting device 330 of the cleaning and drying apparatus 30 and as a result is at the first delivery position P4*a* in FIG. 6(*b*).

Firstly, the controlling device 340 controls the transporting device 330 to transport the first plate 60-1 downwardly. As an example, the controlling device 340 controls the transporting device 330 to transport the first plate 60-1 that is at the first delivery position P4*a* from the first delivery position P4*a* to the first cleaning position P6*a* via the first drying position P5*a*. As an example, the controlling device 340 controls the controlling device 340 to transport the first plate 60-1 that is at the first delivery position P4*a* from the first delivery position P4*a* to the first cleaning position P6*a* without stopping the first plate 60-1 at the first drying position P5*a*. Moreover, the controlling device 340 controls the drying device 320 so that the drying device 320 does not perform the drying operation when the first plate 60-1 passes through the first drying position P5*a*. The transporting device 330 transports the first plate 60-1 from the first delivery position P4*a* to the first cleaning position P6*a* via the first drying position P5*a* in response to the control by the controlling device 340. The drying device 320 keeps the drying operation in the suspended condition during a period when the first plate 60-1 is transported by the transporting device 330 from the first delivery position P4*a* to the first cleaning position P6*a* via the first drying position P5*a* in response to the control by the controlling device 340. By this, the first plate 60-1 is transported by the transporting device 330 from the first delivery position P4*a* to the first cleaning position P6*a* via the first drying position P5*a*. The first plate 60-1 is transported from the first delivery position P4*a* to the first cleaning position P6*a* via the first drying position P5*a* while being supported in the upright condition, for example. The drying device 320 does not perform the drying process on the first plate 60-1 when the first plate 60-1 passes through the drying device 320. The drying device 320 does not perform the drying process on the first plate 60-1 when the first plate 60-1 passes through the first drying position P5*a*. In this way, the position of the first plate 60-1 is changed from a condition where the first plate 60-1 is at the first delivery position P4*a* as illustrated in FIG. 6(*b*) to a condition where the first plate 60-1 is at the first cleaning position P6*a* as illustrated in FIG. 6(*d*) via a condition where the first plate 60-1 is at the first drying position P5*a* as illustrated in FIG. 6(*c*).

Next, the controlling device 340 controls the cleaning device 310 to clean the first plate 60-1. Moreover, the controlling device 340 controls the transporting device 330 to keep the first plate 60-1 to stop at the first cleaning position P6*a* during the cleaning operation by the cleaning device 310. In response to the control by the controlling device 340, the transporting device 330 keeps the first plate 60-1 to be at the first cleaning position P6*a* and the cleaning device 310 cleans the first plate 60-1. By this, the first plate 60-1 is cleaned at the first cleaning position P6*a* by the cleaning device 310. The first plate 60-1 is cleaned at the first cleaning position P6*a* by the cleaning device 310 while being supported in the upright condition, for example. At this timing, the position of the first plate 60-1 keeps being in the condition where the first plate 60-1 is at the first cleaning position P6a as illustrated in FIG. 6(d).

Next, after the cleaning of the first plate 60-1 is finished, the controlling device 340 controls the transporting device 330 to transport the first plate 60-1 toward a second direction. As an example, the controlling device 340 controls the transporting device 330 to transport the first plate 60-1 that is at the first cleaning position P6a from the first cleaning position P6a to the second cleaning position P6b toward a plus X axis direction. The transporting device 330 transports the first plate 60-1 from the first cleaning position P6a to the second cleaning position P6b toward the plus X axis direction in response to the control by the controlling device 340. By this, the first plate 60-1 is transported by the transporting device 330 from the first cleaning position P6a to the second cleaning position P6b toward the plus X axis direction. The first plate 60-1 is transported from the first cleaning position P6a to the second cleaning position P6b toward the plus X axis direction while being supported in the upright condition, for example. Moreover, the transporting device 330 receives the dispensed second plate 60-2 at the second delivery position P4a from the transporting apparatus 50. In this way, the position of each of the first plate 60-1 and the second plate 60-2 is in a condition where the first plate 60-1 is at the second cleaning position P6b and the second plate 60-2 is at the first delivery position P4a as illustrated in FIG. 6(e).

Note that the cleaning device 310 may perform the cleaning process on the first plate 60-1 that has been transported to the second cleaning position P6b. For example, the cleaning device 310 may perform the cleaning process on the first plate 60-1 only at the first cleaning position P6a, may perform the cleaning process on the first plate 60-1 only at the second cleaning position P6b, and may perform the cleaning process on the first plate 60-1 at both of the first cleaning position P6a and the second cleaning position P6b. When the cleaning process is performed on the first plate 60-1 at both of the first cleaning position P6a and the second cleaning position P6b, the cleaning process may be performed during a period when the first plate 60-1 is transported from the first cleaning position P6a to the second cleaning position P6b.

Next, the controlling device 340 controls the transporting device 330 to transport the first plate 60-1 upwardly and to transport the second plate 60-2 downwardly. The controlling device 340 controls the transporting device 330 to transport the first plate 60-1 upwardly while transporting the second plate 60-2 downwardly. As an example, the controlling device 340 controls the transporting device 330 to transport the first plate 60-1 that is at the second cleaning position P6b from the second cleaning position P6b to the second drying position P5b and to transport the second plate 60-2 that is at the first delivery position P4a from the first delivery position P4a to the first cleaning position P6a. The transporting device 330 transports the first plate 60-1 from the second cleaning position P6b to the second drying position P5b in response to the control by the controlling device 340. By this, the first plate 60-1 is transported by the transporting device 330 from the second cleaning position P6b to the second drying position P5b. The first plate 60-1 is transported from the second cleaning position P6b to the second drying position P5b while being supported in the upright condition, for example.

Moreover, the transporting device 330 transports the second plate 60-2 from the first delivery position P4a to the first cleaning position P6a in response to the control by the controlling device 340. At the timing when the first plate 60-1 is at the second drying position P5b as a result of the transportation, the second plate 60-2 is at the first drying position P5a that is in the middle of the transportation to the first cleaning position P6a corresponding to a destination, as illustrated in FIG. 6(f). In other words, the first plate 60-1 reaches the second drying position P5b corresponding to a destination before the second plate 60-2 reaches the first cleaning position P6a corresponding to the destination. The controlling device 340 controls the drying device 320 so that the drying device 320 does not perform the drying operation when the second plate 60-2 passes through the first drying position P5a. The drying device 320 keeps the drying operation in the suspended condition in response to the control by the controlling device 340. By this, the drying device 320 does not perform the drying operation when the second plate 60-2 passes through the first drying position P5a, even when the first plate 60-1 already reaches the second drying position P5b corresponding to the destination. That is, the drying of the first plate 60-2 is temporarily suspended. The second plate 60-2 is furthermore transported downwardly by the transporting device 330 and finally reaches the first cleaning position P6a as illustrated in FIG. 6(g). The second plate 60-2 is transported from the first delivery position P4a to the first cleaning position P6a while being supported in the upright condition, for example. Note that the drying process may starts to be performed on the first plate 60-1 that has already reached the second drying position P5b before the second plate 60-2 reaches the first cleaning position P6a. For example, the controlling device 340 may start controlling the drying device 320 to dry the first plate 60-1 after the second plate 60-2 finishes passing through the entire first drying position P5a and before the second plate 60-2 reaches the first cleaning position P6a.

In this way, the position of each of the first plate 60-1 and the second plate 60-2 is changed from the condition illustrated in FIG. 6(e) to the condition illustrated in FIG. 6(g) via the condition illustrated in FIG. 6(f).

Next, the controlling device 340 controls the drying device 320 to dry the first plate 60-1 and controls the cleaning device 310 to clean the second plate 60-2. Moreover, the controlling device 340 controls the transporting device 330 to keep the first plate 60-1 to stop at the second drying position P5b during the drying operation by the drying device 320 and to keep the second plate 60-2 to stop at the first cleaning position P6a during the cleaning operation by the cleaning device 310. In response to the control by the controlling device 340, the transporting device 330 keeps the first plate 60-1 to be at the second drying position P5b and the drying device 320 dries the first plate 60-1. By this, the first plate 60-1 is dried at the second drying position P5b by the drying device 320. The first plate 60-1 is dried at the second drying position P5b by the drying device 320 while being supported in the upright condition, for example. Moreover, in response to the control by the controlling device 340, the transporting device 330 keeps the second plate 60-2 to be at the first cleaning position P6a and the cleaning device 310 cleans the second plate 60-2. By this, the second plate 60-2 is cleaned at the first cleaning position P6a by the cleaning device 310. The second plate 60-2 is cleaned at the first cleaning position P6a by the cleaning device 310 while being supported in the upright condition, for example. At this timing, the position of each of the first plate 60-1 and the second plate 60-2 keeps being in the condition illustrated in FIG. 6(g).

Next, after the drying of the first plate 60-1 and the cleaning of the second plate 60-2 are finished, the controlling device 340 controls the transporting device 330 to transport the first plate 60-1 upwardly and to transport the second plate 60-2 toward the plus X axis direction. As an example, the controlling device 340 controls the transporting device 330 to transport the first plate 60-1 that is at the second drying position P5*b* from the second drying position P5*b* to the second delivery position P4*b* upwardly and to transport the second plate 60-2 that is at the first cleaning position P6*a* from the first cleaning position P6*a* to the second cleaning position P6*b* toward the plus X axis direction. The transporting device 330 transports the first plate 60-1 from the second drying position P5*b* to the second delivery position P4*b* in response to the control by the controlling device 340. By this, the first plate 60-1 is transported by the transporting device 330 from the second drying position P5*b* to the second delivery position P4*b*. The first plate 60-1 is transported from the second drying position P5*b* to the second delivery position P4*b* while being supported in the upright condition, for example. Moreover, the transporting device 330 transports the second plate 60-2 from the first cleaning position P6*a* to the second cleaning position P6*b* toward the plus X axis direction in response to the control by the controlling device 340. By this, the second plate 60-2 is transported by the transporting device 330 from the first cleaning position P6*a* to the second cleaning position P6*b* toward the plus X axis direction. The second plate 60-2 is transported from the first cleaning position P6*a* to the second cleaning position P6*b* toward the plus X axis direction while being supported in the upright condition, for example. Moreover, the transporting device 330 receives the dispensed third plate 60-3 at the first delivery position P4*a* from the transporting apparatus 50. In this way, the position of each of the first plate 60-1, the second plate 60-2 and the third plate 60-3 is in a condition illustrated in FIG. 6(*h*).

The first plate 60-1 on which the cleaning process and the drying process have been performed and which has been transported to the second delivery position P4*b* is received by the transporting apparatus 50 and then transported to the detecting apparatus 40. After that, an operation that is same as an operation performed on the first plate 60-1 and the second plate 60-2 is performed on the second plate 60-2 and the third plate 60-3.

FIG. 7 is a drawing for describing a second modified example of the control for the cleaning device 310, the drying device 320 and the transporting device 330 by the controlling device 340.

FIG. 7(*a*) is a drawing illustrating a positional relationship among the cleaning device 310, the drying device 320, the transporting device 330, the delivery position P4, the drying position P5 and the cleaning position P6.

The cleaning device 310 is arranged below (at the Z axis minus side of) the drying device 320. The cleaning device 310 includes therein the cleaning position P6. As described above, the cleaning position P6 is the space between the first cleaning solution nozzle 312*a* to the twenty fourth cleaning solution nozzle 312*x* and the twenty fifth cleaning solution nozzle 312*y* to the forty second cleaning solution nozzle 312P. The cleaning position P6 includes the first cleaning position P6*a* and the second cleaning position P6*b*. The first cleaning position P6*a* is the space at the X axis minus side in the cleaning position P6. The second cleaning position P6*b* is the space at the X axis plus side in the cleaning position P6. The first cleaning position P6*a* is a position at which the plate 60 is cleaned on a first transport line. The second cleaning position P6*b* is a position at which the plate 60 is cleaned on a second transport line.

The drying device 320 includes therein the drying position P5. As described above, the drying position P5 is the space between the first blower outlet 322*a* to the second bower outlet 322*b* and the third blower outlet 322*c* to the fourth bower outlet 322*d*. The drying position P5 includes the first drying position P5*a* and the second drying position P5*b*. The first drying position P5*a* is the space at the X axis minus side in the drying position P5. The second drying position P5*b* is the space at the X axis plus side in the drying position P5. The first drying position P5*a* is a position at which the plate 60 is dried on the first transport line. The second drying position P5*b* is a position at which the plate 60 is dried on the second transport line.

The delivery position P4 is a position at which the delivering and the receiving of the plate 60 are performed between the transporting apparatus 50 and the transporting device 330 of the cleaning and drying apparatus 30. The delivery position P4 includes the first delivery position P4*a* and the second delivery position P4*b*. The first delivery position P4*a* is the space at the X axis minus side in the delivery position P4. The second delivery position P4*b* is the space at the X axis plus side in the delivery position P4. The first delivery position P4*a* is a position at which the transporting apparatus 50 delivers and receives the plate 60 on the first transport line. The second delivery position P4*b* is a position at which the transporting apparatus 50 delivers and receives the plate 60 on the second transport line.

The cleaning position P6 is arranged below (at the Z axis minus side of) the drying position P5. The delivery position P4 is arranged above (at the Z axis plus side of) the drying position P5. The first delivery position P4*a*, the first drying position P5*a* and the first cleaning position P6*a* are arranged on the first transport line in an order of the first delivery position P4*a*, the first drying position P5*a* and the first cleaning position P6*a* from an upper side to a lower side. The first delivery position P4*a*, the first drying position P5*a* and the first cleaning position P6*a* are arranged in a line along the Z axis. The second delivery position P4*b*, the second drying position P5*b* and the second cleaning position P6*b* are arranged on the second transport line in an order of the second delivery position P4*b*, the second drying position P5*b* and the second cleaning position P6*b* from an upper side to a lower side. The second delivery position P4*b*, the second drying position P5*b* and the second cleaning position P6*b* are arranged in a line along the Z axis.

The transporting device 330 is arranged so as to include the delivery position P4, the drying position P5 and the cleaning position P6. As described above, the transporting device 330 transports the plate 60 among the delivery position P4, the drying position P5 and the cleaning position P6. More specifically, the transporting device 330 transports the plate 60 on the first transport line among the first delivery position P4*a*, the first drying position P5*a* and the first cleaning position P6*a*. Moreover, the transporting device 330 transports the plate 60 on the second transport line among the second delivery position P4*b*, the second drying position P5*b* and the second cleaning position P6*b*. The transporting device 330 is provided with one plate supporting part 331 on each of the first transport line and the second transport line. The driving part 332 of the transporting device 330 is configured to move two plate supporting parts 331 separately. The transporting device 330 is able to simultaneously transport two plates 60 by using two plate supporting parts 331 on the first transport line and the second transport line.

FIG. 7(*b*) illustrates a condition where the first plate 60-1 is at the first drying position P5*a* on the first transport line and the second plate 60-2 is at the second cleaning position P6b on the second transport line. The first plate 60-1 is at the first drying position P5a, when the first plate 60-1 is dried in the drying device 320. The first plate 60-1 is supported in the upright condition at the first drying position P5a, for example. The second plate 60-2 is at the second cleaning position P6b, when the second plate 60-2 is cleaned in the cleaning device 310. The second plate 60-2 is supported in the upright condition at the second cleaning position P6b, for example.

FIG. 7(c) illustrates a condition where the first plate 60-1 is at the first delivery position P4a on the first transport line and the second plate 60-2 is at the second drying position P5b on the second transport line. The first plate 60-1 is transported from the first drying position P5a by the transporting device 330 after being dried and then is at the first delivery position P4a. The first plate 60-1 is supported in the upright condition at the first delivery position P4a, for example. The second plate 60-2 is transported from the second cleaning position P6b by the transporting device 330 after being cleaned and then is at the second drying position P5b. The second plate 60-2 is supported in the upright condition at the second drying position P5b, for example.

FIG. 7(d) illustrates a condition where the third plate 60-3 is at the first delivery position P4a on the first transport line and the second plate 60-2 is at the second drying position P5b on the second transport line. The third plate 60-3 is at the first delivery position P4a, when the third plate 60-3 is delivered from the transporting apparatus 50 to the transporting device 330 of the cleaning and drying apparatus 30 after being dispensed. The third plate 60-3 is supported in the upright condition at the first delivery position P4a, for example. The second plate 60-2 is at the second drying position P5b when the third plate 60-3 is at the first delivery position P4a.

FIG. 7(e) illustrates a condition where the third plate 60-3 is at the first cleaning position P6a on the first transport line and the second plate 60-2 is at the second drying position P5b on the second transport line. The third plate 60-3 is at the first cleaning position P6a, when the third plate 60-3 is cleaned in the cleaning device 310. The third plate 60-3 is supported in the upright condition at the first cleaning position P6a, for example. The second plate 60-2 is at the second drying position P5b, when the second plate 60-2 is dried in the drying device 320.

FIG. 7(f) illustrates a condition where the third plate 60-3 is at the first drying position P5a on the first transport line and the second plate 60-2 is at the second delivery position P4b on the second transport line. The third plate 60-3 is transported from the first cleaning position P6a by the transporting device 330 after being cleaned and then is at the first drying position P5a. The third plate 60-3 is supported in the upright condition at the first drying position P5a, for example. The second plate 60-2 is transported from the second drying position P5b by the transporting device 330 after being dried and then is at the second delivery position P4b. The second plate 60-2 is supported in the upright condition at the second delivery position P4b, for example.

FIG. 7(d) illustrates a condition where the third plate 60-3 is at the first drying position P5a on the first transport line and a fourth plate 60-4 is at the second delivery position P4b on the second transport line. The fourth plate 60-4 is at the second delivery position P4b, when the fourth plate 60-4 is delivered from the transporting apparatus 50 to the transporting device 330 of the cleaning and drying apparatus 30 after being dispensed. The fourth plate 60-4 is supported in the upright condition at the second delivery position P4b, for example. The third plate 60-3 is at the first drying position P5a when the fourth plate 60-4 is at the second delivery position P4b.

FIG. 7(h) illustrates a condition where the third plate 60-3 is at the first drying position P5a on the first transport line and the fourth plate 60-4 is at the second cleaning position P6b on the second transport line. The third plate 60-3 is at the first drying position P5a, when the third plate 60-3 is dried in the drying device 320. The fourth plate 60-4 is at the second cleaning position P6b, when the fourth plate 60-4 is cleaned in the cleaning device 310. The fourth plate 60-4 is supported in the upright condition at the second cleaning position P6b, for example.

The controlling device 340 repeats the control among a condition illustrated in FIG. 7(b) to a condition illustrated in FIG. 7(h). For the convenience of description, the control by the controlling device 340 that starts from a condition illustrated in FIG. 7(b) will be described.

Firstly, the controlling device 340 controls the drying device 320 to dry the first plate 60-1 that is at the first dying position P5a. Moreover, the controlling device 340 controls the transporting device 330 to keep the first plate 60-1 to stop at the first drying position P5a during the drying operation by the drying device 320. In response to the control by the controlling device 340, the transporting device 330 keeps the first plate 60-1 to be at the first drying position P5a and the drying device 320 dries the first plate 60-1. By this, the first plate 60-1 is dried at the first drying position P5a by the drying device 320. The first plate 60-1 is dried at the first drying position P5a by the drying device 320 while being supported in the upright condition, for example. Moreover, the controlling device 340 controls the cleaning device 310 to clean the second plate 60-2 that is at the second cleaning position P6b. Moreover, the controlling device 340 controls the transporting device 330 to keep the second plate 60-2 to stop at the second cleaning position P6b during the cleaning operation by the cleaning device 310. In response to the control by the controlling device 340, the transporting device 330 keeps the second plate 60-2 to be at the second cleaning position P6b and the cleaning device 310 cleans the second plate 60-2. By this, the second plate 60-2 is cleaned at the second cleaning position P6b by the cleaning device 310. The second plate 60-2 is cleaned at the second cleaning position P6b by the cleaning device 310 while being supported in the upright condition, for example. At this timing, the position of each of the first plate 60-1 and the second plate 60-2 is in the condition illustrated in FIG. 7(b).

Next, after the drying of the first plate 60-1 and the cleaning of the second plate 60-2 are finished, the controlling device 340 controls the transporting device 330 to transport the first plate 60-1 upwardly and to transport the second plate 60-2 upwardly. As an example, the controlling device 340 controls the transporting device 330 to transport the first plate 60-1 that is at the first drying position P5a from the first drying position P5a to the first delivery position P4a upwardly and to transport the second plate 60-2 that is at the second cleaning position P6b from the second cleaning position P6b to the second drying position P5b upwardly. The transporting device 330 transports the first plate 60-1 from the first drying position P5a to the first delivery position P4a in response to the control by the controlling device 340. By this, the first plate 60-1 is transported by the transporting device 330 from the first drying position P5a to the first delivery position P4. The first plate 60-1 is transported from the first drying position P5a to the first delivery position P4a while being supported in the upright condition, for example. Moreover, the transporting device 330 transports the second plate 60-2 from the second cleaning position P6b to the second drying position P5b in response to the control by the controlling device 340. By this, the second plate 60-2 is transported by the transporting device 330 from the second cleaning position P6b to the second drying position P5b. The second plate 60-2 is transported from the second cleaning position P6b to the second drying position P5b while being supported in the upright condition, for example. In this way, the position of each of the first plate 60-1 and the second plate 60-2 is changed to a condition illustrated in FIG. 7(c).

Next, the first plate 60-1 that has been transported to the first delivery position P4a is received by the transporting apparatus 50 and then transported to the detecting apparatus 40. Moreover, the transporting device 330 receives the dispensed third plate 60-3 at the first delivery position P4a from the transporting apparatus 50, after the transporting apparatus 50 has received the first plate 60-1. By this, the position of each of the second plate 60-2 and the third plate 60-3 is in a condition illustrated in FIG. 7(d).

Next, the controlling device 340 controls the transporting device 330 to transport the third plate 60-3 downwardly. As an example, the controlling device 340 controls the transporting device 330 to transport the third plate 60-3 that is at the first delivery position P4a from the first delivery position P4a to the first cleaning position P6a via the first drying position P5a. Moreover, the controlling device 340 controls the drying device 320 so that the drying device 320 does not perform the drying operation when the third plate 60-3 passes through the first drying position P5a. In response to the control by the controlling device 340, the transporting device 330 transports the third plate 60-3 from the first delivery position P4a to the first cleaning position P6a via the first drying position P5a and the drying device 320 keeps the drying operation in the suspended condition. By this, the third plate 60-3 is transported by the transporting device 330 from the first delivery position P4a to the first cleaning position P6a via the first drying position P5a. The third plate 60-3 is transported from the first delivery position P4a to the first cleaning position P6a via the first drying position P5a while being supported in the upright condition, for example. The second plate 60-2 and the third plate 60-3 are not dried when the third plate 60-3 passes through the first drying position P5a. In this way, the position of each of the second plate 60-2 and the third plate 60-3 is changed to a condition illustrated in FIG. 7(e).

Next, the controlling device 340 controls the drying device 320 to dry the second plate 60-2. Moreover, the controlling device 340 controls the transporting device 330 to keep the second plate 60-2 to stop at the second drying position P5b during the drying operation by the drying device 320. In response to the control by the controlling device 340, the transporting device 330 keeps the second plate 60-2 to be at the second drying position P5b and the drying device 320 dries the second plate 60-2. By this, the second plate 60-2 is dried at the second drying position P5b by the drying device 320. The second plate 60-2 is dried at the second drying position P5b by the drying device 320 while being supported in the upright condition, for example. Moreover, the controlling device 340 controls the cleaning device 310 to clean the third plate 60-3. Moreover, the controlling device 340 controls the transporting device 330 to keep the third plate 60-3 to stop at the first cleaning position P6a during the cleaning operation by the cleaning device 310. In response to the control by the controlling device 340, the transporting device 330 keeps the third plate 60-3 to be at the first cleaning position P6a and the cleaning device 310 cleans the third plate 60-3. By this, the third plate 60-3 is cleaned at the first cleaning position P6a by the cleaning device 310. The third plate 60-3 is cleaned at the first cleaning position P6a by the cleaning device 310 while being supported in the upright condition, for example. At this timing, the position of each of the second plate 60-2 and the third plate 60-3 is in the condition illustrated in FIG. 7(e).

Next, after the drying of the second plate 60-2 and the cleaning of the third plate 60-3 are finished, the controlling device 340 controls the transporting device 330 to transport the second plate 60-2 upwardly and to transport the third plate 60-3 upwardly. As an example, the controlling device 340 controls the transporting device 330 to transport the second plate 60-2 that is at the second drying position P5b from the second drying position P5b to the second delivery position P4b upwardly and to transport the third plate 60-3 that is at the first cleaning position P6a from the first cleaning position P6a to the first drying position P5a upwardly. The transporting device 330 transports the second plate 60-2 from the second drying position P5b to the second delivery position P4b in response to the control by the controlling device 340. By this, the second plate 60-2 is transported by the transporting device 330 from the second drying position P5b to the second delivery position P4b. The second plate 60-2 is transported from the second drying position P5b to the second delivery position P4b while being supported in the upright condition, for example. Moreover, the transporting device 330 transports the third plate 60-3 from the first cleaning position P6a to the first drying position P5a upwardly in response to the control by the controlling device 340. By this, the third plate 60-3 is transported by the transporting device 330 from the first cleaning position P6a to the first drying position P5a. The third plate 60-3 is transported from the first cleaning position P6a to the first drying position P5a while being supported in the upright condition, for example. In this way, the position of each of the second plate 60-2 and the third plate 60-3 is changed to a condition illustrated in FIG. 7(f).

Next, the second plate 60-2 that has been transported to the second delivery position P4b is received by the transporting apparatus 50 and then transported to the detecting apparatus 40. Moreover, the transporting device 330 receives the dispensed fourth plate 60-4 at the second delivery position P4b from the transporting apparatus 50, after the transporting apparatus 50 has received the second plate 60-2. By this, the position of each of the third plate 60-3 and the fourth plate 60-4 is in a condition illustrated in FIG. 7(g).

Next, the controlling device 340 controls the transporting device 330 to transport the fourth plate 60-4 downwardly. As an example, the controlling device 340 controls the transporting device 330 to transport the fourth plate 60-4 that is at the second delivery position P4b from the second delivery position P4b to the second cleaning position P6b via the second drying position P5b. Moreover, the controlling device 340 controls the drying device 320 so that the drying device 320 does not perform the drying operation when the fourth plate 60-4 passes through the second drying position P5b. In response to the control by the controlling device 340, the transporting device 330 transports the fourth plate 60-4 from the second delivery position P4b to the second cleaning position P6b via the second drying position P5b and the drying device 320 keeps the drying operation in the suspended condition. By this, the fourth plate 60-4 is transported by the transporting device 330 from the second delivery position P4b to the second cleaning position P6b via the second drying position P5b. The fourth plate 60-4 is transported from the second delivery position P4b to the second cleaning position P6b via the second drying position P5b while being supported in the upright condition, for example. The third plate 60-3 and the fourth plate 60-4 are not dried when the fourth plate 60-4 passes through the second drying position P5b. In this way, the position of each of the third plate 60-3 and the fourth plate 60-4 is changed to a condition illustrated in FIG. 7(h).

After that, an operation that is same as an operation performed on the first plate 60-1 and the second plate 60-2 is performed on the third plate 60-3 and the fourth plate 60-4.

FIG. 8 is a drawing for describing a third modified example of the control for the cleaning device 310, the drying device 320 and the transporting device 330 by the controlling device 340.

FIG. 8(a) is a drawing illustrating a positional relationship among the cleaning device 310, the drying device 320, the transporting device 330, the delivery position P4, the drying position P5 and the cleaning position P6.

The cleaning position P6 is arranged below (at the Z axis minus side of) the delivery position P4. The drying position P5 is arranged above (at the Z axis plus side of) the delivery position P4. The cleaning position P6 is arranged below (at the Z axis minus side of) the drying position P5. The delivery position P4, the drying position P5 and the cleaning position P6 are arranged in an order of the drying position P5, the delivery position P4 and the cleaning position P6a from an upper side to a lower side. The delivery position P4, the drying position P5 and the cleaning position P6 are arranged in a line along the Z axis.

The cleaning device 310 includes therein the cleaning position P6. As described above, the cleaning position P6 is the space between the first cleaning solution nozzle 312a to the twenty fourth cleaning solution nozzle 312x and the twenty fifth cleaning solution nozzle 312y to the forty second cleaning solution nozzle 312P. The cleaning position P6 is a position at which the plate 60 is cleaned in the cleaning device 310. The drying device 320 includes therein the drying position P5. As described above, the drying position P5 is the space between the first blower outlet 322a to the second bower outlet 322b and the third blower outlet 322c to the fourth bower outlet 322d. The drying position P5 is a position at which the plate 60 is dried in the drying device 320. The delivery position P4 is a position at which the delivering and the receiving of the plate 60 are performed between the transporting apparatus 50 and the transporting device 330 of the cleaning and drying apparatus 30. The transporting device 330 is arranged so as to include the delivery position P4, the drying position P5 and the cleaning position P6. As described above, the transporting device 330 transports the plate 60 among the delivery position P4, the drying position P5 and the cleaning position P6.

FIG. 8(b) illustrates a condition where the plate 60 is at the delivery position P4. The plate 60 is at the delivery position P4, when the plate 60 is delivered from the transporting apparatus 50 to the transporting device 330 of the cleaning and drying apparatus 30 after being dispensed, when the plate 60 is delivered from the transporting device 330 of the cleaning and drying apparatus 30 to the transporting apparatus 50 after being cleaned and dried and when the plate 60 is transported from the cleaning position P6 to the drying position P4 by the transporting device 330. The plate 60 is supported in the upright condition at the delivery position P4, for example.

FIG. 8(c) illustrates a condition where the plate 60 is at the drying position P5. The plate 60 is at the drying position P5, when the plate 60 is dried in the drying device 320. The plate 60 is supported in the upright condition at the drying position P5, for example.

FIG. 8(d) illustrates a condition where the plate 60 is at the cleaning position P6. The plate 60 is at the cleaning position P6, when the plate 60 is cleaned in the cleaning device 310. The plate 60 is supported in the upright condition at the cleaning position P6, for example.

The controlling device 340 starts the control after the dispensed plate 60 is delivered from the transporting apparatus 50 to the transporting device 330 of the cleaning and drying apparatus 30 and as a result is at the delivery position P4 in FIG. 8(b).

Firstly, the controlling device 340 controls the transporting device 330 to transport the plate 60 downwardly. As an example, the controlling device 340 controls the transporting device 330 to transport the plate 60 that is at the delivery position P4 from the delivery position P4 to the cleaning position P6. The transporting device 330 transports the plate 60 from the delivery position P4 to the cleaning position P6 in response to the control by the controlling device 340. By this, the plate 60 is transported by the transporting device 330 from the delivery position P4 to the cleaning position P6. The plate 60 is transported from the delivery position P4 to the cleaning position P6 while being supported in the upright condition, for example. In this way, the position of the plate 60 is changed from a condition where the plate 60 is at the delivery position P4 as illustrated in FIG. 8(b) to a condition where the plate 60 is at the cleaning position P6 as illustrated in FIG. 8(d).

Next, the controlling device 340 controls the cleaning device 310 to clean the plate 60. Moreover, the controlling device 340 controls the transporting device 330 to keep the plate 60 to stop at the cleaning position P6 during the cleaning operation by the cleaning device 310. In response to the control by the controlling device 340, the transporting device 330 keeps the plate 60 to be at the cleaning position P6 and the cleaning device 310 cleans the plate 60. By this, the plate 60 is cleaned at the cleaning position P6 by the cleaning device 310. The plate 60 is cleaned at the cleaning position P6 by the cleaning device 310 while being supported in the upright condition, for example. At this timing, the position of the plate 60 keeps being in the condition where the plate 60 is at the cleaning position P6 as illustrated in FIG. 8(d).

Next, after the cleaning of the plate 60 is finished, the controlling device 340 controls the transporting device 330 to transport the plate 60 upwardly. As an example, the controlling device 340 controls the transporting device 330 to transport the plate 60 that is at the cleaning position P6 from the cleaning position P6 to the drying position P5 via the delivery position P4. The transporting device 330 transports the plate 60 from the cleaning position P6 to the drying position P5 via the delivery position P4 in response to the control by the controlling device 340. By this, the plate 60 is transported by the transporting device 330 from the cleaning position P6 to the drying position P5 via the delivery position P4. The plate 60 is transported from the cleaning position P6 to the drying position P5 via the delivery position P4 while being supported in the upright condition, for example. In this way, the position of the plate 60 is changed from the condition where the plate 60 is at the cleaning position P6 as illustrated in FIG. 8(d) to the condition where the plate 60 is at the drying position P5 as illustrated in FIG. 8(c).

Next, the controlling device 340 controls the drying device 320 to dry the plate 60. Moreover, the controlling device 340 controls the transporting device 330 to keep the plate 60 to stop at the drying position P5 during the drying operation by the drying device 320. In response to the control by the controlling device 340, the transporting device 330 keeps the plate 60 to be at the drying position P5 and the drying device 320 dries the plate 60. By this, the plate 60 is dried at the drying position P5 by the drying device 320. The plate 60 is dried at the drying position P5 by the drying device 320 while being supported in the upright condition, for example. At this timing, the position of the plate 60 keeps being in the condition where the plate 60 is at the drying position P5 as illustrated in FIG. 8(c).

Next, after the drying of the plate 60 is finished, the controlling device 340 controls the transporting device 330 to transport the plate 60 downwardly. As an example, the controlling device 340 controls the transporting device 330 to transport the plate 60 that is at the drying position P5 from the drying position P5 to the delivery position P4 downwardly. The transporting device 330 transports the plate 60 from the drying position P5 to the delivery position P4 downwardly in response to the control by the controlling device 340. By this, the plate 60 is transported by the transporting device 330 from the drying position P5 to the delivery position P4 downwardly. The plate 60 is transported from the drying position P5 to the delivery position P4 downwardly while being supported in the upright condition, for example. In this way, the position of the plate 60 is changed from the condition where the plate 60 is at the drying position P5 as illustrated in FIG. 8(c) to the condition where the plate 60 is at the delivery position P4 as illustrated in FIG. 8(b).

The cleaned and dried plate 60 that has returned to the delivery position P4 is received by the transporting apparatus 50 and then transported to the detecting apparatus 40.

FIG. 9 is a flowchart illustrating a screening method by the screening apparatus 10.

Firstly, a dispensing step is performed in the dispensing apparatus 20 (a step S901). For example, an operator who is an operator of the screening apparatus 10 sets the plate 60 that is an inspected target to the transporting device 210 of the dispensing apparatus 20 and inputs a start command into a control computer (not illustrated) that controls the operation of the screening apparatus 10, and the dispensing step starts by the above operator's operation. After the dispensing step starts, the dispense apparatus 20 transports the set plate 60 to the dispensing position P2 using the transporting device 210 and dispenses the specimen to each well in the plate 60 from the nozzles of the dispensing part 221, in accordance with the control by the control computer. After being dispensed, the plate 60 is transported to the delivery position P3 by the transporting device 210.

Next, a cleaning and drying step is performed in the cleaning and drying apparatus 30 (a step S902). This step will be described later.

After the cleaning and drying step is finished, next, a detecting step is performed in the detecting apparatus 40 (a step S903). The detecting apparatus 40 receives the plate 60 that has been cleaned and dried by the cleaning and drying apparatus 30 from the transporting apparatus 50 and measures the biochip on the plate 60, in accordance with the control by the control computer. As an example, the detecting apparatus 40 images each biochip on the plate 60 by the imaging device 410 to generate the image data of each biochip. Then, the detecting apparatus 40 detects the affinity between the biomolecule on the biochip and the target included in the specimen by analyzing the image data. This inspection result may be stored as electrical data in a storing part in the control computer, for example.

FIG. 10 is a flowchart illustrating the cleaning and drying step in the cleaning and drying apparatus 30. FIG. 10 illustrates, as one example, the cleaning and drying step performed when the controlling device 340 performs the control illustrated in FIG. 5.

Firstly, the transporting apparatus 50 grasps the dispensed plate 60 that is placed in the horizontal condition on the transporting device 210 of the dispensing apparatus 20 by the robot arm and then rotates the grasped plate 60 by 90 degree to the upright condition, by moving the robot arm in accordance with the control by the control computer (a step S1001). Moreover, the transporting apparatus 50 moves the robot arm in accordance with the control by the control computer to sets the plate 60 in the upright condition in the transporting device 330 of the cleaning and drying apparatus 30 at the delivery position P4.

Next, the cleaning and drying apparatus 30 transports the plate 60 that has been set in the transporting device 330 to the cleaning position P6 in the cleaning device 310 by driving the transporting device 330 in accordance with the control by the controlling device 340 to perform a first transporting step (a step S1002). This first transporting step may be a downward transporting step that transports the plate 60 to the cleaning position P6 in the cleaning device 310 downwardly via the drying position P5 in the drying device 320. Note that, at this time, the controlling device 340 controls the drying device 320 to be in the suspended condition so that the drying device 320 does not dry the uncleaned plate 60 when the plate 60 passes through the drying position P5 in the drying device 320.

Next, the cleaning and drying apparatus 30 drives the cleaning device 310 in accordance with the control by the controlling device 340 to perform a cleaning step on the plate 60 (a step S1003). The cleaning device 310 performs the cleaning of the plate 60 by using a suitable method that nebulizes and injects the cleaning solution from the cleaning solution nozzles 312, intermittently injects it or the like. Moreover, for example, the controlling device 340 may spread the cleaning solution uniformly over the entire plate 60 so that cleaning residue does not occur by controlling the transporting device 330 to move up and down the plate 60, in addition to performing an injection control for the cleaning solution on the cleaning device 310.

Next, the cleaning and drying apparatus 30 transports the cleaned plate 60 to the drying position P5 in the drying device 320 upwardly by driving the transporting device 330 in accordance with the control by the controlling device 340 to perform a second transporting step (a step S1004).

Next, the cleaning and drying apparatus 30 drives the drying device 320 in accordance with the control by the controlling device 340 to perform a drying step on the plate 60 (a step S1005). After the drying is finished, the transporting device 330 transport the plate 60 to the delivery position P4 in the cleaning and drying apparatus 30 in accordance with the control by the controlling device 340.

Next, the transporting apparatus 50 grasps the dried plate 60 that is hold at the delivery position P4 by the transporting device 330 of the cleaning and drying apparatus 30 in the upright condition and then rotates the grasped plate 60 by 90 degree to the horizontal condition by moving the robot arm in accordance with the control by the control computer (a step S1006).

Next, the transporting apparatus 50 moves the robot arm in accordance with the control by the control computer to deliver the plate 60 in the horizontal condition to the detecting apparatus 40 (a step S1007).

According to the cleaning and drying apparatus 30 in the present embodiment, it is possible to effectively use a space where the cleaning device 310 and the drying device 320 are placed, because the cleaning device 310 and the drying device 320 are placed in a vertical positional relationship.

According to the cleaning and drying apparatus 30 in the present embodiment, it is possible to effectively use the space where the cleaning device 310 and the drying device 320 are placed and it is possible to effectively perform the cleaning and the drying of the plate.

Although the screening apparatus 10 is configured to be provided with one cleaning and drying apparatus 30 in the embodiment described above, the screening apparatus may be configured to be provided with a plurality of cleaning and drying apparatuses. As an example, the screening apparatus may be configured to be provided with two cleaning and drying apparatuses. Moreover, the screening apparatus may be configured to be provided with a plurality of cleaning devices, not the plurality of cleaning and drying apparatuses. As an example, the screening apparatus may be configured to be provided with two cleaning devices.

FIG. 11 is a drawing conceptually illustrating a structure of a screening apparatus 11 that is provided with two cleaning and drying apparatuses in one embodiment of the present invention. Note that an X axis, a Y axis and a Z axis are defined for the convenience of description. The X axis, the Y axis and the Z axis defines intersecting coordinates. Each of the X axis direction and the Y axis direction is the horizontal direction. The Z axis direction is the vertical direction. The screening apparatus 11 is provided with the dispensing apparatus 20, a first cleaning and drying apparatus 31, a second cleaning and drying apparatus 32, the detecting apparatus 40 and the transporting apparatus 50. The dispensing apparatus 20, the first cleaning and drying apparatus 31, the second cleaning and drying apparatus 32 and the detecting apparatus 40 are arranged in the X axis direction in an order of the dispensing apparatus 20, the first cleaning and drying apparatus 31, the second cleaning and drying apparatus 32 and the detecting apparatus 40.

The screening apparatus 11 is configured to perform a dispensing process on the plate in the dispensing apparatus 20, then to perform a first cleaning and drying process on the plate in the first cleaning and drying apparatus 31, then to perform a second cleaning and drying process on the plate in the second cleaning and drying apparatus 32 and then to perform the detecting process on the plate in the detecting apparatus 40. In the screening apparatus 11, the first cleaning and drying process is performed on the plate in the first cleaning and drying apparatus 31 and subsequently the second cleaning and drying process is performed on the same plate in the second cleaning and drying apparatus 32.

In the screening apparatus 11, the transporting apparatus 50 transports the plate on which the dispensing process has been performed from the dispensing apparatus 20 to the first cleaning and drying apparatus 31, transports the plate on which the first cleaning and drying process has been performed from the first cleaning and drying apparatus 31 to the second cleaning and drying apparatus 32, and transports the plate on which the second cleaning and drying process has been performed from the second cleaning and drying apparatus 32 to the detecting apparatus 40.

In the screening apparatus 11, the dispensing apparatus 20 and the detecting apparatus 40 have same structures as the dispensing apparatus 20 and the detecting apparatus 40 of the screening apparatus 10, respectively. Moreover, in the screening apparatus 11, each of the first cleaning and drying apparatus 31 and the second cleaning and drying apparatus 32 has a same structure as the cleaning and drying apparatus 30 of the screening apparatus 10. For the purpose of a simple description, a description about a detailed structure of each of the dispensing apparatus 20, the first cleaning and drying apparatus 31, the second cleaning and drying apparatus 32 and the detecting apparatus 40 is omitted.

The controlling device 340 of the first cleaning and drying apparatus 31 controls the operation of each of the cleaning device 310, the drying device 320 and the transporting device 330 of the first cleaning and drying apparatus 31 so that the first cleaning and drying process is performed on the plate. The controlling device 340 of the first cleaning and drying apparatus 31 may perform the control by using any of the control method illustrated in FIG. 5, the control method illustrated in FIG. 6, the control method illustrated in FIG. 7 and the control method illustrated in FIG. 8. The controlling device 340 of the second cleaning and drying apparatus 32 controls the operation of each of the cleaning device 310, the drying device 320 and the transporting device 330 of the second cleaning and drying apparatus 32 so that the second cleaning and drying process is performed on the plate. The controlling device 340 of the second cleaning and drying apparatus 32 may perform the control by using any of the control method illustrated in FIG. 5, the control method illustrated in FIG. 6, the control method illustrated in FIG. 7 and the control method illustrated in FIG. 8. The control method that is performed by the controlling device 340 of the first cleaning and drying apparatus 31 may be same as or different from the control method that is performed by the controlling device 340 of the second cleaning and drying apparatus 32. As an example, both of the controlling device 340 of the first cleaning and drying apparatus 31 and the controlling device 340 of the second cleaning and drying apparatus 32 may perform the control by using the control method illustrated in FIG. 5. As another example, the controlling device 340 of the first cleaning and drying apparatus 31 may perform the control by using the control method illustrated in FIG. 5 and the controlling device 340 of the second cleaning and drying apparatus 32 may perform the control by using the control method illustrated in FIG. 6, FIG. 7 or FIG. 8.

The first cleaning and drying process that is performed by the first cleaning and drying apparatus 31 may be same as or different from the second cleaning and drying process that is performed by the second cleaning and drying apparatus 32. One example of the case where the first cleaning and drying process that is performed by the first cleaning and drying apparatus 31 is different from the second cleaning and drying process that is performed by the second cleaning and drying apparatus 32 is a case where the cleaning process that is performed by the first cleaning and drying apparatus 31 is different from the cleaning process that is performed by the second cleaning and drying apparatus 32. As an example in this case, the cleaning device 310 of the first cleaning and drying apparatus 31 and the cleaning device 310 of the second cleaning and drying apparatus 32 may be configured to perform the cleaning process by using different types of liquids, respectively. For example, the cleaning device 310 of the first cleaning and drying apparatus 31 may be configured to perform the cleaning process by using the cleaning solution and the cleaning device 310 of the second cleaning and drying apparatus 32 may be configured to perform the cleaning process by using deionized water. Alternatively, as another example, the cleaning device 310 of the first cleaning and drying apparatus 31 and the cleaning device 310 of the second cleaning and drying apparatus 32 may be configured to perform the cleaning process by using liquids whose types are same as each other but whose temperatures or amounts are different from each other, respectively. Another example of the case where the first cleaning and drying process that is performed by the first cleaning and drying apparatus 31 is different from the second cleaning and drying process that is performed by the second cleaning and drying apparatus 32 is a case where the drying process that is performed by the first cleaning and drying apparatus 31 is different from the drying process that is performed by the second cleaning and drying apparatus 32. As an example in this case, the drying device 320 of the first cleaning and drying apparatus 31 and the drying device 320 of the second cleaning and drying apparatus 32 may be configured to perform the drying process by using different types of inactive gases, respectively. Alternatively, as another example, the drying device 320 of the first cleaning and drying apparatus 31 and the drying device 320 of the second cleaning and drying apparatus 32 may be configured to perform the drying process by using inactive gases whose types are same as each other but whose temperatures or amounts are different from each other, respectively. Moreover, another example of the case where the first cleaning and drying process that is performed by the first cleaning and drying apparatus 31 is different from the second cleaning and drying process that is performed by the second cleaning and drying apparatus 32 is a case where the cleaning process that is performed by the first cleaning and drying apparatus 31 is different from the cleaning process that is performed by the second cleaning and drying apparatus 32 and, in addition, the drying process that is performed by the first cleaning and drying apparatus 31 is different from the drying process that is performed by the second cleaning and drying apparatus 32.

In the screening apparatus 11, the first cleaning and drying apparatus 31 and the second cleaning and drying apparatus 32 may simultaneously perform the first cleaning and drying process and the second cleaning and drying process, respectively. That is, in the screening apparatus 11, the first cleaning and drying process that is performed by the first cleaning and drying apparatus 31 and the second cleaning and drying process that is performed by the second cleaning and drying apparatus 32 may be performed in parallel.

As an example, the first cleaning and drying process is performed on a first plate by the first cleaning and drying apparatus 31 and subsequently the second cleaning and drying process is performed on the same first plate by the second cleaning and drying apparatus 32. The first cleaning and drying process is performed on a second plate by the first cleaning and drying apparatus 31 while the second cleaning and drying process is performed on the first plate by the second cleaning and drying apparatus 32. That is, in the screening apparatus 11, the second cleaning and drying process that is performed on the first plate by the second cleaning and drying apparatus 32 and the first cleaning and drying process that is performed on the second plate by the first cleaning and drying apparatus 31 are performed in parallel. As an example, in the screening apparatus 11, the cleaning process that is performed on the first plate by the second cleaning and drying apparatus 32 and the cleaning process that is performed on the second plate by the first cleaning and drying apparatus 31 are performed in parallel. As an example, in the screening apparatus 11, the drying process that is performed on the first plate by the second cleaning and drying apparatus 32 and the drying process that is performed on the second plate by the first cleaning and drying apparatus 31 are performed in parallel. As an example, in the screening apparatus 11, the cleaning process that is performed on the first plate by the second cleaning and drying apparatus 32 and the cleaning process that is performed on the second plate by the first cleaning and drying apparatus 31 are performed in parallel and the drying process that is performed on the first plate by the second cleaning and drying apparatus 32 and the drying process that is performed on the second plate by the first cleaning and drying apparatus 31 are performed in parallel. As an example, in the screening apparatus 11, the cleaning process that is performed on the first plate by the second cleaning and drying apparatus 32 and the drying process that is performed on the second plate by the first cleaning and drying apparatus 31 are performed in parallel. As an example, the drying process that is performed on the first plate by the second cleaning and drying apparatus 32 and the cleaning process that is performed on the second plate by the first cleaning and drying apparatus 31 are performed in parallel. As an example, in the screening apparatus 11, the cleaning process that is performed on the first plate by the second cleaning and drying apparatus 32 and the cleaning process and the drying process that are performed on the second plate by the first cleaning and drying apparatus 31 are performed in parallel. As an example, in the screening apparatus 11, the drying process that is performed on the first plate by the second cleaning and drying apparatus 32 and the cleaning process and the drying process that are performed on the second plate by the first cleaning and drying apparatus 31 are performed in parallel. As an example, in the screening apparatus 11, the cleaning process and the drying process that are performed on the first plate by the second cleaning and drying apparatus 32 and the cleaning process that is performed on the second plate by the first cleaning and drying apparatus 31 are performed in parallel. As an example, in the screening apparatus 11, the cleaning process and the drying process that are performed on the first plate by the second cleaning and drying apparatus 32 and the drying process that is performed on the second plate by the first cleaning and drying apparatus 31 are performed in parallel.

Note that the second plate is a plate on which the cleaning and drying process is performed after the cleaning and drying process on the first plate. For example, if the first plate is a plate on which the cleaning and drying process is performed nth from the start among a plurality of plates that are processed in the screening apparatus 11, the second plate is a plate on which the cleaning and drying process is performed n+1th or more from the start. For example, the second plate may be a plate on which the cleaning and drying process is performed n+1th from the start, a plate on which the cleaning and drying process is performed n+2th from the start or a plate on which the cleaning and drying process is performed n+3th from the start. The first cleaning and drying process is performed on the second plate by the first cleaning and drying apparatus 31, and subsequently the second cleaning and drying process is performed on the same second plate by the second cleaning and drying apparatus 32, as with the first plate.

FIG. 12 is a drawing conceptually illustrating a structure of a screening apparatus 12 that is provided with two cleaning devices in one embodiment of the present invention. Note that an X axis, a Y axis and a Z axis are defined for the convenience of description. The X axis, the Y axis and the Z axis defines intersecting coordinates. Each of the X axis direction and the Y axis direction is the horizontal direction. The Z axis direction is the vertical direction. The screening apparatus 12 is provided with the dispensing apparatus 20, a first cleaning device 310-1, the cleaning and drying apparatus 30; the detecting apparatus 40 and the transporting apparatus 50. The cleaning and drying apparatus 30 is provided with the cleaning device 310 (it is referred to as a second cleaning device 310-2 in the description relating to FIG. 12), the drying device 320, the transporting device 330 and the controlling device 340. The dispensing apparatus 20, the first cleaning device 310-1, the cleaning and drying apparatus 30 and the detecting apparatus 40 are arranged in the X axis direction in an order of the dispensing apparatus 20, the first cleaning device 310-1, the cleaning and drying apparatus 30 and the detecting apparatus 40.

The screening apparatus 12 is configured to perform the dispensing process on the plate in the dispensing apparatus 20, then to perform a first cleaning process on the plate in the first cleaning device 310-1, then to perform a second cleaning process and the drying process on the plate in the cleaning and drying apparatus 30 and then to perform the detecting process on the plate in the detecting apparatus 40. In the screening apparatus 12, the first cleaning process is performed on the plate in the first cleaning device 310-1 and subsequently the second cleaning process and the drying process are performed on the same plate in the cleaning and drying apparatus 30.

In the screening apparatus 12, the transporting apparatus 50 transports the plate on which the dispensing process has been performed from the dispensing apparatus 20 to the first cleaning device 310-1, transports the plate on which the first cleaning process has been performed from the first cleaning device 310-1 to the cleaning and drying apparatus 30, and transports the plate on which the second cleaning process and the drying process have been performed from the cleaning and drying apparatus 30 to the detecting apparatus 40.

In the screening apparatus 12, the dispensing apparatus 20, the cleaning and drying apparatus 30 and the detecting apparatus 40 have same structures as the dispensing apparatus 20, the cleaning and drying apparatus and the detecting apparatus 40 of the screening apparatus 10, respectively. Moreover, in the screening apparatus 12, the first cleaning device 320-1 has a same structure as the cleaning device 310 that is one element of the cleaning and drying apparatus 30. That is, in the screening apparatus 12, the first cleaning device 310-1 has a same structure as the second cleaning device 310-2. For the purpose of a simple description, a description about a detailed structure of each of the dispensing apparatus 20, the first cleaning device 310-1, the cleaning and drying apparatus 30 and the detecting apparatus 40 is omitted.

The first cleaning process that is performed by the first cleaning device 310-1 may be same as or different from the second cleaning process that is performed by the second cleaning device 310-2. As an example of the case where the first cleaning process that is performed by the first cleaning device 310-1 is different from the second cleaning process that is performed by the second cleaning device 310-2, the first cleaning device 310-1 and the second cleaning device 310-2 may be configured to perform the cleaning process by using different types of liquids, respectively. For example, the first cleaning device 310-1 may be configured to perform the cleaning process by using the cleaning solution and the second cleaning device 310-2 may be configured to perform the cleaning process by using deionized water. Alternatively, as another example, the first cleaning device 310-1 and the second cleaning device 310-2 may be configured to perform the cleaning process by using liquids whose types are same as each other but whose temperatures or amounts are different from each other, respectively.

In the screening apparatus 12, the first cleaning device 310-1 performs the first cleaning process while the cleaning and drying apparatus 30 performs the second cleaning process or the drying process. That is, in the screening apparatus 12, the first cleaning process that is performed by the first cleaning device 310-1 and the second cleaning process or the drying process that is performed by the cleaning and drying apparatus 30 may be performed in parallel.

As an example, the first cleaning process is performed on a first plate by the first cleaning device 310-1 and subsequently the second cleaning process is performed on the same first plate by the second cleaning device 310-2 of the cleaning and drying apparatus 30. The first cleaning process is performed on a second plate by the first cleaning device 310-1 while the second cleaning process is performed on the first plate by the second cleaning device 310-2. That is, in the screening apparatus 12, the second cleaning process that is performed on the first plate by the second cleaning device 310-2 and the first cleaning process that is performed on the second plate by the first cleaning device 310-1 are performed in parallel. Alternatively, as another example, the second cleaning process is performed on the first plate by the second cleaning device 310-2 and then the drying process is performed on the same first plate by the drying device 320 of the cleaning and drying apparatus 30. The first cleaning process is performed on the second plate by the first cleaning device 310-1 while the drying process is performed on the first plate by the drying device 320. That is, in the screening apparatus 12, the drying process that is performed on the first plate by the drying device 320 and the first cleaning process that is performed on the second plate by the first cleaning device 310-1 are performed in parallel. Alternatively, as another example, in the screening apparatus 12, the second cleaning process that is performed on the first plate by the cleaning device 310-2 and the drying process that is performed on the first plate by the drying device 320 are performed in parallel with the first cleaning process that is performed on the second plate by the first cleaning device 310-1.

Note that the second plate is a plate on which the cleaning and drying process is performed after the cleaning and drying process on the first plate. For example, if the first plate is a plate on which the cleaning and drying process is performed nth from the start among a plurality of plates which the screening apparatus 12 processes, the second plate is a plate on which the cleaning and drying process is performed n+1th or more from the start. For example, the second plate may be a plate on which the cleaning and drying process is performed n+1th from the start, a plate on which the cleaning and drying process is performed n+2th from the start or a plate on which the cleaning and drying process is performed n+3th from the start. The first cleaning process is performed on the second plate by the first cleaning device 310-1, and subsequently the second cleaning process and the drying process is performed on the same second plate by the cleaning and drying apparatus 30, as with the first plate.

Although the above described screening apparatus 10 in the embodiment is configured to transport the plate by using the transporting device 210 provided in the dispensing apparatus 20, the transporting device 330 provided in the cleaning and drying apparatus 30, the placing device 420 provided in the detecting apparatus 40 and the transporting apparatus 50, the screening apparatus may be configured to be provided with an integrated transporting apparatus that is configured to include a continuous transport line, instead of being provided with a plurality of devices or apparatuses for the transport.

FIG. 13 is a drawing conceptually illustrating a structure of a screening apparatus 13 that is provided with an integrated transporting apparatus 50 that is configured to have the continuous transport line in one embodiment of the present invention. Note that an X axis, a Y axis and a Z axis are defined for the convenience of description. The X axis, the Y axis and the Z axis defines intersecting coordinates. Each of the X axis direction and the Y axis direction is the horizontal direction. The Z axis direction is the vertical direction. The screening apparatus 13 is provided with a dispensing apparatus 21, a cleaning and drying apparatus 33, a detecting apparatus 41 and the transporting apparatus 55. The dispensing apparatus 21, the cleaning and drying apparatus 33 and the detecting apparatus 41 are arranged in the X axis direction in an order of the dispensing apparatus 21, the cleaning and drying apparatus 33 and the detecting apparatus 41.

In the screening apparatus 13, the dispensing apparatus 21 is provided with the dispensing apparatus 220 and the controlling device 230. The dispensing apparatus 220 and the controlling device 230 of the dispensing apparatus 21 have same structure and function as the dispensing apparatus 220 and the controlling device 230 of the dispensing apparatus 20 in the screening apparatus 10, respectively. The dispensing apparatus 21 of the screening apparatus 13 is not provided with the transporting device 210 provided in the dispensing apparatus 20. Instead, one portion of the transporting apparatus 55 is arranged in the dispensing apparatus 21. In the dispensing apparatus 21 of the screening apparatus 13, the plate is transported by the transporting apparatus 55. A route through which the transporting apparatus 55 transports the plate in the dispensing apparatus 21 is same as a route through which the transporting device 210 of the dispensing apparatus 20 transports the plate.

In the screening apparatus 13, the cleaning and drying apparatus 33 is provided with the cleaning device 310, the drying device 320 and the controlling device 340. The cleaning device 310, the drying device 320 and the controlling device 340 of the cleaning and drying apparatus 33 have same structure and function as the cleaning device 310, the drying device 320 and the controlling device 340 of the cleaning and drying apparatus 30 in the screening apparatus 10, respectively. The cleaning and drying apparatus 33 of the screening apparatus 13 is not provided with the transporting device 330 provided in the cleaning and drying apparatus 30. Instead, one portion of the transporting apparatus 55 is arranged in the cleaning and drying apparatus 33. In the cleaning and drying apparatus 33 of the screening apparatus 13, the plate is transported by the transporting apparatus 55. A route through which the transporting apparatus 55 transports the plate in the cleaning and drying apparatus 33 is same as a route through which the transporting device 330 of the cleaning and drying apparatus 30 transports the plate.

In the screening apparatus 13, the detecting apparatus 41 is provided with the imaging device 410. The imaging device 410 of the detecting apparatus 41 has same structure and function as the imaging device 410 of the detecting apparatus 40 in the screening apparatus 10. The detecting apparatus 41 of the screening apparatus 13 is not provided with the placing device 420 provided in the detecting apparatus 40. Instead, one portion of the transporting apparatus 55 is arranged in detecting apparatus 41. In the detecting apparatus 41 of the screening apparatus 13, the plate is transported to a predetermined imaging position by the transporting apparatus 55.

In the screening apparatus 13, the transporting apparatus 55 has a continuous transport line 56. The transport line 56 is a transporting route through which the plate is transported. As an example, the transporting apparatus 55 is provided with a continuous rail and a robot arm that is allowed to move on the rail. The plate is continuously move, namely transported, along the rail with the robot arm in a condition where the plate is grasped by the robot arm. In this case, the rail corresponds to the transport line 56. The transport line 56 includes a horizontal part 56a and a vertical part 56b. The horizontal part 56a of the transport line 56 continuously extends in the horizontal direction from an initial position P1 in the dispensing apparatus 21 to an imaging position P7 in the detecting apparatus 41. The vertical part 56b of the transport line 56 continuously extends in the vertical direction from one point (it is referred to as an intermediate position P4) on the horizontal part 56b of the transport line 56 to the cleaning position P6 via the drying position P5 in the cleaning and drying apparatus 33. Note that FIG. 13 illustrates the vertical part 56b of the transport line 56 as one line and this illustration corresponds to the case where the cleaning and drying apparatus 33 operates in accordance with the above described control method illustrated in FIG. 5. However, the vertical part 56b of the transport line 56 may be configured so that the cleaning and drying apparatus 33 operates in accordance with the above described control method illustrated in FIG. 6, FIG. 7 or FIG. 8.

In the screening apparatus 13, the dispensing apparatus 21, the cleaning and drying apparatus 33 and the detecting apparatus 41 share the transporting apparatus 55. The transport of the plate between the dispensing apparatus 21 and the cleaning and drying apparatus 33 and the transport of the plate between the cleaning and drying apparatus 33 and the detecting apparatus 41 are performed by the common transporting apparatus 55. The transporting apparatus 55 is an apparatus for transporting the plate between the dispensing apparatus 21 and the cleaning and drying apparatus 33 and also an apparatus for transporting the plate between the cleaning and drying apparatus 33 and the detecting apparatus 41.

An operation of the transport of the plate in the screening apparatus 13 will be described. The transport of the plate starts at the initial position P1 in the dispensing apparatus 21. As an example, the direction to which the plate faces at the initial position P1 is in the horizontal condition. Firstly, the transporting apparatus 55 transports the plate from the initial position P1 to the dispensing position P2 along the transport line 56 in the horizontal direction. The dispensing process is performed on the plate at the dispensing position P2. After the dispense process is finished, the transporting apparatus 55 transports the plate from the dispensing position P2 in the dispensing apparatus 21 to the intermediate position P4 above the cleaning and drying apparatus 33 along the transport line 56 in the horizontal direction. As an example, the plate is rotated at the intermediate position P4 from the horizontal condition to the upright condition. Furthermore, the transporting apparatus 55 transports the plate from the intermediate position P4 to the cleaning position P6 via the drying position P5 in the cleaning and drying apparatus 33 along the transport line 56 in the vertical direction. The cleaning process is performed on the plate at the cleaning position P6. After the cleaning process is finished, the transporting apparatus 55 transports the plate from the cleaning position P6 to the drying position P5 along the transport line 56 in the vertical direction. The drying process is performed on the plate at the drying process. After the drying process is finished, the transporting apparatus 55 transports the plate from the drying position P5 to the intermediate position P4 along the transport line 56 in the vertical direction. As an example, the plate is rotated at the intermediate position P4 from the upright condition to the horizontal condition. Furthermore, the transporting apparatus 55 transports the plate from the intermediate position P4 to the imaging position P7 in the detecting apparatus 41 along the transport line 56 in the horizontal direction. The detecting process is performed on the plate at the imaging position P7. In this way, the plate is transported by the transporting apparatus 55 from the initial position P1 to the dispensing position P2, then to the intermediate position P4, then to the drying position P5, then to the cleaning position P6, then to the drying position P5, then to the intermediate position P4 and finally to the imaging position P7 along the continuous transport line 56. In the screening apparatus 13, the dispensing apparatus 21, the cleaning and drying apparatus 33 and the detecting apparatus 41 share the transporting apparatus 55.

While the embodiments of the present invention were described above, the present invention is not limited thereto and thus a variety of changes are possible within a scope that does not depart from the gist of the present invention.

Although an example in which the plate is cleaned at the cleaning position by the cleaning device while being supported in the upright condition is illustrated, the present invention is not limited to this example. The plate may be cleaned at the cleaning position by the cleaning device while being supported in the horizontal condition, or may be cleaned at the cleaning position by the cleaning device while being supported in an inclined condition that is different from both of the upright condition and the horizontal condition. As an example, in the inclined condition, the x axis (see FIG. 1 and FIG. 2) of the plate coincides with the Y axis (see FIG. 3 to FIG. 8, FIG. 11 to FIG. 13), the y axis (see FIG. 1 and FIG. 2) of the plate 60 does not coincide with the X axis and the Z axis (see FIG. 3 to FIG. 8, FIG. 11 to FIG. 13), and the z axis (see FIG. 1 and FIG. 2) of the plate 60 does not coincide with the X axis and the Z axis (see FIG. 3 to FIG. 8, FIG. 11 to FIG. 13). As an example, in the inclined condition, the openings of the wells do not face to the X axis direction and the Z axis direction (see FIG. 3 to FIG. 8, FIG. 11 to FIG. 13).

A direction to which the plate 60 faces at the cleaning position may be same as or different from a direction to which the plate faces at the placement position. A direction to which the plate faces at the cleaning position may be same as or different from a direction to which the plate faces at the dispensing position. A direction to which the plate faces at the cleaning position may be same as or different from a direction to which the plate faces at the delivery position.

Although an example in which the plate is dried at the drying position by the drying device while being supported in the upright condition is illustrated, the present invention is not limited to this example. The plate may be dried at the drying position by the drying device while being supported in the horizontal condition, or may be dried at the drying position by the drying device while being supported in an inclined condition that is different from both of the upright condition and the horizontal condition. As an example, in the inclined condition, the x axis (see FIG. 1 and FIG. 2) of the plate coincides with the Y axis (see FIG. 3 to FIG. 8, FIG. 11 to FIG. 13), they axis (see FIG. 1 and FIG. 2) of the plate does not coincide with the X axis and the Z axis (see FIG. 3 to FIG. 8, FIG. 11 to FIG. 13), and the z axis (see FIG. 1 and FIG. 2) of the plate does not coincide with the X axis and the Z axis (see FIG. 3 to FIG. 8, FIG. 11 to FIG. 13). As an example, in the inclined condition, the openings of the wells do not face to the X axis direction and the Z axis direction (see FIG. 3 to FIG. 8, FIG. 11 to FIG. 13).

A direction to which the plate faces at the drying position may be same as or different from the direction to which the plate faces at the placement position. A direction to which the plate faces at the drying position may be same as or different from the direction to which the plate 60 faces at the dispensing position. A direction to which the plate aces at the drying position may be same as or different from the direction to which the plate faces at the delivery position.

When the plate is cleaned at the cleaning position while being supported in the inclined condition and the plate is dried at the drying position while being supported in the inclined condition, the plate may be transported between the cleaning position and the drying position by the transporting device while being supported in the inclined condition.

DESCRIPTION OF REFERENCE CODES

10 screening apparatus
20 dispensing apparatus
30 cleaning and drying apparatus
40 detecting apparatus
50 transporting apparatus
60 plate
210 transporting device
220 dispensing device
230 controlling device
310 cleaning device
311 cleaning solution supplying part
311b cleaning solution supplying pipe
312 cleaning solution nozzle
320 drying device
321 blower part
321b blower pipe
322 blower outlet
330 transporting device
340 controlling device
350 housing device
360 waste solution collecting device
410 imaging device
420 placing device

The invention claimed is:

1. A cleaning and drying apparatus for a plate having a biochip, the cleaning and drying apparatus comprising:
   a cleaner that is configured to clean the plate in an upright condition;
   a dryer that is configured to dry the plate in an upright condition, the dryer being arranged above the cleaner; and
   a rotational operator that is configured to rotate the uncleaned plate in a horizontal condition to an upright condition and then to rotate the dried plate in an upright condition to a horizontal condition again.

2. The cleaning and drying apparatus according to claim 1 comprising a transporter that is configured to upwardly transport the plate cleaned by the cleaner to the dryer.

3. The cleaning and drying apparatus according to claim 2, wherein
   the transporter is configured to downwardly transport the uncleaned plate to the cleaner while allowing the uncleaned plate to pass through the dryer.

4. The cleaning and drying apparatus according to claim 2, wherein the transporter is configured to transport the plate in a vertical direction from the cleaner to the dryer at an upper side.

5. The cleaning and drying apparatus according to claim 1, wherein
the dryer is arranged above the cleaner in a vertical direction.

6. The cleaning and drying apparatus according to claim 1, wherein
the cleaner is configured to clean both surfaces of the plate,
the dryer is configured to dry both surfaces of the plate.

7. The cleaning and drying apparatus according to claim 1 comprising a circulator that is configured to filter exhaust air from the dryer to allow the exhaust air to be reused for the drying.

8. The cleaning and drying apparatus according to claim 1 comprising a waste solution storage below the cleaner.

9. The cleaning and drying apparatus according to claim 1, wherein
a cleaning position in the cleaner is a position that is displaced in a horizontal direction from a drying position in the dryer.

10. A screening apparatus for a biochip, the screening apparatus comprising:
the cleaning and drying apparatus according to claim 1;
a dispenser configured to dispense, in a plate having the biochip, a specimen containing a target that is able to react specifically to a biomolecule fixed on the biochip; and
a detector that is configured to detect affinity between the target and the biomolecule.

11. The screening apparatus according to claim 10, further comprising a transporter configured to transport the plate from the dispenser to the cleaning and drying apparatus in a horizontal direction and to transport the plate from the cleaning and drying apparatus to the detector in a horizontal direction.

12. The screening apparatus according to claim 11, wherein
the transporter is configured to transport the plate in a horizontal condition from the dispenser to the cleaning and drying apparatus in a horizontal direction and to transport the plate in a horizontal condition from the cleaning and drying apparatus to the detector in a horizontal direction.

13. A cleaning and drying method for a plate having a biochip, the cleaning and drying method comprising:
performing, by a cleaning and drying apparatus, operations including:
transporting the plate to a cleaning position;
cleaning the plate at the cleaning position;
transporting the cleaned plate to a drying position that is located above the cleaning position;
drying the plate at the drying position;
rotating the uncleaned plate in a horizontal condition to an upright condition by using a rotational operator; and
rotating the dried plate in an upright condition to a horizontal condition again by using the rotational operator,
wherein the rotational operator is configured to rotate the uncleaned plate in a horizontal condition to an upright condition and then to rotate the dried plate in an upright condition to a horizontal condition.

14. The cleaning and drying method according to claim 13, wherein
the transporting the plate to the cleaning position includes transporting the plate in a upright condition to the cleaning position,
the cleaning the plate at the cleaning position includes cleaning the plate in a upright condition,
the transporting the cleaned plate to the drying position that is located above the cleaning position includes transporting the plate in a upright condition to the drying position, and
the drying the plate at the drying position includes drying the plate in an upright condition.

15. The cleaning and drying method according to claim 13, wherein
the transporting the plate to the cleaning position includes downwardly transporting the plate to the cleaning position while allowing the plate to pass through the drying position.

16. The cleaning and drying method according to claim 13, wherein
the cleaning the plate at the cleaning position includes cleaning both surfaces of the plate,
the drying the plate at the drying position includes drying both surfaces of the plate.

17. A screening method using a plate having a biochip, the screening method comprising:
dispensing, in a plate having a biochip, a specimen containing a target that is able to react specifically to a biomolecule fixed on the biochip, in a dispenser;
performing the cleaning and drying method according to claim 13 in the cleaning and drying apparatus; and
detecting an affinity between the target and the biomolecule in a detector.

18. The screening method according to claim 17 comprising:
transporting the dispensed plate from the dispenser to the cleaning and drying apparatus in a horizontal direction; and
transporting the cleaned and dried plate from the cleaning and drying apparatus to the detector in a horizontal direction.

19. The screening method according to claim 18, wherein
the dispensed plate in a horizontal condition is transported from the dispenser to the cleaning and drying apparatus in a horizontal direction, and
the cleaned and dried plate in a horizontal condition is transported from the cleaning and drying apparatus to the detector in a horizontal direction.

* * * * *